United States Patent
De Luca et al.

(10) Patent No.: US 11,072,613 B2
(45) Date of Patent: Jul. 27, 2021

(54) COMPOSITIONS AND METHODS FOR MAKING TERPENOID INDOLE ALKALOIDS

(71) Applicant: Willow BioSciences Inc., Calgary (CA)

(72) Inventors: Vincenzo De Luca, Ontario (CA); Yang Qu, St. Catharines (CA)

(73) Assignee: Willow Biosciences, Inc., Calgary (CA)

( * ) Notice: Subject to any disclaimer, the term of this patent is extended or adjusted under 35 U.S.C. 154(b) by 0 days.

(21) Appl. No.: 16/081,645

(22) PCT Filed: Mar. 2, 2017

(86) PCT No.: PCT/CA2017/050284
§ 371 (c)(1),
(2) Date: Aug. 31, 2018

(87) PCT Pub. No.: WO2017/152273
PCT Pub. Date: Sep. 14, 2017

(65) Prior Publication Data
US 2020/0002339 A1   Jan. 2, 2020

Related U.S. Application Data

(60) Provisional application No. 62/302,342, filed on Mar. 2, 2016.

(51) Int. Cl.
| | | |
|---|---|---|
| *C07D 471/16* | (2006.01) | |
| *C07D 455/00* | (2006.01) | |
| *C07D 471/04* | (2006.01) | |
| *C07D 471/18* | (2006.01) | |
| *C07D 491/18* | (2006.01) | |
| *C12N 9/02* | (2006.01) | |
| *C12N 15/70* | (2006.01) | |

(52) U.S. Cl.
CPC ......... *C07D 471/16* (2013.01); *C07D 455/00* (2013.01); *C07D 471/04* (2013.01); *C07D 471/18* (2013.01); *C07D 491/18* (2013.01); *C12N 9/001* (2013.01); *C12N 9/0055* (2013.01); *C12N 15/70* (2013.01); *C12Y 103/01036* (2013.01); *C12Y 110/00* (2013.01)

(58) Field of Classification Search
None
See application file for complete search history.

(56) References Cited

FOREIGN PATENT DOCUMENTS

WO    WO 00/42200 A1    7/2000

OTHER PUBLICATIONS

Schroder et al., "Light-induced cytochrome P450-dependent enzyme in indole alkaloid biosynthesis: tabersonine 16-hydroxylase", FEBS Letters 458: 97-102 (1999). (Year: 1999).*
Bede and DiCosmo, "Enzymatic synthesis of alpa-3',4'-Anhydrovinblastine: Optimization and Immobilization", Planta Med. 58: Supplement Issue 1, p. A576. (Year: 1992).*
De Bernonville et al.,"Characterization of a second secologanin synthase isoform producing both secologanin and secoxyloganin allows enhanced de novo assembly of a Catharanthus roseus transcriptome", BMC Genomics 16: 619 pp. 1 to 19. (Year: 2015).*
Gerasimenko et al.."Heterologous expression of a Rauvolfia cDNA encoding strictosidine glucosidase, a biosynthetic key to over 2000 monoterpenoid indole alkaloids", Eur. J. Biochem. 269: 2204-2213. (Year: 2002).*
Batra, et al., "Strictosidine-O-beta-D-glucosidase" Jan. 1, 2009 (Retrieved from the Internet: <ABW77570> http://www.uniprot.org/uniprot/B8PRP4).
Pan et al., "Monoterpenoid indole alkaloids biosynthesis and its regulation in Catharanthus roseus: a literature review from genes to metabolites", Phytochem rev, Apr. 1, 2015, vol. 15, p. 221-250.
Qu et al., "Completion of the seven-step pathway from tabersonine to the anticancer drug precursor vindoline and its assembly in yeast", PNAS, May 12, 2015, vol. 112(19), p. 6224-6229.
Luijendijk, T.J.C., et al., "Purification and characterizationof strictosidine beta-D-glucosidase from Catharanthus roseus cell suspension cultures", Plant Physiology and Biochemistry, Gauthier-Villars Pads, Frane, vol. 36, No. 6, p. 419-425, Jan. 1998.
Whitmer, S. et al., "Influence of precursor availability on alkaloid accumulation by transgenic cell line of Cathranthus roseus", Plant Physiology, American Society of Plant Physiologists, Rockville, MD, USA, vol. 116, p. 853-857, Jan. 1998.

* cited by examiner

*Primary Examiner* — Anand U Desai
(74) *Attorney, Agent, or Firm* — Fisherbroyles LLP; Adam Whiting

(57) ABSTRACT

Methods that may be used for the manufacture of a class of chemical compounds known as terpenoid indole alkaloids, including tabersonine and catharanthine are provided. Compositions useful for the synthesis of terpenoid indole alkaloids, including tabersonine and catharanthine are also provided. The provided compounds are useful in the manufacture of chemotherapeutic agents.

15 Claims, 18 Drawing Sheets

Specification includes a Sequence Listing.

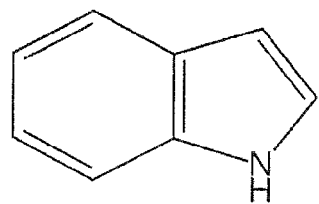
FIG. 1A
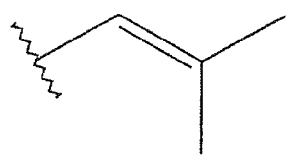
FIG. 1B
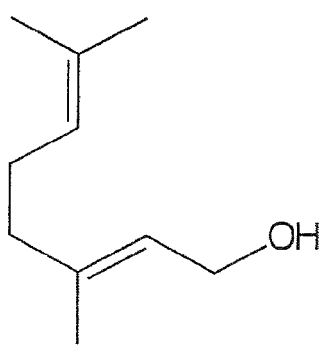
FIG. 1C
FIGURE 1

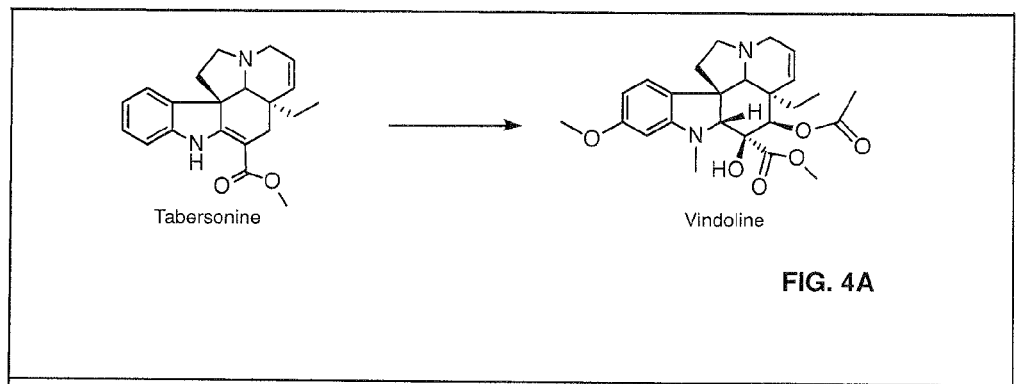
FIG. 4A
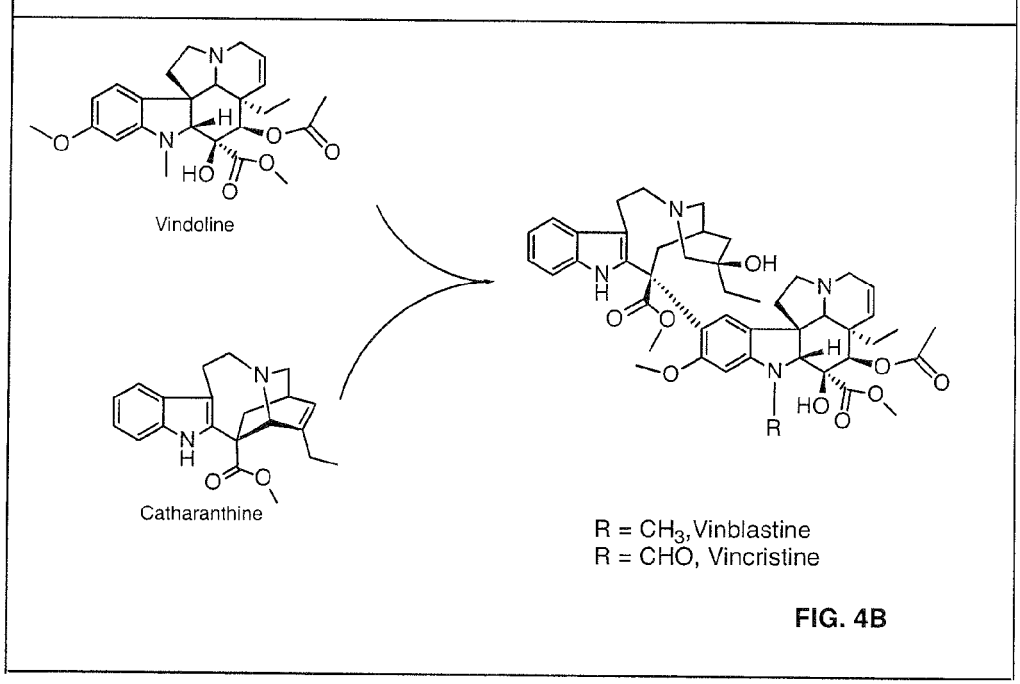
R = CH₃, Vinblastine
R = CHO, Vincristine
FIG. 4B
FIGURE 4

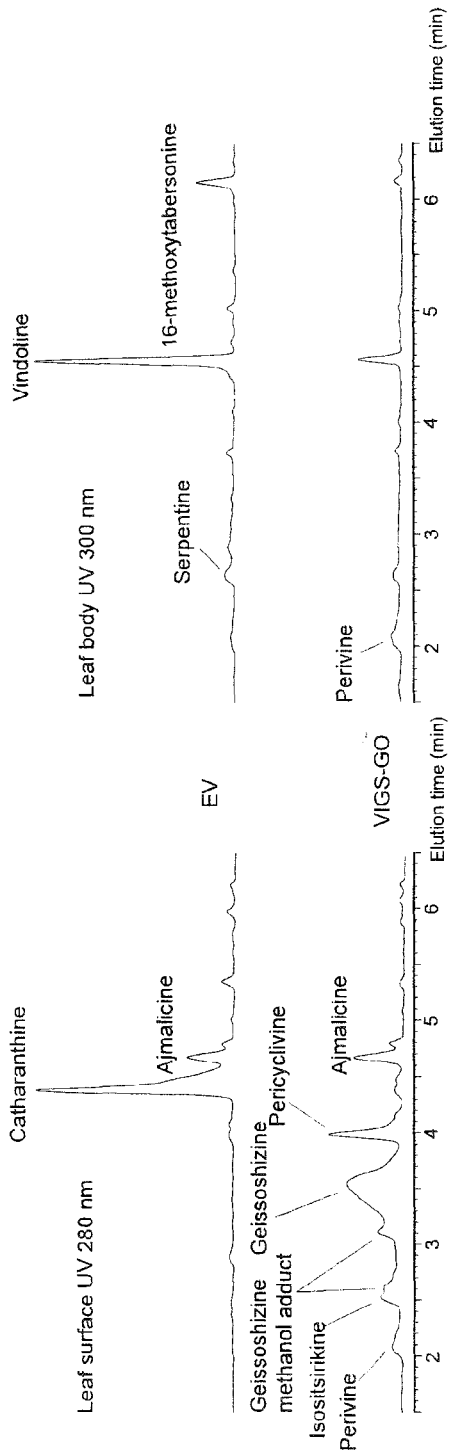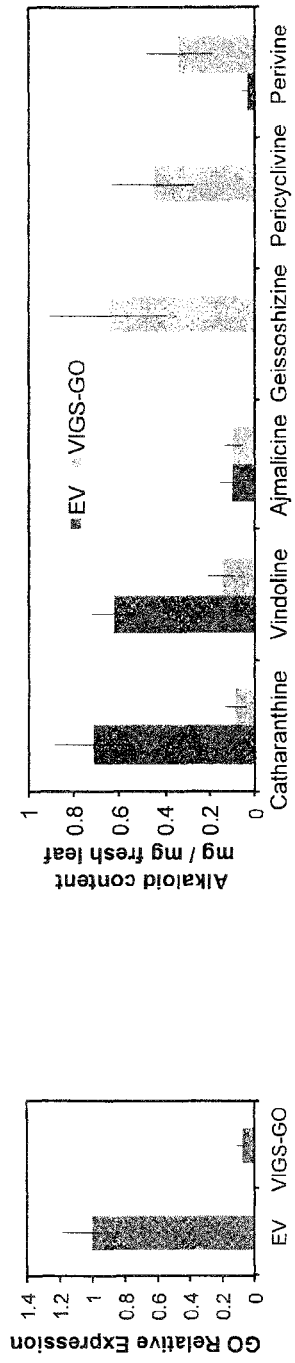
FIG. 13A
FIG. 13B
FIG. 13C
FIG. 13D
FIGURE 13

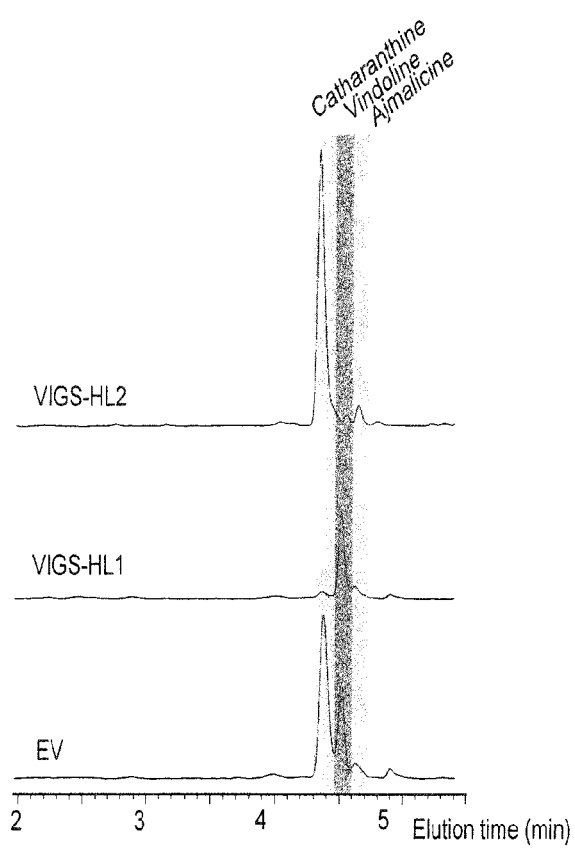
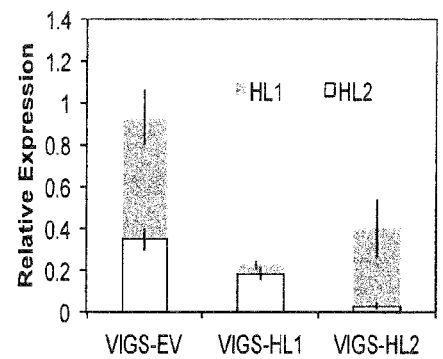
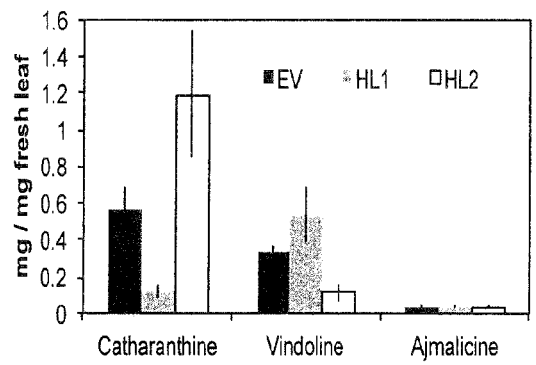
FIG. 16A
FIG. 16B
FIG. 16C
FIGURE 16

COMPOSITIONS AND METHODS FOR MAKING TERPENOID INDOLE ALKALOIDS

CROSS-REFERENCE TO RELATED APPLICATION

This application is a national phase entry application of Patent Cooperation Treaty Application No. PCT/CA2017/050284 filed Mar. 2, 2017 (which designates the U.S.), which claims the benefit of U.S. Provisional Patent Application No. 62/302,342 filed on Mar. 2, 2016. The entire contents of U.S. Provisional Patent Application 62/302,342 and PCT/CA2017/050284 are hereby incorporated by reference in their entirety.

INCORPORATION OF SEQUENCE LISTING

A computer readable form of the Sequence Listing "21806-P50497US01_SequenceListing.txt" (143,360 bytes), submitted via EFS-WEB and created on Aug. 30, 2018 and amended on Jan. 14, 2019, is herein incorporated by reference.

FIELD OF THE DISCLOSURE

The compositions and methods disclosed herein relate to a class of chemical compounds known as terpenoid indole alkaloids. More particularly, the present disclosure relates to catharanthine and tabersonine, and related terpenoid indole alkaloids, and to processes for making and using the same, in particular in the manufacture of chemotherapeutic agents.

BACKGROUND OF THE DISCLOSURE

The following paragraphs are provided by way of background to the present disclosure. They are not however an admission that anything discussed therein is prior art or part of the knowledge of persons skilled in the art.

Alkaloid compounds belonging to the class of chemical compounds known as terpenoid indole alkaloids are known to exhibit pharmacological properties. Vinblastine and vincristine, for example, are used as chemotherapeutic agents, including as agents for the treatment of Hodgkin's lymphoma, acute leukemia, testicular carcinoma, brain cancer and bladder cancer (Moudi, M. et al., 2013, *Int. J. Prev. Med.* 4(11) 1231-1235; De Luca V. et al., 2014, *Curr Opin Plant Biol* 19; 35-42; and De Luca V. et al., 2014, *Science*, 336 (6089), 1658-1661). It is therefore well appreciated in the art that techniques for manufacturing terpenoid indole alkaloids, including vincristine and vinblastine, are highly desirable.

Although certain methodologies for manufacturing vincristine and vinblastine have evolved, the heretofore known methodologies exhibit significant limitations. Thus both vincristine and vinblastine may be de nova synthesized (see: Yokoshima S. et al., 2003, *Pure Appl. Chem.* 75(1) 29-38; Kuboyama, T. et al., 2004, *Proc Natl. Acad. Sci.*, 101 (33), 11966-11970). However the complexity of the chemical structures of vincristine and vinblastine, makes such synthetic manufacturing techniques inherently challenging, and these methodologies are in particular impractical to employ in the manufacture of therapeutic quantities of vincristine and vinblastine on a commercial scale.

It is also well documented that vincristine and vinblastine may be extracted from the leaves of *Catharanthus roseus*, a plant also known as Madagascar periwinkle (De Luca V. et al., 2014, *Curr Opin Plant Biol* 19; 35-42; and De Luca V. et al., 2014, *Science*, 336 (6089), 1658-1661). The quantities of terpenoid indole alkaloid compounds present in the plant, however, are extremely low. The leaves of *Catharanthus roseus* have been found to constitute 0.00025% vinblastine of dry leaf weight (Shikawa, H., 2008, *J. Am. Chem. Soc.* 130(2): 420-421; Noble, R L et al., 1958, *Ann. N.Y. Acad. Sci.* 76, 882). Thus the production of vinblastine and vincristine from *Catharanthus roseus* requires the growth and processing of a very large amount of plant material, rendering production from this natural source impractical and costly. The challenges associated with processing of *Catharanthus roseus* plants are further compounded by the fact there is a lack of robust cultivation techniques available to grow and harvest *Catharanthus roseus* plants or plant material and secure a reliable product supply.

Another approach to the production of vincristine and vinblastine would involve the biosynthetic production of vincristine and vinblastine facilitated by a microbial host organism manipulated to biosynthetically generate these compounds, or precursor compounds of vincristine and vinblastine. Such a system would be particularly desirable, as it would allow for substantial production quantities of vincristine and vinblastine under carefully controlled operational conditions. Two terpenoid indole alkaloid precursor compounds are of particular interest in this regard, catharanthine and tabersonine, since the chemical coupling of vindoline, to which tabersonine is a precursor compound, and catharanthine permits the production of vincristine and vinblastine (Ishikawa, H., 2008, *J. Am. Chem. Soc.* 130(2): 420-421). However the biosynthetic pathways for producing catharanthine and tabersonine, involved in converting pathway intermediate compounds from strictosidine, the chemical compound thought to be a precursor to catharanthine and tabersonine, are not understood. Furthermore the requisite enzymes capable of catalyzing the chemical conversion reactions, as well as the genes encoding these enzymes are unknown. Thus, despite the desirability of a biosynthetic production methodology, it remains uncertain whether and how the precursor compounds catharanthine and tabersonine may be produced biosynthetically, and it remains uncertain how a biosynthetic production system for vincristine and vinblastine may be obtained.

It thus is apparent from the foregoing that the existing manufacturing methods for terpenoid indole alkaloids suffer from low yields and/or are expensive. More specifically, no methods exist to biosynthetically make catharanthine and tabersonine, two important precursor compounds in the pathway for biosynthesis of vincristine and vinblastine. There exists therefore in the art a need for improved methods for the synthesis of terpenoid indole alkaloids, including tabersonine and catharanthine.

SUMMARY OF THE DISCLOSURE

The following paragraphs are intended to introduce the reader to the more detailed description that follows and not to define or limit the claimed subject matter of the present disclosure.

The present disclosure relates to certain alkaloids belonging to the class of terpenoid indole alkaloid compounds, as well as to methods for making such terpenoid indole alkaloid compounds.

The present disclosure further relates to the terpenoid indole alkaloid compounds obtainable through enzyme mediated chemical modifications of other terpenoid indole alkaloid compounds.

The present disclosure further relates to the terpenoid indole alkaloid compounds tabersonine and catharanthine, synthesis intermediates thereof and derivatives of synthesis intermediates, as well as to methods of making tabersonine and catharanthine, synthesis intermediates thereof and synthesis derivatives thereof.

In one aspect, the present disclosure provides, in at least one embodiment, a method of making tabersonine, catharanthine, a tabersonine-catharanthine synthesis intermediate, or a tabersonine-catharanthine synthesis derivative comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); (iv) reductase 1 (REDOX 1); (v) reductase 2 (REDOX 2); (vi) stemmadenine acetyl transferase (SAT); (vii) hydrolyase 1 (HL1); and (viii) hydrolyase 2 (HL2) under reaction conditions permitting the catalysis of the terpenoid indole alkaloid compound to form tabersonine, catharanthine, a tabersonine-catharanthine synthesis intermediate, or a tabersonine-catharanthine synthesis derivative.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative compound.

In some embodiments, the terpenoid indole alkaloid compound is selected from the group consisting of strictosidine; 4,21-dehydrogeissoschizine; geissoschizine; monooxygenated geissoschizine; strictosidine aglycone; and a strictosidine aglycone derivative; and the tabersonine-catharanthine synthesis intermediate is selected from the group consisting of 4,21-dehydrogeissoschizine; geissoschizine; and monooxygenated geissoschizine.

In some embodiments, the terpenoid indole alkaloid compound is selected from the group consisting of strictosidine; 4,21-dehydrogeissoschizine; geissoschizine; monooxygenated geissoschizine; strictosidine aglycone; and a strictosidine aglycone derivative; and the tabersonine-catharanthine synthesis derivative is selected from the group consisting of ajmalicine; isositsirikine; pericyclivine; perivine; akuammicine; MIA1; MIA 2; stemmadenine and O-acetylstemmadenine.

In some embodiments, the tabersonine-catharanthine pathway precursor compound is selected from the group consisting of strictosidine; 4,21-dehydrogeissoschizine; geissoschizine; monooxygenated; and geissoschizine; and the tabersonine-catharanthine pathway precursor derivative compound is selected from strictosidine aglycone or a strictosidine aglycone derivative In some embodiments, the strictosidine aglycone derivative comprises at least one of cathenamine, cathenamine (iminium form), 19-epi-cathenamine and 19-epi-cathenamine (iminium form).

In some embodiments, the strictosidine aglycone derivative comprises at least one of cathenamine, cathenamine (iminium form), 19-epi-cathenamine and 19-epi-cathenamine (iminium form), and the strictosidine aglycone derivative further comprises 4,21-dehydrogeissoschizine.

In another aspect, the present disclosure provides, in at least one embodiment, methods for making tabersonine. Accordingly, the present disclosure provides, in at least one embodiment, a method of making tabersonine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); (iv) reductase 1 (REDOX 1); (v) reductase 2 (REDOX 2); (vi) stemmadenine acetyl transferase (SAT); (vii) hydrolyase 1 (HL1) and (viii) hydrolyase 2 (HL2) under reaction conditions permitting the catalysis of the terpenoid indole alkaloid compound to form tabersonine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine, and the enzymes are (i) SGD; (ii) GS; (iii) GO; (iv) REDOX 1; (v) REDOX 2; (vi) SAT; and (vii) HL2.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzymes are (i) GS; (ii) GO; (iii) REDOX 1; (iv) REDOX 2; (v) SAT; and (vi) HL2.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; (ii) GO; (iii) REDOX 1; (iv) REDOX 2; (v) SAT; and (vi) HL2.

In some embodiments, the terpenoid indole alkaloid compound is a tabersonine-catharanthine pathway precursor compound, the tabersonine-catharanthine pathway precursor compound is geissoschizine, and the enzymes are (i) GO; (ii) REDOX 1; (iii) REDOX 2; (iv) SAT and (v) HL2.

In some embodiments, the terpenoid indole alkaloid compound is a tabersonine-catharanthine pathway precursor compound, the tabersonine-catharanthine pathway precursor compound is monooxygenated geissoschizine and the enzymes are (i) REDOX 1; (ii) REDOX 2; (iii) SAT; and (iv) HL2.

In another aspect, the present disclosure provides, in at least one embodiment, methods for making catharanthine. Accordingly, the present disclosure provides, in at least one embodiment, a method of making catharanthine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); (iv) reductase 1 (REDOX 1): (v) reductase 2 (REDOX 2); (vi) stemmadenine acetyl transferase (SAT); (vii) hydrolyase 1 (HL1); and (viii) hydrolyase 2 (HL2) under reaction conditions permitting the catalysis of the terpenoid indole alkaloid compound to form catharanthine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine, and the enzymes are (i) SGD; (ii) GS; (iii) GO; (iv) REDOX 1; (v) REDOX 2; (vi) SAT; and (vii) HL1.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzymes are; (i) GS; (ii) GO; (iii) REDOX 1; (iv) REDOX 2; (v) SAT; and (vi) HL1.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; (ii) GO; (iii) REDOX 1; (iv) REDOX 2; (v) SAT; and (vi) HL1.

In some embodiments, the terpenoid indole alkaloid compound is a tabersonine-catharanthine pathway precursor compound, the tabersonine-catharanthine pathway precursor compound is geissoschizine, and the enzymes are (i) GO; (ii) REDOX 1; (iii) REDOX 2; (iv) SAT; and (v) HL1.

In some embodiments, the terpenoid indole alkaloid compound is a tabersonine-catharanthine pathway precursor compound, the tabersonine-catharanthine pathway precursor compound is monooxygenated geissoschizine, and the enzymes are (i) REDOX 1; (ii) REDOX 2; (iii) SAT; and (iv) HL1.

In another aspect, the present disclosure provides, in at least one embodiment, methods for making the tabersonine-catharanthine synthesis intermediate, monooxygenated geissoschizine. Accordingly, the present disclosure provides, in at least one embodiment, a method of making monooxygenated geissoschizine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO), under reaction conditions permitting the catalysis of the terpenoid indole alkaloid compound to form monooxygenated geissoschizine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine, and the enzymes are (i) SGD; (ii) GS; and (iii) GO.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzymes are; (i) GS; and (ii) GO.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; and (ii) GO.

In some embodiments, the terpenoid indole alkaloid compound is a tabersonine-catharanthine pathway precursor compound, the tabersonine-catharanthine pathway precursor compound is geissoschizine and the enzymes is GO.

In another aspect, the present disclosure provides, in at least one embodiment, methods for making the tabersonine-catharanthine synthesis intermediate, geissoschizine. Accordingly, the present disclosure provides, in at least one embodiment, a method of making geissoschizine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); and (ii) geissoschizine synthase (GS), under reaction conditions permitting the catalysis of the terpenoid indole alkaloid compound to form geissoschizine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine, and the enzymes are (i) SGD; and (ii) GS.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzyme is GS.

In some embodiments, the terpenoid indole alkaloid compound is a tabersonine-catharanthine pathway precursor compound, the tabersonine-catharanthine pathway precursor is 4,21-dehydrogeissoschizine and the enzyme is GS.

In another aspect, the present disclosure provides, in at least one embodiment, methods for making the tabersonine-catharanthine synthesis intermediate, 4,21-dehydrogeissoschizine. Accordingly, the present disclosure provides, in at least one embodiment, a method of making 4,21-dehydrogeissoschizine, comprising:
(a) providing a terpenoid indole alkaloid compound; and
(b) contacting the terpenoid indole alkaloid compound with catalytic quantities of strictosidine β-glucosidase (SGD) under reaction conditions permitting the catalysis of the terpenoid indole alkaloid compound to form 4,21-dehydrogeissoschizine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, and the tabersonine-catharanthine pathway precursor compound is strictosidine.

In another aspect, the present disclosure provides, in at least one embodiment, methods for making the tabersonine-catharanthine synthesis derivative, ajmalicine. Accordingly, the present disclosure provides, in at least one embodiment, a method of making ajmalicine, comprising:
(a) providing a terpenoid indole alkaloid compound; and
(b) contacting the terpenoid indole alkaloid compound with catalytic quantities of strictosidine β-glucosidase (SGD) under reaction conditions permitting the catalysis of the terpenoid indole alkaloid compound to form ajmalicine.

In some embodiments, the terpenoid indole alkaloid compound is a tabersonine-catharanthine pathway precursor compound.

In some embodiments, the terpenoid indole alkaloid compound is strictosidine.

In another aspect, the present disclosure provides, in at least one embodiment, methods for making the tabersonine-catharanthine synthesis derivative, isositsirikine. Accordingly, the present disclosure provides, in at least one embodiment, a method of making isositsirikine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); and (iii) reductase 2 (REDOX 2) under reaction conditions permitting the catalysis of the terpenoid indole alkaloid compound to form isositsirikine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is geissoschizine, and the enzyme is REDOX 2.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; and (ii) REDOX 2.

In some embodiments, the terpenoid indole alkaloid compound is a tabersonine-catharanthine pathway precursor compound, the tabersonine-catharanthine pathway precursor compound is strictosidine, and the enzymes are (i) SGD; (ii) GS; and (iii) REDOX 2.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzymes are (i) GS and (iii) REDOX 2.

In another aspect, the present disclosure provides, in at least one embodiment, methods for making the tabersonine-catharanthine synthesis derivative, pericyclivine. Accordingly, the present disclosure provides, in at least one embodiment, a method of making pericyclivine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); and (ii) geissoschizine synthase (GS); under reaction conditions permitting the catalysis of the terpenoid indole alkaloid compound to form pericyclivine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is 4,21-dehydrogeissoschizine, and the enzyme is GS.

In some embodiments, the terpenoid indole alkaloid compound is a tabersonine-catharanthine pathway precursor compound, the tabersonine-catharanthine pathway precursor compound is strictosidine and the enzymes are (i) SGD; and (ii) GS.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzyme is GS.

In another aspect, the present disclosure provides, in at least one embodiment, methods for making the tabersonine-catharanthine synthesis derivative, perivine. Accordingly, the present disclosure provides, in at least one embodiment, a method of making perivine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); and (ii) geissoschizine synthase (GS); under reaction conditions permitting the catalysis of the terpenoid indole alkaloid compound to form perivine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is 4,21-dehydrogeissoschizine, and the enzyme is GS.

In some embodiments, the terpenoid indole alkaloid compound is a tabersonine-catharanthine pathway precursor compound, the tabersonine-catharanthine pathway precursor compound is strictosidine and the enzymes are (i) SGD; and (ii) GS.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzyme is GS.

In another aspect, the present disclosure provides, in at least one embodiment, methods for making the tabersonine-catharanthine synthesis derivative, akuammicine. Accordingly, the present disclosure provides, in at least one embodiment, a method of making akuammicine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); and (iii) GO under reaction conditions permitting the catalysis of the terpenoid indole alkaloid compound to form akuammicine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is geissoschizine, and the enzyme is GO.

In some embodiments, the terpenoid indole alkaloid compound is a tabersonine-catharanthine pathway precursor compound, the tabersonine-catharanthine pathway precursor compound is 4,21-dehydrogeissoschizine and the enzyme is (i) GS; and (ii) GO.

In some embodiments, the terpenoid indole alkaloid compound is a tabersonine-catharanthine pathway precursor compound, the tabersonine-catharanthine pathway precursor compound is strictosidine and the enzymes are (i) SGD; (ii) GS; and (iii) GO.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzyme is (i) GS and (ii) GO.

In another aspect, the present disclosure provides, in at least one embodiment, methods for making the tabersonine-catharanthine synthesis derivative, 16S-desformylstemmadenine (MIA1). Accordingly, the present disclosure provides, in at least one embodiment, a method of making MIA1, comprising:

(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine synthase (GO); and (iv) redox 1 (REDOX 1) under reaction conditions permitting the catalysis of the terpenoid indole alkaloid compound to form MIA1.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is monooxygenated geissoschizine, and the enzyme is REDOX 1.

In some embodiments, the terpenoid indole alkaloid compound is a tabersonine-catharanthine pathway precursor compound, the tabersonine-catharanthine pathway precursor compound is geissoschizine and the enzymes are (i) GO; and (ii) REDOX 1.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; (ii) GO; and (iii) REDOX 1.

In some embodiments, the terpenoid indole alkaloid compound is a tabersonine-catharanthine pathway precursor compound, the tabersonine-catharanthine pathway precursor compound is strictosidine and the enzymes are (i) SGD; (ii) GS; (iii) GO; and REDOX 1.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzyme is (i) GS; (ii) GO; and (iii) REDOX 1.

In another aspect, the present disclosure provides, in at least one embodiment, methods for making the tabersonine-catharanthine synthesis derivative, 16R-desformylstemmadenine (MIA2). Accordingly, the present disclosure provides, in at least one embodiment, a method of making MIA2, comprising:

(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); and (iv) reductase 1 (REDOX 1) under reaction conditions permitting the catalysis of the terpenoid indole alkaloid compound to form MIA2.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is monooxygenated geissoschizine, and the enzyme is REDOX 1.

In some embodiments, the terpenoid indole alkaloid compound is a tabersonine-catharanthine pathway precursor compound, the tabersonine-catharanthine pathway precursor compound is geissoschizine and the enzymes are (i) GO; and (ii) REDOX 1.

In some embodiments, the terpenoid indole alkaloid compound is a tabersonine-catharanthine pathway precursor compound, the tabersonine-catharanthine pathway precursor compound is 4,21-dehydrogeissoschizine, and the enzymes are (i) GS; (ii) GO; and (iii) REDOX 1.

In some embodiments, the terpenoid indole alkaloid compound is a tabersonine-catharanthine pathway precursor compound, the tabersonine-catharanthine pathway precursor compound is strictosidine and the enzymes are (i) SGD; (ii) GS; (iii) GO; and REDOX 1.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative, and the enzyme is (i) GS; (ii) GO; and (iii) REDOX 1.

In another aspect, the present disclosure provides, in at least one embodiment, methods for making the tabersonine-catharanthine synthesis derivative, O-acetylstemmadenine. Accordingly, the present disclosure provides, in at least one embodiment, a method of making O-acetylstemmadenine, comprising:

(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); (iv) reductase 1 (REDOX 1); (v) reductase 2 (REDOX 2); and (vi) stemmadenine acetyl transferase (SAT) under reaction conditions permitting the catalysis of the terpenoid indole alkaloid compound to form O-acetylstemmadenine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine, and the enzymes are (i) SGD; (ii) GS; (iii) GO; (iv) REDOX 1; (v) REDOX 2; and (vi) SAT.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzymes are (i) GS; (ii) GO; and (iii) REDOX 1; (iv) REDOX 2; and (v) SAT.

In some embodiments, the terpenoid indole alkaloid compound is a tabersonine-catharanthine pathway precursor compound, the tabersonine-catharanthine pathway precursor compound is 4,21-dehydrogeissoschizine and the enzyme is (i) GS; (ii) GO; (iii) REDOX 1: (iv) REDOX 2; and (v) SAT.

In some embodiments, the terpenoid indole alkaloid compound is a tabersonine-catharanthine pathway precursor compound, the tabersonine-catharanthine pathway precursor compound is geissoschizine and the enzyme is (i) GO; and (ii) REDOX 1; (iii) REDOX 2; and (iv) SAT.

In some embodiments, the terpenoid indole alkaloid compound is a tabersonine-catharanthine pathway precursor compound, the tabersonine-catharanthine pathway precursor compound is monooxygenated geissoschizine and the enzymes are (i) REDOX 1; (ii) REDOX 2; and (iii) SAT.

In some embodiments, the terpenoid indole alkaloid compound is a tabersonine-catharanthine synthesis derivative, the tabersonine-catharanthine pathway synthesis derivative is stemmadenine, and the enzyme is SAT.

In another aspect, the present disclosure provides, in at least one embodiment, methods for making the tabersonine-catharanthine synthesis derivative, stemmadenine. Accordingly, the present disclosure provides, in at least one embodiment, a method of making stemmadenine, comprising:
(a) providing a terpenoid indole alkaloid compound; and
(b) contacting the terpenoid indole alkaloid compound with catalytic quantities of at least one of the enzymes selected from the group consisting of (i) strictosidine β-glucosidase (SGD); (ii) geissoschizine synthase (GS); (iii) geissoschizine oxidase (GO); (iv) reductase 1 (REDOX 1); and (v) reductase 2 (REDOX 2) under reaction conditions permitting the catalysis of the terpenoid indole alkaloid compound to form stemmadenine.

In some embodiments, the terpenoid indole alkaloid compound is a tabersonine-catharanthine pathway precursor compound.

In some embodiments, the terpenoid indole alkaloid compound is a tabersonine-catharanthine pathway precursor derivative.

In some embodiments, the terpenoid indole alkaloid compound is a tabersonine-catharanthine pathway precursor compound, the tabersonine-catharanthine pathway precursor compound is strictosidine and the enzymes are (i) SGD; (ii) GS; (iii) GO; (iv) REDOX 1; and (v) REDOX 2.

In some embodiments, the terpenoid indole alkaloid compound is a tabersonine-catharanthine pathway precursor derivative, the tabersonine-catharanthine pathway precursor derivative is strictosidine aglycone or a strictosidine aglycone derivative and the enzymes are (i) GS; (ii) GO; and (iii) REDOX 1; and (iv) REDOX 2.

In some embodiments, the terpenoid indole alkaloid compound is a tabersonine-catharanthine pathway precursor compound, the tabersonine-catharanthine pathway precursor compound is 4,21-dehydrogeissoschizine and the enzyme is (i) GS; (ii) GO; (iii) REDOX 1; and (iv) REDOX 2.

In some embodiments, the terpenoid indole alkaloid compound is a tabersonine-catharanthine pathway precursor compound, the tabersonine-catharanthine pathway precursor compound is geissoschizine and the enzyme is (i) GO; and (ii) REDOX 1; and (iii) REDOX 2.

In some embodiments, the terpenoid indole alkaloid compound is a tabersonine-catharanthine pathway precursor compound, the tabersonine-catharanthine pathway precursor compound is monooxygenated geissoschizine and the enzymes are (i) REDOX 1; and (ii) REDOX 2.

In some embodiments, the reaction conditions are in vitro reaction conditions.

In some embodiments, the reaction conditions are in vivo reaction conditions.

In another aspect, the present disclosure provides, in some embodiments uses of enzymes, notably, SGD, GS, GO, REDOX 1, REDOX 2, SAT, HL1 and HL2

In some embodiments, the present disclosure provides a use of SGD as an enzyme to catalytically convert strictosidine to form 4,21-dehydrogeissoschizine.

In at least one embodiment, SGD is protein comprising the polypeptide sequence set forth in SEQ ID NO: 1 or a sequence substantially identical thereto.

In some embodiments, the present disclosure provides a use of SGD as an enzyme to catalytically convert strictosidine to form cathenamine and/or ajmalicine.

In at least one embodiment, SGD is a protein comprising the polypeptide sequence set forth in SEQ ID NO: 1 or a sequence substantially identical thereto.

In some embodiments, the present disclosure provides a use of GS as an enzyme to catalytically convert 4,21-dehydrogeissoschizine to form geissoschizine.

In at least one embodiment, GS is a protein comprising the polypeptide sequence set forth in any one of SEQ ID NO: 2; SEQ ID NO 37; SEQ ID NO 38; SEQ ID NO 39; or a sequence substantially identical thereto.

In some embodiments, the present disclosure provides a use of GS as an enzyme to catalytically convert 4,21-dehydrogeissoschizine to form pericyclivine and/or perivine.

In at least one embodiment, GS is a protein comprising the polypeptide sequence set forth in any one of SEQ ID NO: 2; SEQ ID NO 37; SEQ ID NO 38; SEQ ID NO 39; or a sequence substantially identical thereto.

In some embodiments, the present disclosure provides a use of GO as an enzyme to catalytically convert geissoschizine to form monooxygenated geissoschizine.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, the present disclosure provides a use of a mixture of enzymes comprising GO, REDOX 1, REDOX 2, SAT, and HL1 to catalytically convert geissoschizine to form catharanthine.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In at least one embodiment, HL1 is a protein comprising the polypeptide sequence set forth in any one of SEQ ID NO: 6 or a sequence substantially identical thereto.

In at least one embodiment, the present disclosure provides a use of a mixture of enzymes comprising GO, REDOX 1, REDOX 2, SAT, and HL2 to catalytically convert geissoschizine to form tabersonine.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In at least one embodiment, HL2 is a protein comprising the polypeptide sequence set forth in any one of SEQ ID NO: 7; SEQ ID NO: 52; SEQ ID NO: 53; SEQ ID NO: 54; SEQ ID NO 55; SEQ ID NO 56; or a sequence substantially identical thereto.

In at least one embodiment, the present disclosure provides a use of a mixture of enzymes comprising GO, REDOX 1, REDOX 2, and SAT to catalytically convert geissoschizine to form O-acetylstemmadenine.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In at least one embodiment, the present disclosure provides a use of a mixture of enzymes comprising GO, REDOX 1, and REDOX 2 to catalytically convert geissoschizine to form stemmadenine.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, the present disclosure provides a use of a mixture of enzymes comprising GO and REDOX 1 to catalytically convert geissoschizine to form MIA1 and/or MIA 2.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In some embodiments, the present disclosure provides a use of a mixture of enzymes comprising REDOX 1, REDOX 2, SAT and HL1 to catalytically convert monooxygenated geissoschizine to form catharanthine.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, HL1 is a protein comprising the polypeptide sequence set forth in any one of SEQ ID NO: 6 or a sequence substantially identical thereto.

In at least one embodiment, GS is a protein comprising the polypeptide sequence set forth in any one of SEQ ID NO: 2; SEQ ID NO 37; SEQ ID NO 38; SEQ ID NO 39; or a sequence substantially identical thereto.

In some embodiments, the present disclosure provides a use of a mixture of enzymes comprising REDOX1, REDOX 2, SAT and HL2 as an enzyme to catalytically convert monooxygenated geissoschizine to form tabersonine.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is a protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In at least one embodiment, HL2 is a protein comprising the polypeptide sequence set forth in any one of SEQ ID NO: 7; SEQ ID NO: 52; SEQ ID NO: 53; SEQ ID NO: 54; SEQ ID NO 55; SEQ ID NO 56; or a sequence substantially identical thereto.

In some embodiments, the present disclosure provides a use of REDOX 2 as an enzyme to catalytically convert geissoschizine to form isositsirikine.

In at least one embodiment, REDOX 2 is a protein comprising the polypeptide sequence set forth in any one of SEQ ID NO: 5; SEQ ID NO 46; SEQ ID NO 47; SEQ ID NO 48; or a sequence substantially identical thereto.

In some embodiments, the present disclosure provides a use of REDOX 1 as an enzyme to catalytically convert monooxygenated geissoschizine to form MIA1 and/or MIA2.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In some embodiments, the present disclosure provides a use of a mixture of enzymes comprising REDOX 1 and REDOX 2 to catalytically convert monooxygenated geissoschizine to form stemmadenine.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is a protein comprising the polypeptide sequence set forth in any one of SEQ ID NO: 5; SEQ ID NO 46; SEQ ID NO 47; SEQ ID NO 48; or a sequence substantially identical thereto.

In some embodiments, the present disclosure provides a use of a mixture of enzymes comprising REDOX 1, REDOX 2 and SAT to catalytically convert monooxygenated geissoschizine to form O-acetylstemmadenine.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is a protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In some embodiments, the present disclosure provides a use of SAT as enzymes to catalytically convert stemmadenine to form O-acetylstemmadenine.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In another aspect, the present disclosure provides in at least some embodiments uses of terpenoid indole alkaloid compounds, including strictosidine, 4,21-dehydrogeissoschizine, monooxygenated geissoschizine and geissoschizine.

In at least one embodiment, the present disclosure provides a use of strictosidine as a substrate for catalytic conversion to form 4,21-dehydrogeissoschizine in a reaction mixture comprising SGD.

In at least one embodiment, the present disclosure provides a use of 4,21-dehydrogeissoschizine as a substrate for catalytic conversion to form geissoschizine in a reaction mixture comprising GS.

In at least one embodiment, the present disclosure provides a use of geissoschizine as a substrate for catalytic conversion to form monooxygenated geissoschizine in a reaction mixture comprising GO.

In at least one embodiment, the present disclosure provides a use of monooxygenated geissoschizine as a substrate for catalytic conversion to form stemmadenine in a reaction mixture comprising REDOX 1 and REDOX 2.

In at least one embodiment, the present disclosure provides a use of monooxygenated geissoschizine as a substrate for catalytic conversion to form O-acetylstemmadenine in a reaction mixture comprising REDOX 1, REDOX 2 and SAT.

In at least one embodiment, the present disclosure provides a use of monooxygenated geissoschizine as a substrate for catalytic conversion to form catharanthine in a reaction mixture comprising REDOX 1, REDOX 2, SAT and HL1.

In at least one embodiment, the present disclosure provides a use of monooxygenated geissoschizine as a substrate for catalytic conversion to form tabersonine in a reaction mixture comprising REDOX 1, REDOX 2, SAT and HL2.

In at least one embodiment, the present disclosure provides a use of geissoschizine as a substrate for catalytic conversion to form catharanthine in a reaction mixture comprising GO, REDOX 1, REDOX 2, SAT and HL1.

In at least one embodiment, the present disclosure provides a use of geissoschizine as a substrate for catalytic conversion to form tabersonine in a reaction mixture comprising GO, REDOX 1, REDOX 2, SAT and HL2.

In at least one embodiment, the present disclosure provides a use of geissoschizine as a substrate for catalytic conversion to form O-acetylstemmadenine in a reaction mixture comprising GO, REDOX 1, REDOX 2, and SAT.

In at least one embodiment, the present disclosure provides a use of geissoschizine as a substrate for catalytic conversion to form stemmadenine in a reaction mixture comprising GO, REDOX 1, and REDOX 2.

In at least one embodiment, the present disclosure provides a use of geissoschizine as a substrate for catalytic conversion to form MIA 1 and/or MIA 2 in a reaction mixture comprising GO and REDOX 1.

In at least one embodiment, the present disclosure provides a use of geissoschizine as a substrate for catalytic conversion to form isositsirikine in a reaction mixture comprising REDOX 2.

In at least one embodiment, the present disclosure provides a use of monooxygenated geissoschizine as a substrate for catalytic conversion to form MIA1 and/or MIA2 in a reaction mixture comprising REDOX 1.

In another aspect the present disclosure provides methods of preparing a tabersonine-catharanthine synthesis derivatives from tabersonine-catharanthine synthesis intermediates In some embodiments, the present disclosure provides a method of preparing a tabersonine-catharanthine synthesis derivative, the method comprising:
  (a) providing a terpenoid indole alkaloid compound; and
  (b) contacting the terpenoid indole alkaloid compound with at least one of the enzymes selected from the group consisting of (i) SGD; (ii) GS; (iii) and GO, under reaction conditions permitting the catalysis of the terpenoid indole alkaloid compound to form a tabersonine-catharanthine synthesis intermediate; and
  (c) subjecting the tabersonine-catharanthine synthesis intermediate to reaction conditions that permit the conversion of the tabersonine-catharanthine synthesis intermediate to form a tabersonine-catharanthine synthesis derivative.

In at least some embodiments, the terpenoid indole alkaloid compound is selected from the group of terpenoid indole alkaloid compounds consisting of strictosidine, 4,21-dehydrogeissoschizine, geissoschizine and monooxygenated geissoschizine; and the tabersonine-catharanthine synthesis derivative is selected from the group of tabersonine-catharanthine synthesis derivatives consisting of cathenamine, ajmalicine, isositsirikine, pericyclivine, perivine, akuammicine, MIA1, MIA2, stemmadenine and O-acetylstemmadenine.

In another aspect, the present disclosure provides novel terpenoid indole alkaloid compounds.

In another aspect, the present disclosure provides polypeptides.

In at least one embodiment, the present disclosure provides a polypeptide comprising one or more of the polypeptide sequences set forth in SEQ ID NO: 1; SEQ ID NO: 2; SEQ ID NO: 3; SEQ ID NO: 4; SEQ ID NO: 5; SEQ ID NO: 6; and SEQ ID NO: 7; SEQ ID NO: 16; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; and SEQ ID NO: 56.

In another aspect, the present disclosure provides polynucleotides.

In at least one embodiment, the present disclosure provides a polynucleotide comprising one or more of the polynucleotide sequences set forth in SEQ ID NO: 8; SEQ ID NO: 9; SEQ ID NO: 10; SEQ ID NO: 11; SEQ ID NO: 12; SEQ ID NO: 13; SEQ ID. NO: 14; SEQ ID NO: 15; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; and SEQ ID NO: 36.

In another aspect, the present disclosure provides recombinant methods for preparing tabersonine, catharanthine, tabersonine-catharanthine synthesis intermediates, and tabersonine-catharanthine pathway precursor compounds.

The present disclosure provides in at least one embodiment, a method for preparing tabersonine, catharanthine, a tabersonine-catharanthine synthesis intermediate or a tabersonine-catharanthine synthesis derivative comprising:
(a) providing a chimeric nucleic acid sequence comprising as operably linked components:
  (i) one or more nucleic acid sequences encoding one or more of the polypeptides selected from the group of polypeptides consisting of SGD; GS; GO; REDOX 1; REDOX 2; SAT; HL1; and HL2; and
  (ii) one or more nucleic acid sequences capable of controlling expression in a host cell;
(b) introducing the chimeric nucleic acid sequence into a host cell and growing the host cell to produce the polypeptide selected from the group of polypeptides consisting of SGD; GS; GO; REDOX 1; REDOX 2; SAT; HL1; and HL2 and to produce one or more of tabersonine, catharanthine, the tabersonine-catharanthine synthesis intermediate, or the tabersonine-catharanthine synthesis derivative; and
(c) recovering tabersonine, catharanthine, the tabersonine-catharanthine synthesis intermediate, or the tabersonine-catharanthine synthesis derivative.

In some embodiments, the tabersonine-catharanthine synthesis intermediate is selected from the group consisting of monooxygenated geissoschizine; geissoschizine; 4,21-dehydrogeissoschizine; and strictosidine.

In some embodiments, the tabersonine-catharanthine synthesis derivative is selected from the group consisting of cathenamine, ajmalicine, isositsirikine, pericyclivine, perivine, akuammicine, MIA1, MIA2, stemmadenine and O-acetylstemmadenine.

In at least one embodiment, SGD is a protein comprising the polypeptide sequence set forth in SEQ ID NO: 1 or a sequence substantially identical thereto.

In at least one embodiment, GS is a protein comprising the polypeptide sequence set forth in any one of SEQ ID NO: 2; SEQ ID NO 37; SEQ ID NO 38; SEQ ID NO 39; or a sequence substantially identical thereto.

In at least one embodiment, GO is a protein comprising the polypeptide sequence set forth in any one of SEQ ID NO: 3; SEQ ID NO 40; SEQ ID NO 41; SEQ ID NO 42; or a sequence substantially identical thereto.

In at least one embodiment, REDOX 1 is a protein comprising the polypeptide sequence set forth in any one of SEQ ID NO: 4; SEQ ID NO 43; SEQ ID NO 44; SEQ ID NO 45; or a sequence substantially identical thereto.

In at least one embodiment, REDOX 2 is a protein comprising the polypeptide sequence set forth in any one of SEQ ID NO: 5; SEQ ID NO 46; SEQ ID NO 47; SEQ ID NO 48; or a sequence substantially identical thereto.

In at least one embodiment, SAT is a protein comprising the polypeptide sequence set forth in any one of SEQ ID NO: 16; SEQ ID NO 49; SEQ ID NO 50; SEQ ID NO 51; or a sequence substantially identical thereto.

In at least one embodiment, HL1 is a protein comprising the polypeptide sequence set forth in any one of SEQ ID NO: 6 or a sequence substantially identical thereto.

In at least one embodiment, HL2 is a protein comprising the polypeptide sequence set forth in any one of SEQ ID NO: 7; SEQ ID NO: 52; SEQ ID NO: 53; SEQ ID NO: 54; SEQ ID NO 55; SEQ ID NO 56; or a sequence substantially identical thereto.

The present disclosure provides in at least one embodiment, a method for preparing a tabersonine-catharanthine pathway precursor compound selected from the group of tabersonine-catharanthine precursor compounds consisting of monooxygenated geissoschizine, geissoschizine, 4,21-dehydrogeissoschizine and strictosidine comprising:
(a) providing a chimeric nucleic acid sequence comprising (i) one or more nucleic acid sequences complementary to all or a portion of the mRNA synthesized by the nucleic acid sequence encoding the polypeptides selected from the group of polypeptides consisting of SGD; GS; GO; REDOX 1; REDOX 2; SAT; HL1; and HL2; and (ii) one or more elements capable of controlling transcription of the complementary nucleic acid sequence, wherein the chimeric nucleic acid sequence is capable of producing an antisense RNA complementary to all or a portion of the mRNA of the nucleic acid sequence encoding the polypeptides selected from the group of polypeptides consisting of SGD; GS; GO; REDOX 1; REDOX 2; SAT; HL1; and HL2;
(b) introducing the chimeric nucleic acid sequence into a host cell;
(c) growing the host cell to produce the antisense RNA and inhibit synthesis of the polypeptide selected from the group of polypeptides consisting of SGD; GS; GO; REDOX 1; REDOX 2; SAT: HL1; and HL2, and to produce one or more tabersonine-catharanthine pathway precursor compounds selected from the group of tabersonine-catharanthine pathway precursor compounds consisting of monooxygenated geissoschizine, geissoschizine, 4,21-dehydrogeissoschizine and strictosidine; and (d) recovering tabersonine-catharanthine pathway precursor compound selected from the group of tabersonine-catharanthine pathway precursor compounds consisting of monooxygenated geissoschizine, geissoschizine, 4,21-dehydrogeissoschizine and strictosidine.

In another aspect, the present disclosure provides recombinant expression vectors useful in the production of tabersonine, catharanthine, a tabersonine-catharanthine synthesis intermediate.

In some embodiments, the present disclosure provides a recombinant expression vector comprising in the 5' to 3' direction of transcription as operably linked components:
(i) a polynucleotide capable of controlling expression in a host cell; and (ii) a polynucleotide encoding SGD; GS; GO; REDOX 1; REDOX 2; SAT; HL1; and/or HL2.

In yet another embodiment, the present disclosure provides a host cell comprising the recombinant expression vector.

In some embodiments, the cell is a plant cell or an algal cell.

In some embodiments, the cell is a microbial cell.

In at least some embodiments, the host cell is selected from the group consisting of *Catharanthus roseus, Lonerica japonica, Vinca minor, Amsonia hubrichtii* and *Tabernaemontana elegans*.

In at least some embodiments, the microbial cell is selected from the group consisting of *Escherichia coli, Saccharomyces cerevisiae* and *Yarrowia liplytica*.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

FIG. 1 depicts certain chemical compounds or moieties relating to the chemical constituency of terpenoid indole alkaloid compounds, notably, indole (FIG. 1A), a terpene moiety (FIG. 1B) and geraniol (FIG. 1C).

FIG. 4 depicts the synthesis of vindoline from tabersonine (FIG. 4A) and the synthesis of vincristine and vinblastine from vindoline and catharanthine. (FIG. 4B)

FIG. 13 depicts results obtained in certain experiments designed to evaluate silencing of the nucleic acid sequence encoding GO. Shown are an LC profile of leaf surface alkaloids of control plants (EV) and VIGS-GO plants at 280 nm (FIG. 13A); an LC profile of leaf body alkaloids of control plants (EV) and VIGS-GO plants at 300 nm (FIG. 13B); the transcripts level of GO in the leaves of the empty vector control plants (EV) and the VIGS-GO plants (FIG. 13C); the alkaloid constituents in the EV plants and the VIGS-GO plants (FIG. 13D).

(FIG. 14A); an LC profile of leaf body alkaloids of control plants (EV) and VIGS-REDOX 1 plants at 300 nm (FIG. 14B); The relative transcripts level of REDOX 1 in the leaves of the empty vector control plants (EV) and the VIGS-REDOX 1 plants (FIG. 14C); the alkaloid contents in the EV plants and the VIGS-REDOX 1 plants (FIG. 14D); an LC chromatogram of monooxygenated geissoschizine non-treated control (FIG. 14F); and LC chromatogram of monooxygenated geissoschizine dissolved in chloroform at room temperature for 1 h (FIG. 14E). Monooxygenated geissoschizine and akuammicine are shown at UV 280 nm and 330 nm, respectively (FIGS. 14E and 14F). Spontaneous conversion of monooxygenated geissoschizine to akuammicine is observed (FIGS. 14 E and 14F).

FIG. 16 depicts results obtained in certain experiments designed to evaluate silencing of the nucleic acid sequence encoding HL1 and HL2. Shown is an LC profile of leaf total alkaloids of control plants (EV) and VIGS-HL1 or -HL2 plants at 280 nm (FIG. 16A); the relative transcripts level of HL1/2 in the leaves of the empty vector control plants (EV) and the VIGS-HL1/2 plants (FIG. 16 B); the alkaloid constituents in the EV plants and the VIGS-HL1/2 plants (FIG. 16C).

Figure 2:
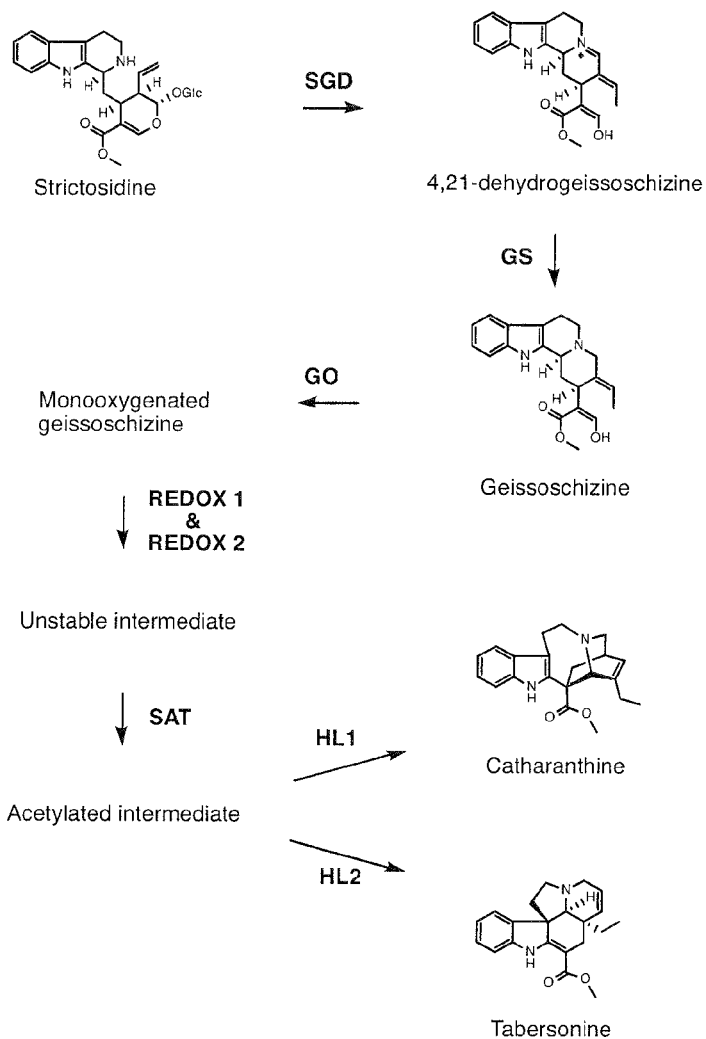
FIG. 2 depicts a synthesis pathway for the manufacture of tabersonine and catharanthine and synthesis intermediates thereof. Included are the chemical structures of the synthesis intermediates and the enzymes capable of catalyzing chemical conversion of the synthesis intermediates.

The drawings together with the following detailed description make apparent to those skilled in the art how the disclosure may be implemented in practice.

DETAILED DESCRIPTION OF THE DISCLOSURE

Various compositions, systems processes and methods will be described below to provide an example of an embodiment of each claimed subject matter. No embodiment described below limits any claimed subject matter and any claimed subject matter may cover compositions, systems processes and methods that differ from those described below. The claimed subject matter is not limited to compositions, systems processes and methods having all of the features of any one composition, system, process or method described below or to features common to multiple or all of the compositions, systems, methods or processes described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents and patent applications referred herein are herein incorporated by reference in their entirety to the same extent as if each individual publication, patent or patent application was specifically and individually indicated to be incorporated by reference in its entirety.

Definitions

As used herein, each of the following terms has the meaning associated with it in this section.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The articles "a" and "an" are used herein to refer to one or to more than one (i.e., to at least one) of the grammatical object of the article. By way of example, "an element" means one element or more than one element.

The terms "terpenoid indole alkaloid" and "terpenoid indole alkaloid compound", which may be used interchangeably herein, refer to a class of chemical compounds comprising an indole moiety (FIG. 1A) and a terpenoid, i.e. a compound having a terpene moiety (FIG. 1B). An example of a terpenoid is geraniol (FIG. 1C). Further examples of terpenoids include, but are not limited to, geraniol derivatives such as 10-hydrogeraniol, loganin and secologanin The term "tabersonine", as used herein, refers to a chemical compound having the structural formula depicted in FIG. 3A.

Figure 3:
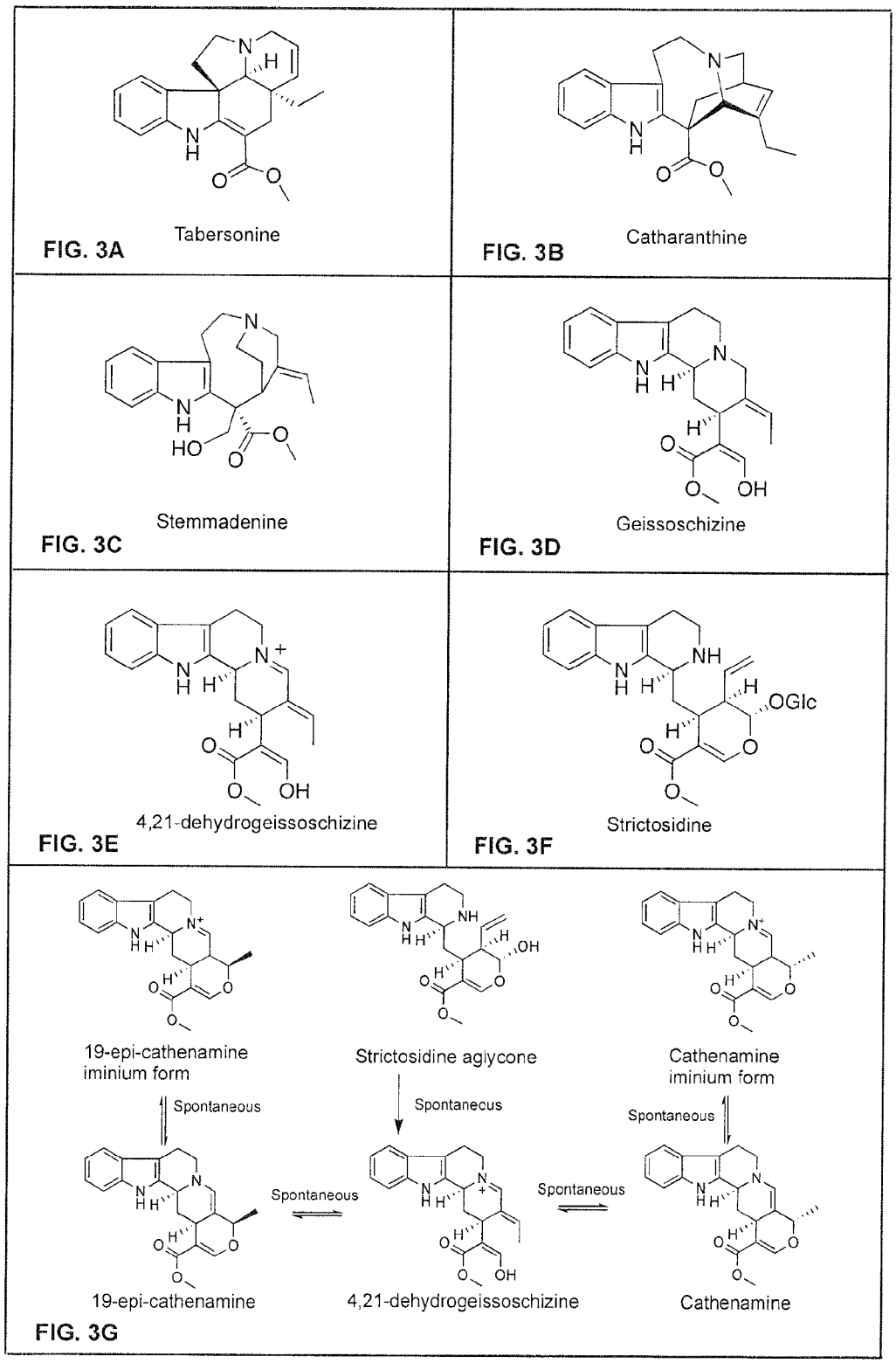
FIG. 3 depicts the chemical structures of certain terpenoid indole alkaloid compounds, notably tabersonine (FIG. 3A), catharanthine (FIG. 3B), stemmadenine (FIG. 3C), geissoschizine (FIG. 3D), 4,21-dehydrogeissoschizine (FIG. 3E), strictosidine (FIG. 3F) and strictosidine aglycone and strictosidine aglycone derivatives (FIG. 3G).

The term "catharanthine", as used herein, refers to a chemical compound having the structural formula depicted in FIG. 3B.

The term "stemmadenine", as used herein, refers to a chemical compound having the structural formula depicted in FIG. 3C.

The term "geissoschizine", as used herein, refers to a chemical compound having the structural formula depicted in FIG. 3D.

The term "4,21-dehydrogeissoschizine", as used herein, refers to a chemical compound having the structural formula depicted in FIG. 3E.

The term "strictosidine", as used herein, refers to a chemical compound having the structural formula depicted in FIG. 3F.

The term "strictosidine aglycone", as used herein, refers to a chemical compound having the structural formula depicted and so denoted in FIG. 3G. It is noted that strictosidine aglycone can spontaneously convert to 4,21-dehydrogeissoschizine which in turn can exist in chemical equilibrium with the derivative compounds cathenamine, cathenamine (iminium form), 19-epi-cathenamine and 19-epi-cathenamine (iminium form), as depicted in FIG.

3G). Together cathenamine, cathenamine (iminium form), 19-epi-cathenamine and 19-epi-cathenamine (iminium form) may be referred herein as "strictosidine aglycone derivatives".

The term "monooxygenated geissoschizine" refers to a monooxygenated form of geissoschizine.

The term "cathenamine", as used herein, refers to a chemical compound having the structural formula depicted in FIG. 18A.

The term "ajmalicine", as used herein, refers to a chemical compound having the structural formula depicted in FIG. 18B.

The term "isositsirikine", as used herein, refers to a chemical compound having the structural formula depicted in FIG. 18C.

The term "pericyclivine", as used herein, refers to a chemical compound having the structural formula depicted in FIG. 18D.

The term "perivine", as used herein, refers to a chemical compound having the structural formula depicted in FIG. 18E.

The term "akuammicine", as used herein, refers to a chemical compound having the structural formula depicted in FIG. 18F.

The terms "16S-desformylstemmadenine" and "MIA1", as may be used herein interchangeably, refer to a chemical compound having the structural formula depicted in FIG. 18G.

The terms "16R-desformylstemmadenine" and "MIA2", as may be used herein interchangeably, refer to a chemical compound having the structural formula depicted in FIG. 18H.

The term "O-acetylstemmadenine", as used herein, refers to the chemical compound depicted in FIG. 18I.

The terms "tabersonine-catharanthine pathway" or "tabersonine-catharanthine synthesis pathway", as may be used interchangeably herein, refer to the metabolic pathway for the synthesis of tabersonine and catharanthine depicted in FIG. 2. When a first chemical compound within the tabersonine-catharanthine pathway is referenced as "upstream" of a second chemical compound in the pathway, it meant herein that synthesis of the first chemical compound precedes synthesis of the second chemical compound. Conversely, when a first chemical compound is referenced as "downstream" from the second chemical compound in the tabersonine-catharanthine pathway, it is meant herein that synthesis of the second chemical compound precedes synthesis of the first chemical compound.

The terms "tabersonine-catharanthine precursor" or tabersonine-catharanthine pathway precursor compound", as may be interchangeably used herein, refer to any of the chemical compounds in the tabersonine-catharanthine pathway synthesis pathway set forth in FIG. 3D; FIG. 3E; and FIG. 3F and further includes monooxygenated geissoschizine; in conjunction with the term tabersonine-catharanthine synthesis intermediate, tabersonine-catharanthine pathway precursor refers to a compound synthesized upstream of a tabersonine-catharanthine intermediate.

The term "tabersonine-catharanthine pathway precursor derivative", as used herein, refers to a chemical compound derived or derivable from any of the compounds in the tabersonine-catharanthine pathway synthesis pathway set forth in FIG. 3D; FIG. 3E; FIG. 3F; and monooxygenated geissoschizine, and includes, without limitation, strictosidine aglycone and strictosidine aglycone derivatives (FIG. 3G), but excluding any of the compounds set forth in FIG. 3D-FIG. 3F and excluding monooxygenated geissoschizine, wherein such derivative compound is capable of acting as a precursor compound to form a tabersonine-catharanthine pathway precursor or a tabersonine-catharanthine pathway intermediate.

The term "tabersonine-catharanthine synthesis intermediate", as used herein, refers to any of the chemical compounds in the tabersonine-catharanthine synthesis pathway set forth in FIG. 3D; and FIG. 3E; and further includes monooxygenated geissoschizine; in conjunction with the term tabersonine-catharanthine pathway precursor compound, tabersonine-catharanthine synthesis intermediate refers to a compound synthesized downstream of a tabersonine-catharanthine pathway precursor compound.

The term "tabersonine-catharanthine synthesis derivative", as used herein, refers to any chemical compound that may be derivatized from a tabersonine-catharanthine synthesis intermediate obtained by synthesis via one or more synthesis steps within the tabersonine-catharanthine pathway, including, without limitation, cathenamine, ajmalicine, isositsirikine, pericyclivine, perivine, akuammicine, MIA1, MIA2, stemmadenine and O-acetylstemmadenine, but excluding the compounds set forth in FIG. 3A-FIG. 3B and FIG. 3D-FIG. 3G, and excluding monooxygenated geissoschizine.

The term "catalytic quantities", as used herein, refers to quantities of an enzyme that are sufficient to effect enzyme mediated catalysis of a substrate to form a product. Catalytic quantities of enzymes can be quantities as low as less than about 1% (w/w), less than about 0.5% (w/w), less than about 0.1% (w/w), less than about 0.05% (w/w), or less than about 0.01% (w/w) within a reaction mixture.

The terms "SGD" and "strictosidine β-glucosidase", as may be used interchangeably herein, refer to any and all enzymes comprising a sequence of amino acid residues which is (i) substantially identical to the amino acid sequences constituting any SGD polypeptide set forth herein, including, for example, SEQ ID NO: 1, or (ii) encoded by a nucleic acid sequence capable of hybridizing under at least moderately stringent conditions to any nucleic acid sequence encoding any SGD polypeptide set forth herein, but for the use of synonymous codons.

The terms "GS" and "geissoschizine synthase", as may be used interchangeably herein, refer to any and all enzymes comprising a sequence of amino acid residues which is (i) substantially identical to the amino acid sequences constituting any GS polypeptide set forth herein, including, for example, SEQ ID NO: 2, or (ii) encoded by a nucleic acid sequence capable of hybridizing under at least moderately stringent conditions to any nucleic acid sequence encoding any GS polypeptide set forth herein, but for the use of synonymous codons.

The terms "GO" and geissoschizine oxidase", as may be used interchangeably herein, refer to any and all enzymes comprising a sequence of amino acid residues which is (i) substantially identical to the amino acid sequences constituting any AT1 polypeptide set forth herein, including, for example, SEQ ID NO: 3, or (ii) encoded by a nucleic acid sequence capable of hybridizing under at least moderately stringent conditions to any nucleic acid sequence encoding any GO polypeptide set forth herein, but for the use of synonymous codons.

The terms "REDOX 1" and "reductase 1", as may be used interchangeably herein, refer to any and all enzymes comprising a sequence of amino acid residues which is (i) substantially identical to the amino acid sequences constituting any REDOX 1 polypeptide set forth herein, including, for example, SEQ ID NO: 4, or (ii) encoded by a nucleic acid sequence capable of hybridizing under at least moderately stringent conditions to any nucleic acid sequence encoding any REDOX 1 polypeptide set forth herein, but for the use of synonymous codons.

The terms "REDOX 2" and "reductase 2", as may be used interchangeably herein, refer to any and all enzymes comprising a sequence of amino acid residues which is (i) substantially identical to the amino acid sequences constituting any REDOX 2 polypeptide set forth herein, including, for example, SEQ ID NO: 5, or (ii) encoded by a nucleic acid sequence capable of hybridizing under at least moderately stringent conditions to any nucleic acid sequence encoding any REDOX 2 polypeptide set forth herein, but for the use of synonymous codons.

The terms "HL1" and "hydrolase 1", as may be used interchangeably herein, refer to any and all enzymes comprising a sequence of amino acid residues which is (i) substantially identical to the amino acid sequences constituting any HL1 polypeptide set forth herein, including, for example, SEQ ID NO: 6, or (ii) encoded by a nucleic acid sequence capable of hybridizing under at least moderately stringent conditions to any nucleic acid sequence encoding any HL1 polypeptide set forth herein, but for the use of synonymous codons.

The term "HL2" and "hydrolase 2", as may be used interchangeably herein, refer to any and all enzymes comprising a sequence of amino acid residues which is (i) substantially identical to the amino acid sequences constituting any HL2 polypeptide set forth herein, including, for example, SEQ ID NO: 7, or (ii) encoded by a nucleic acid sequence capable of hybridizing under at least moderately stringent conditions to any nucleic acid sequence encoding any HL2 polypeptide set forth herein, but for the use of synonymous codons.

The term "SAT" and "stemmadenine acetyl transferase", as may be used interchangeably herein, refer to any and all enzymes comprising a sequence of amino acid residues which is (i) substantially identical to the amino acid sequences constituting any SAT polypeptide set forth herein, including, for example, SEQ ID NO: 16, or (ii) encoded by a nucleic acid sequence capable of hybridizing under at least moderately stringent conditions to any nucleic acid sequence encoding any SAT polypeptide set forth herein, but for the use of synonymous codons.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The herein interchangeably used terms "nucleic acid sequence encoding SGD" and "nucleic acid sequence encoding a SGD polypeptide", refer to any and all nucleic acid sequences encoding an SGD polypeptide, including SEQ ID NO: 8. Nucleic acid sequences encoding an SGD polypeptide further include any and all nucleic acid sequences which (i) encode polypeptides that are substantially identical to the SGD polypeptide sequences set forth herein; or (ii) hybridize to any SGD nucleic acid sequences set forth herein under at least moderately stringent hybridization conditions or which would hybridize thereto under at least moderately stringent conditions but for the use of synonymous codons.

The herein interchangeably used terms "nucleic acid sequence encoding GS" and "nucleic acid sequence encoding a GS polypeptide", refer to any and all nucleic acid sequences encoding a GS polypeptide, including, for example, SEQ ID NO: 9. Nucleic acid sequences encoding a GS polypeptide further include any and all nucleic acid sequences which (i) encode polypeptides that are substantially identical to the GS polypeptide sequences set forth herein; or (ii) hybridize to any GS nucleic acid sequences set forth herein under at least moderately stringent hybridization conditions or which would hybridize thereto under at least moderately stringent conditions but for the use of synonymous codons.

The herein interchangeably used terms "nucleic acid sequence encoding GO" and "nucleic acid sequence encoding a GO polypeptide", refer to any and all nucleic acid sequences encoding a GO polypeptide, including, for example, SEQ ID NO: 10. Nucleic acid sequences encoding a GO polypeptide further include any and all nucleic acid sequences which (i) encode polypeptides that are substantially identical to the GO polypeptide sequences set forth herein; or (ii) hybridize to any GO nucleic acid sequences set forth herein under at least moderately stringent hybridization conditions or which would hybridize thereto under at least moderately stringent conditions but for the use of synonymous codons.

The herein interchangeably used terms "nucleic acid sequence encoding REDOX 1" and "nucleic acid sequence encoding a REDOX 1 polypeptide", refer to any and all nucleic acid sequences encoding a REDOX 1 polypeptide, including, for example, SEQ ID NO: 11. Nucleic acid sequences encoding a REDOX 1 polypeptide further include any and all nucleic acid sequences which (i) encode polypeptides that are substantially identical to the REDOX 1 polypeptide sequences set forth herein; or (ii) hybridize to any REDOX 1 nucleic acid sequences set forth herein under at least moderately stringent hybridization conditions or which would hybridize thereto under at least moderately stringent conditions but for the use of synonymous codons.

The herein interchangeably used terms "nucleic acid sequence encoding REDOX 2" and "nucleic acid sequence encoding a REDOX 2 polypeptide", refer to any and all nucleic acid sequences encoding a REDOX 2 polypeptide, including, for example, SEQ ID NO: 12. Nucleic acid sequences encoding a REDOX 2 polypeptide further include any and all nucleic acid sequences which (i) encode polypeptides that are substantially identical to the REDOX 2 polypeptide sequences set forth herein; or (ii) hybridize to any REDOX 2 nucleic acid sequences set forth herein under at least moderately stringent hybridization conditions or which would hybridize thereto under at least moderately stringent conditions but for the use of synonymous codons.

The herein interchangeably used terms "nucleic acid sequence encoding HL1" and "nucleic acid sequence encoding an HL1 polypeptide", refer to any and all nucleic acid sequences encoding an HL1 polypeptide, including, for example, SEQ ID NO: 13. Nucleic acid sequences encoding an HL1 polypeptide further include any and all nucleic acid sequences which (i) encode polypeptides that are substantially identical to the HL1 polypeptide sequences set forth herein; or (ii) hybridize to any HL1 nucleic acid sequences set forth herein under at least moderately stringent hybridization conditions or which would hybridize thereto under at least moderately stringent conditions but for the use of synonymous codons.

The herein interchangeably used terms "nucleic acid sequence encoding HL2" and "nucleic acid sequence encoding an HL2 polypeptide", refer to any and all nucleic acid sequences encoding an polypeptide, including, for example, SEQ ID NO: 14. Nucleic acid sequences encoding an HL2 polypeptide further include any and all nucleic acid sequences which (i) encode polypeptides that are substantially identical to the HL2 polypeptide sequences set forth herein; or (ii) hybridize to any HL2 nucleic acid sequences set forth herein under at least moderately stringent hybridization conditions or which would hybridize thereto under at least moderately stringent conditions but for the use of synonymous codons.

The herein interchangeably used terms "nucleic acid sequence encoding SAT" and "nucleic acid sequence encoding an SAT polypeptide", refer to any and all nucleic acid sequences encoding an polypeptide, including, for example, SEQ ID NO: 15. Nucleic acid sequences encoding an SAT polypeptide further include any and all nucleic acid sequences which (i) encode polypeptides that are substantially identical to the HL2 polypeptide sequences set forth herein; or (ii) hybridize to any SAT nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (*J. Mol. Biol.*, 1970, 48: 443), as revised by Smith and Waterman (*Adv. Appl. Math.*, 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (*SIAM J. Applied Math.*, 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., *Nucleic Acids Res*, 1984, 12: 387) BLASTP, BLASTN and FASTA (Altschul et al., *J. Mol. Biol.*, 1990:215:403). A particularly preferred method for determining the percentage identity between two polypeptides involves the Clustal W algorithm (Thompson, J D, Higgines, D G and Gibson T J, 1994, *Nucleic Acids Res* 22(22): 4673-4680 together with the BLOSUM 62 scoring matrix (Henikoff S & Henikoff, J G, 1992, *Proc. Natl. Acad. Sci. USA* 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation)−5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "chimeric" as used herein in the context of nucleic acid sequences refers to at least two linked nucleic acid sequences, which are not naturally linked. Chimeric nucleic acid sequences include linked nucleic acid sequences of different natural origins. For example a nucleic acid sequence constituting a yeast promoter linked to a nucleic acid sequence encoding a HL1 protein is considered chimeric. Chimeric nucleic acid sequences also may comprise nucleic acid sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences also include nucleic acid sequences comprising any naturally occurring nucleic acid sequence linked to any non-naturally occurring nucleic acid sequence.

The terms "substantially pure" and "isolated", as may be used interchangeably herein describe a compound, e.g., a pathway synthesis intermediate or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "in vivo" as used herein to describe methods of making catharanthine or tabersonine or tabersonine-catharanthine synthesis intermediates or tabersonine-catharanthine synthesis derivatives refers to contacting a tabersonine-catharanthine pathway precursor compound with an enzyme capable of catalyzing conversion of a tabersonine-catharanthine precursor within a living cell, including, without limitation, for example, a microbial cell or a plant cell, to form catharanthine or tabersonine or tabersonine-catharanthine synthesis intermediates or tabersonine-catharanthine synthesis derivatives.

The term "in vitro" as used herein to describe methods of making catharanthine or tabersonine or tabersonine-catharanthine synthesis intermediates or tabersonine-catharanthine synthesis derivatives refers to contacting a tabersonine-catharanthine pathway precursor compound with an enzyme capable of catalyzing conversion of a tabersonine-catharanthine precursor in an environment outside a living cell, including, without limitation, for example, in a microwell plate, a tube, a flask, a beaker, a tank, a reactor and the like, to form catharanthine or tabersonine or tabersonine-catharanthine synthesis intermediates or tabersonine-catharanthine synthesis derivatives.

General Implementation

As hereinbefore mentioned, the present application provides methods for making terpenoid indole alkaloids, including tabersonine and catharanthine and synthesis intermediates thereof. The present disclosure further relates to certain enzymes capable of catalyzing reactions resulting in the chemical conversion of tabersonine-catharanthine pathway precursor compounds, tabersonine-catharanthine precursor derivative compounds and tabersonine-catharanthine pathway intermediates to form tabersonine and/or catharanthine. The herein provided methods represent a novel and efficient means of manufacturing tabersonine and catharanthine and tabersonine-catharanthine synthesis intermediates and tabersonine-catharanthine synthesis derivatives. The methods provided herein do not rely on chemical synthesis and may be conducted at commercial scale. To the best of the inventors' knowledge, the current disclosure provides, for the first time, a methodology to manufacture tabersonine and catharanthine using living cells not normally capable of synthesizing tabersonine and catharanthine. Such cells may be used as a source whence tabersonine and catharanthine may economically be extracted. Tabersonine and catharanthine produced in accordance with the present disclosure is useful inter alia in the manufacture of pharmaceutical compositions for the treatment of cancer, notably vincristine and vinblastine.

Accordingly, the present disclosure provides in one aspect, in at least one embodiment, a method of making tabersonine, catharanthine a synthesis intermediate thereof or a synthesis derivative thereof comprising:
  (a) providing a terpenoid indole alkaloid compound; and
  (b) contacting the terpenoid indole alkaloid compound with at least one of the enzymes selected from the group consisting of (i) SGD; (ii) GS; (iii) GO; (iv) REDOX 1; (v) REDOX 2; (vi) SAT; (vii) HL1; and (viii) HL2 under reaction conditions permitting the catalysis of the terpenoid indole alkaloid compound to form tabersonine, catharanthine or a synthesis intermediate thereof.

In accordance herewith, preferred tabersonine-catharanthine intermediates are selected from the group consisting of 4,21-dehydrogeissoschizine; geissoschizine; and monooxygenated geissoschizine. Furthermore in accordance herewith, the terpenoid indole alkaloid compound is preferably a tabersonine-catharanthine pathway precursor compound, notably strictosidine; 4,21-dehydrogeissoschizine; geissoschizine; or monooxygenated geissoschizine; or in another preferred embodiment, a tabersonine-catharanthine pathway precursor derivative compound, notably strictosidine aglycone or a strictosidine aglycone derivative.

In certain embodiments, at least two, at least three, at least four, at least five, at least six, or at least seven of the enzymes are selected from the group consisting of (i) SGD; (ii) GS; (iii) GO; (iv) REDOX 1; (v) REDOX 2; (vi) SAT; (vii) HL1; and (viii) HL2 are contacted with the terpenoid indole alkaloid compound.

The present disclosure provides, in one aspect, in a least one embodiment a method of making tabersonine or catharanthine or a synthesis intermediate thereof comprising:
  (a) providing a tabersonine-catharanthine pathway precursor compound or a tabersonine-catharanthine pathway precursor derivative compound; and
  (b) contacting the tabersonine-catharanthine pathway precursor compound or tabersonine-catharanthine pathway precursor derivative compound with at least one of the enzymes selected from the group consisting of (i) SGD; (ii) GS; (iii) GO; (iv) REDOX 1; (v) REDOX 2; (vi) SAT; (vii) HL1 and (viii) HL2 under reaction conditions permitting the catalysis of the tabersonine-catharanthine pathway precursor compound or tabersonine-catharanthine pathway precursor derivative compound to form tabersonine or catharanthine or a synthesis intermediate thereof;
wherein the tabersonine-catharanthine pathway precursor compound is strictosidine; 4,21-dehydrogeissoschizine; geissoschizine; or monooxygenated geissoschizine;
wherein the tabersonine-catharanthine pathway precursor derivative compound is strictosidine aglycone or a strictosidine aglycone derivative; and
wherein the synthesis intermediate is 4,21-dehydrogeissoschizine; geissoschizine; or monooxygenated geissoschizine.

It is noted that in any embodiments set forth herein wherein strictosidine aglycone derivatives are provided to perform a method in accordance with the present disclosure, such strictosidine aglycone derivatives may be provided in a form wherein such strictosidine aglycone derivative is substantially free of other strictosidine aglycone derivatives, or in the form of a mixture comprising two or more of the following strictosidine aglycone derivatives cathenamine, cathenamine (iminium form), 19-epi-cathenamine and 19-epi-cathenamine (iminium form). Mixtures or strictosidine aglycone derivatives substantially free of other strictosidine aglycones additionally can comprise 4,21-dehydrogeissoschizine and/or strictosidine aglycone. The relative quantities of each of the foregoing compounds may vary.

In embodiments set forth herein wherein strictosidine aglycone is provided to conduct a method in accordance of the present disclosure, strictosidine aglycone can be provided substantially free of strictosidine aglycone derivatives, or in the form of a mixture with one or more of cathenamine, cathenamine (iminium form), 19-epi-cathenamine and 19-epi-cathenamine (iminium form), and can further additionally comprise 4,21-dehydrogeissoschizine.

Herein after a variety of example embodiments of these methods will be further described.

Tabersonine Synthesis

In one example embodiment of the disclosure, there is provided a method of making tabersonine, the method comprising:
  (a) providing strictosidine; and
  (b) contacting strictosidine with a mixture of enzymes comprising catalytic quantities of (i) SGD; (ii) GS; (iii) GO; (iv) REDOX 1; (v) REDOX 2; (vi) SAT and (vii) HL2 under reaction conditions permitting the catalytic conversion of strictosidine to form tabersonine.

In one example embodiment of the disclosure, there is provided a method of making tabersonine, the method comprising:
(a) providing strictosidine aglycone or a strictosidine aglycone derivative; and
(b) contacting strictosidine aglycone or the strictosidine aglycone derivative with a mixture of enzymes comprising catalytic quantities of (i) GS; (ii) GO; (iii) REDOX 1; (iv) REDOX 2; (v) SAT; and (vi) HL2 under reaction conditions permitting the catalytic conversion of strictosidine aglycone or the strictosidine aglycone derivative to form tabersonine.

In one example embodiment of the disclosure, there is provided a method of making tabersonine, the method comprising:
(a) providing 4,21-dehydrogeissoschizine; and
(b) contacting 4,21-dehydrogeissoschizine with a mixture of enzymes comprising catalytic quantities of (i) GS; (ii) GO; (iii) REDOX 1: (iv) REDOX 2; (v) SAT and (vi) HL2 under reaction conditions permitting the catalytic conversion of 4,21-dehydrogeissoschizine to form tabersonine.

In one example embodiment of the disclosure, there is provided a method of making tabersonine, the method comprising:
(a) providing geissoschizine; and
(b) contacting geissoschizine with a mixture of enzymes comprising catalytic quantities of [i] GO; (ii) REDOX 1; (iii) REDOX 2; (iv) SAT and (v) HL2 under reaction conditions permitting the catalytic conversion of geissoschizine to form tabersonine.

In one example embodiment of the disclosure, there is provided a method of making tabersonine, the method comprising:
(a) providing monooxygenated geissoschizine; and
(b) contacting monooxygenated geissoschizine with a mixture of enzymes comprising catalytic quantities of (i) REDOX 1; (ii) REDOX 2; (iii) SAT and (iv) HL2 under reaction conditions permitting the catalytic conversion of monooxygenated geissoschizine to form tabersonine.

The foregoing embodiments of the disclosure to make tabersonine are further illustrated in Table A.

The foregoing methods may be performed under in vivo conditions or under in vitro conditions as hereinafter detailed.

Catharanthine Synthesis

In one example embodiment of the disclosure, there is provided a method of making catharanthine, the method comprising:
(a) providing strictosidine; and
(b) contacting strictosidine with a mixture of enzymes comprising catalytic quantities of (i) SGD; (ii) GS; (iii) GO; (iv) REDOX 1; (v) REDOX 2; (vi) SAT and (vii) HL1 under reaction conditions permitting the catalytic conversion of strictosidine to form catharanthine.

In one example embodiment of the disclosure, there is provided a method of making catharanthine, the method comprising:
(a) providing strictosidine aglycone or a strictosidone aglycone derivative; and
(b) contacting strictosidine aglycone or the strictosidone aglycone derivative with a mixture of enzymes comprising catalytic quantities of (i) GS; (ii) GO; (iii) REDOX 1; (iv) REDOX 2; (v) SAT; and (vi) HL1 under reaction conditions permitting the catalytic conversion of strictosidine aglycone or the strictosidine aglycone derivative to form catharanthine.

In one example embodiment of the disclosure, there is provided a method of making catharanthine, the method comprising:
(a) providing 4,21-dehydrogeissoschizine; and
(b) contacting 4,21-dehydrogeissoschizine with a mixture of enzymes comprising catalytic quantities of (i) GS; (ii) GO; (iii) REDOX 1; (v) REDOX 2; (vi) SAT; and (vi) HL1 under reaction conditions permitting the catalytic conversion of 4,21-dehydrogeissoschizine to form catharanthine.

In one exemplary embodiment of the disclosure, there is provided a method of making catharanthine, the method comprising:
(a) providing geissoschizine; and
(b) contacting geissoschizine with a mixture of enzymes comprising catalytic quantities of (i) GO; (ii) REDOX 1; (iii) REDOX 2; (iv) SAT and (v) HL1 under reaction conditions permitting the catalytic conversion of geissoschizine to form catharanthine.

In one exemplary embodiment of the disclosure, there is provided a method of making catharanthine, the method comprising:
(a) providing monooxygenated geissoschizine; and
(b) contacting monooxygenated geissoschizine with a mixture of enzymes comprising catalytic quantities of (i) REDOX 1; (ii) REDOX 2; (iii) SAT and (iv) HL1 under reaction conditions permitting the catalytic conversion of monooxygenated geissoschizine to form catharanthine.

The foregoing embodiments of the disclosure to make catharanthine are further illustrated in Table B.

The foregoing methods may be performed under in vivo conditions or under in vitro conditions as hereinafter detailed.

Monooxygenated Geissoschizine Synthesis

In one example embodiment of the disclosure, there is provided a method of making monooxygenated geissoschizine, the method comprising:
(a) providing strictosidine; and
(b) contacting strictosidine with a mixture of enzymes comprising catalytic quantities of (i) SGD; (ii) GS; and (iii) GO under reaction conditions permitting the catalytic conversion of strictosidine to form monooxygenated geissoschizine.

In one example embodiment of the disclosure, there is provided a method of making monooxygenated geissoschizine, the method comprising:
(a) providing strictosidine aglycone or a strictosidone aglycone derivative; and
(b) contacting strictosidine aglycone or the strictosidone aglycone derivative with a mixture of enzymes comprising catalytic quantities of (i) GS; and (ii) GO under reaction conditions permitting the catalytic conversion of strictosidine aglycone or the strictosidine aglycone derivative to form monooxygenated geissoschizine.

In one example embodiment of the disclosure, there is provided a method of making monooxygenated geissoschizine, the method comprising:
(a) providing 4,21-dehydrogeissoschizine; and
(b) contacting 4,21-dehydrogeissoschizine with a mixture of enzymes comprising catalytic quantities of (i) GS; and (ii) GO; under reaction conditions permitting the catalytic conversion of 4,21-dehydrogeissoschizine to form monooxygenated geissoschizine.

In one example embodiment of the disclosure, there is provided a method of making monooxygenated geissoschizine, the method comprising:
(a) providing geissoschizine; and
(b) contacting geissoschizine with catalytic quantities of the enzyme GO; under reaction conditions permitting the catalytic conversion of geissoschizine to form monooxygenated geissoschizine.

The foregoing embodiments of the disclosure to make monooxygenated geissoschizine are further illustrated in Table E.

The foregoing methods may be performed under in vivo conditions or under in vitro conditions as hereinafter detailed.

Geissoschizine Synthesis

In one example embodiment of the disclosure, there is provided a method of making geissoschizine, the method comprising:
(a) providing strictosidine; and
(b) contacting strictosidine, with a mixture of enzymes comprising catalytic quantities of (i) SGD and (ii) GS under reaction conditions permitting the catalytic conversion of strictosidine to form geissoschizine.

In one example embodiment of the disclosure, there is provided a method of making geissoschizine, the method comprising:
(a) providing strictosidine aglycone or a strictosidone aglycone derivative; and
(b) contacting strictosidine aglycone, or the strictosidone aglycone derivative with catalytic quantities of GS under reaction conditions permitting the catalytic conversion of strictosidine aglycone or the strictosidine aglycone derivative to form geissoschizine.

In one example embodiment of the disclosure, there is provided a method of making geissoschizine, the method comprising:
(a) providing 4,21-dehydrogeissoschizine; and
(b) contacting 4,21-dehydrogeissoschizine with catalytic quantities of the enzyme GS under reaction conditions permitting the catalytic conversion of 4,21-dehydrogeissoschizine to form geissoschizine.

The foregoing embodiments of the disclosure to make geissoschizine are further illustrated in Table F.

The foregoing methods may be performed under in vivo conditions or under in vitro conditions as hereinafter detailed.

4,21-Dehydrogeissoschizine Synthesis

In one example embodiment of the disclosure, there is provided a method of making 4,21-dehydrogeissoschizine, the method comprising:
(a) providing strictosidine; and
(b) contacting strictosidine, with catalytic quantities of the enzyme SGD under reaction conditions permitting the catalytic conversion of strictosidine or strictosidine aglycone to form 4,21-dehydrogeissoschizine.

The foregoing embodiments of the disclosure to make geissoschizine are further illustrated in Table G.

The foregoing methods may be performed under in vivo conditions or under in vitro conditions as hereinafter detailed.

Tabersonine-Catharanthine Synthesis Derivatives

In addition to tabersonine, catharanthine and tabersonine-catharanthine pathway intermediates, in certain embodiments hereof, tabersonine-catharanthine synthesis derivatives may also be prepared. Thus for example, the tabersonine-catharanthine synthesis derivatives ajmalicine, isositsirikine, pericyclivine, perivine, akuammicine, MIA1, MIA2, stemmadenine and O-acetylstemmadenine may be prepared as hereinafter set forth, and as further illustrated in FIG. 17.

Accordingly in one embodiment, the present disclosure provides a method of preparing a tabersonine-catharanthine synthesis derivative, the method comprising:
(a) providing a terpenoid indole alkaloid compound; and
(b) contacting the terpenoid indole alkaloid compound with at least one of the enzymes selected from the group consisting of (i) SGD; (ii) GS; (iii) and GO, under reaction conditions permitting the catalysis of the terpenoid indole alkaloid compound to form a tabersonine-catharanthine synthesis intermediate; and
(c) subjecting the tabersonine-catharanthine synthesis intermediate to reaction conditions that permit the conversion of the tabersonine-catharanthine synthesis intermediate to form a tabersonine-catharanthine synthesis derivative.

In further embodiments, the present disclosure provides a method of preparing a tabersonine-catharanthine synthesis derivative, the method comprising:
(a) providing a terpenoid indole alkaloid compound; and
(b) contacting the terpenoid indole alkaloid compound with at least one of the enzymes selected from the group consisting of (i) SGD; (ii) GS; and (iii) GO, under reaction conditions permitting the catalysis of the terpenoid indole alkaloid compound to form a tabersonine-catharanthine synthesis intermediate; and
(c) subjecting the tabersonine-catharanthine synthesis intermediate to reaction conditions that permit the conversion of the tabersonine-catharanthine synthesis intermediate to form a tabersonine-catharanthine synthesis derivative;
wherein the terpenoid indole alkaloid compound is selected from the group of terpenoid indole alkaloid compounds consisting of strictosidine, 4,21-dehydrogeissoschizine, geissoschizine and monooxygenated geissoschizine; and
wherein the tabersonine-catharanthine synthesis derivative is selected from the group of tabersonine-catharanthine synthesis derivatives consisting of cathenamine, ajmalicine, isositsirikine, pericyclivine, perivine, akuammicine, MIA1, MIA2, stemmadenine and O-acetylstemmadenine.

Ajmalicine Synthesis

In one embodiment, there is provided a method of making ajmalicine. Accordingly, there is provided a method of making ajmalicine comprising:
providing 4,21-dehydrogeissoschizine under reaction conditions that permit the conversion of 4,21-dehydrogeissoschizine to form cathenamine, and the subsequent conversion of cathenamine to form ajmalicine.

In one example embodiment of the disclosure, there is provided a method of making ajmalicine comprising:
(a) providing strictosidine; and
(b) contacting strictosidine, with catalytic quantities of the enzyme SGD under reaction conditions permitting an enzyme catalyzed chemical conversion of strictosidine to 4,21-dehydrogeissoschizine to form cathenamine, and the subsequent conversion of cathenamine to form ajmalicine.

In some embodiments, the subsequent conversion of cathenamine to form ajmalicine is a non-enzymatic conversion.

Isositsirikine Synthesis

In one embodiment, there is provided a method of making isositsirikine. Accordingly, in one example embodiment, there is provided a method of making isositsirikine comprising:
(a) providing geissoschizine; and
(b) contacting the geissoschizine with catalytic quantities of the enzyme REDOX 2 under reaction conditions that permit the conversion of geissoschizine to form isositsirikine.

In one example embodiment of the disclosure, there is provided a method of making isositsirikine comprising:
(a) providing 4,21-dehydrogeissoschizine; and
(b) contacting 4,21-dehydrogeissoschizine, with a mixture of enzymes comprising catalytic quantities of (i) GS and (iii) REDOX 2 under reaction conditions permitting an enzyme catalyzed chemical conversion of 4,21-dehydrogeissoschizine to form isositsirikine.

In one example embodiment of the disclosure, there is provided a method of making isositsirikine comprising:
(a) providing strictosidine; and
(b) contacting strictosidine, with catalytic quantities of a mixture of enzymes comprising (i) SGD; (ii) GS and (iii) REDOX 2 under reaction conditions permitting an enzyme catalyzed chemical conversion of strictosidine to form isositsirikine.

In one example embodiment of the disclosure, there is provided a method of making isositsirikine, the method comprising:
(a) providing strictosidine aglycone or a strictosidone aglycone derivative; and
(b) contacting strictosidine aglycone, or the strictosidone aglycone derivative with a mixture of enzymes comprising catalytic quantities of (i) GS and (ii) REDOX 2 under reaction conditions permitting the catalytic conversion of strictosidine aglycone or the strictosidine aglycone derivative to form isositsirikine.

Pericyclivine Synthesis

In one embodiment, there is provided a method of making pericyclivine. Accordingly, there is provided a method of making pericyclivine comprising:
providing geissoschizine under reaction conditions that permit the conversion of geissoschizine to form pericyclivine.

In one example embodiment of the disclosure, there is provided a method of making pericyclivine comprising:
(a) providing 4,21-dehydrogeissoschizine; and
(b) contacting 4,21-dehydrogeissoschizine, with catalytic quantities of the enzyme GS under reaction conditions permitting an enzyme catalyzed chemical conversion of 4,21-dehydrogeissoschizine to form geissoschizine and the subsequent conversion of geissoschizine to pericyclivine.

In some embodiments, the subsequent conversion of geissoschizine to form pericyclivine is a non-enzymatic conversion.

In one example embodiment of the disclosure, there is provided a method of making pericyclivine comprising:
(a) providing strictosidine; and
(b) contacting strictosidine, with a mixture of enzymes comprising catalytic quantities of (i) SGD; and (ii) GS under reaction conditions permitting an enzyme catalyzed chemical conversion of strictosidine to form geissoschizine and the subsequent conversion of geissoschizine to pericyclivine.

In some embodiments, the subsequent conversion of geissoschizine to form pericyclivine is a non-enzymatic conversion.

In one example embodiment of the disclosure, there is provided a method of making pericyclivine, the method comprising:
(a) providing strictosidine aglycone or a strictosidone aglycone derivative; and
(b) contacting strictosidine aglycone, or the strictosidone aglycone derivative with catalytic quantities of the enzyme GS under reaction conditions permitting the catalytic conversion of strictosidine aglycone or the strictosidine aglycone derivative to form geissoschizine and the subsequent conversion of geissoschizine to pericyclivine.

In some embodiments, the subsequent conversion of geissoschizine to form pericyclivine is a non-enzymatic conversion.

Perivine Synthesis

In one embodiment, there is provided a method of making perivine. Accordingly, there is provided a method of making perivine comprising: providing geissoschizine under reaction conditions that permit the conversion of geissoschizine to form perivine.

In one example embodiment of the disclosure, there is provided a method of making perivine comprising:
(a) providing 4,21-dehydrogeissoschizine; and
(b) contacting 4,21-dehydrogeissoschizine, with catalytic quantities of the enzyme GS under reaction conditions permitting an enzyme catalyzed chemical conversion of 4,21-dehydrogeissoschizine to form geissoschizine and the subsequent conversion of geissoschizine to perivine.

In some embodiments, the subsequent conversion of geissoschizine to perivine is a non-enzymatic conversion.

In one example embodiment of the disclosure, there is provided a method of making perivine comprising:
(a) providing strictosidine; and
(b) contacting strictosidine, with a mixture of enzymes comprising catalytic quantities of (i) SGD; and (ii) GS under reaction conditions permitting an enzyme catalyzed chemical conversion of strictosidine to form geissoschizine and the subsequent conversion of geissoschizine to perivine.

In some embodiments, the subsequent conversion of geissoschizine to perivine is a non-enzymatic conversion.

In one example embodiment of the disclosure, there is provided a method of making perivine, the method comprising:
(a) providing strictosidine aglycone or a strictosidone aglycone derivative; and
(b) contacting strictosidine aglycone, or the strictosidone aglycone derivative with catalytic quantities of the enzyme GS under reaction conditions permitting the catalytic conversion of strictosidine aglycone or the strictosidine aglycone derivative to form geissoschizine and the subsequent conversion of geissoschizine to perivine.

In some embodiments, the subsequent conversion of geissoschizine to perivine is a non-enzymatic conversion.

Akuammicine Synthesis

In one embodiment, there is provided a method of making akuammicine. Accordingly, there is provided a method of making akuammicine comprising:
providing monooxygenated geissoschizine under reaction conditions that permit the conversion of monooxygenated geissoschizine to form akuammicine.

In one example embodiment of the disclosure, there is provided a method of making akuammicine comprising:
(a) providing geissoschizine; and
(b) contacting geissoschizine, with catalytic quantities of the enzyme GO under reaction conditions permitting an enzyme catalyzed chemical conversion of geissoschizine to form monooxygenated geissoschizine and the subsequent conversion of monooxygenated geissoschizine to akuammicine.

In some embodiments, the subsequent conversion of monooxygenated geissoschizine to form akuammicine is a non-enzymatic conversion.

In one example embodiment of the disclosure, there is provided a method of making akuammicine comprising:
(a) providing 4,21-dehydrogeissoschizine; and
(b) contacting 4,21-dehydrogeissoschizine, with a mixture of enzymes comprising catalytic quantities of (i) GS and (ii) GO under reaction conditions permitting an enzyme catalyzed chemical conversion of 4,21-dehydrogeissoschizine to form monooxygenated geissoschizine and the subsequent conversion of monooxygenated geissoschizine to akuammicine.

In some embodiments, the subsequent conversion of monooxygenated geissoschizine to form akuammicine is a non-enzymatic conversion.

In one example embodiment of the disclosure, there is provided a method of making akuammicine comprising:
(a) providing strictosidine; and
(b) contacting strictosidine, with a mixture of enzymes comprising catalytic quantities of (i) SGD; (ii) GS; and (iii) GO under reaction conditions permitting an enzyme catalyzed chemical conversion of strictosidine to form monooxygenated geissoschizine and the subsequent conversion of monooxygenated geissoschizine to akuammycine.

In some embodiments, the subsequent conversion of monooxygenated geissoschizine to form akuammicine is a non-enzymatic conversion.

In one example embodiment of the disclosure, there is provided a method of making akuammicine, the method comprising:
(a) providing strictosidine aglycone or a strictosidone aglycone derivative; and
(b) contacting strictosidine aglycone, or the strictosidone aglycone derivative with a mixture of enzymes comprising catalytic quantities of the enzyme (i) GS and (ii) GO under reaction conditions permitting the catalytic conversion of strictosidine aglycone or the strictosidine aglycone derivative to form monooxygenated geissoschizine and the subsequent conversion of monooxygenated geissoschizine to akuammicine.

In some embodiments, the subsequent conversion of monooxygenated geissoschizine to form akuammicine is a non-enzymatic conversion.

MIA1 Synthesis

In one embodiment, there is provided a method of making MIA1. Accordingly there is provided a method of making MIA1 comprising:
(a) providing monooxygenated geissoschizine; and
(b) contacting the monooxygenated geissoschizine with catalytic quantities of the enzyme REDOX 1 under reaction conditions that permit the conversion of monooxygenated geissoschizine to form MIA1.

In one example embodiment of the disclosure, there is provided a method of making MIA1 comprising:
(a) providing geissoschizine; and
(b) contacting geissoschizine, with a mixture or enzymes comprising catalytic quantities of (i) GO and (ii) REDOX 1 under reaction conditions permitting an enzyme catalyzed chemical conversion of geissoschizine to form MIA1.

In one example embodiment of the disclosure, there is provided a method of making MIA1 comprising:
(a) providing 4,21-dehydrogeissoschizine; and
(b) contacting 4,21-dehydrogeissoschizine, with a mixture of enzymes comprising catalytic quantities of (i) GS; (ii) GO and REDOX 1 under reaction conditions permitting an enzyme catalyzed chemical conversion of 4,21-dehydrogeissoschizine to form MIA1.

In one example embodiment of the disclosure, there is provided a method of making MIA1 comprising:
(a) providing strictosidine; and
(b) contacting strictosidine, with a mixture of enzymes comprising catalytic quantities of (i) SGD; (ii) GS; (iii) GO and (iv) REDOX 1 under reaction conditions permitting an enzyme catalyzed chemical conversion of strictosidine to form MIA1.

In one example embodiment of the disclosure, there is provided a method of making MIA1, the method comprising:
(a) providing strictosidine aglycone or a strictosidone aglycone derivative; and
(b) contacting strictosidine aglycone, or the strictosidone aglycone derivative with a mixture of enzymes comprising catalytic quantities of the enzyme (i) GS; (ii) GO; and (iii) REDOX 1 under reaction conditions permitting the catalytic conversion of strictosidine aglycone or the strictosidine aglycone derivative to form MIA 1.

MIA2 Synthesis

In one embodiment, there is provided a method of making MIA2. Accordingly there is provided a method of making MIA2 comprising:
(a) providing monooxygenated geissoschizine; and
(b) contacting the monooxygenated geissoschizine with catalytic quantities of the enzyme REDOX 1 under reaction conditions that permit the conversion of monooxygenated geissoschizine to form MIA2.

In one example embodiment of the disclosure, there is provided a method of making MIA2 comprising:
(a) providing geissoschizine; and
(b) contacting geissoschizine, with a mixture or enzymes comprising catalytic quantities of (i) GO and (ii) REDOX 1 under reaction conditions permitting an enzyme catalyzed chemical conversion of geissoschizine to form MIA2.

In one example embodiment of the disclosure, there is provided a method of making MIA2 comprising:
(a) providing 4,21-dehydrogeissoschizine; and
(b) contacting 4,21-dehydrogeissoschizine, with a mixture of enzymes comprising catalytic quantities of (i) GS; (ii) GO and REDOX 1 under reaction conditions permitting an enzyme catalyzed chemical conversion of 4,21-dehydrogeissoschizine to form MIA2.

In one example embodiment of the disclosure, there is provided a method of making MIA2 comprising:
(a) providing strictosidine; and
(b) contacting strictosidine, with a mixture of enzymes comprising catalytic quantities of (i) SGD; (ii) GS; (iii) GO and (iv) REDOX 1 under reaction conditions permitting an enzyme catalyzed chemical conversion of strictosidine to form MIA2.

In one example embodiment of the disclosure, there is provided a method of making MIA2, the method comprising:
(a) providing strictosidine aglycone or a strictosidone aglycone derivative; and
(b) contacting strictosidine aglycone, or the strictosidone aglycone derivative with a mixture of enzymes comprising catalytic quantities of the enzyme (i) GS; (ii) GO; and (iii) REDOX 1 under reaction conditions permitting the catalytic conversion of strictosidine aglycone or the strictosidine aglycone derivative to form MIA 2.

O-acetylstemmadenine Synthesis

In one embodiment, there is provided a method of making O-acetylstemmadenine. Accordingly, in one example embodiment of the disclosure, there is provided a method of making O-actelylstemmadenine comprising:
(a) providing strictosidine; and
(b) contacting strictosidine, with a mixture comprising catalytic quantities of the enzymes (i) SGD; (ii) GS; (iii) GO; (iv) REDOX 1; (v) REDOX 2; and (vi) SAT under reaction conditions permitting an enzyme catalyzed chemical conversion of strictosidine to O-acetylstemmadenine.

In one example embodiment of the disclosure, there is provided a method of making O-acetylstemmadenine, the method comprising:
(a) providing strictosidine aglycone or a strictosidone aglycone derivative; and
(b) contacting strictosidine aglycone or the strictosidone aglycone derivative with a mixture of enzymes comprising catalytic quantities of (i) GS; (ii) GO; and (iii) REDOX 1; (iv) REDOX 2 and (v) SAT under reaction conditions permitting the catalytic conversion of strictosidine aglycone or the strictosidine aglycone derivative to form O-acetylstemmadenine.

In one example embodiment of the disclosure, there is provided a method of making O-acetylstemmadenine, the method comprising:
(a) providing 4,21-dehydrogeissoschizine; and
(b) contacting 4,21-dehydrogeissoschizine with a mixture of enzymes comprising catalytic quantities of (i) GS; (ii) GO; (iii) REDOX 1: (iv) REDOX 2; and (v) SAT under reaction conditions permitting the catalytic conversion of 4,21-dehydrogeissoschizine to form O-acetylstemmadenine.

In one example embodiment of the disclosure, there is provided a method of making O-acetylstemmadenine, the method comprising:
(a) providing geissoschizine; and
(b) contacting geissoschizine with a mixture of enzymes comprising catalytic quantities of (i) GO; and (ii) REDOX 1; (iii) REDOX 2 and (iv) SAT under reaction conditions permitting the catalytic conversion of geissoschizine to form O-acetylstemmadenine.

In one example embodiment of the disclosure, there is provided a method of making O-acetylstemmadenine, the method comprising:
(a) providing monooxygenated geissoschizine; and
(b) contacting monooxygenated geissoschizine with a mixture of enzymes comprising catalytic quantities of (i) REDOX 1; (ii) REDOX 2 and (iii) SAT under reaction conditions permitting the catalytic conversion of monooxygenated geissoschizine to form O-acetylstemmadenine.

In one example embodiment of the disclosure, there is provided a method of making O-acetylstemmadenine, the method comprising:
(a) providing stemmadenine; and
(b) contacting stemmadenine with catalytic quantities of SAT under reaction conditions permitting the catalytic conversion of stemmadenine to form O-acetylstemmadenine.

The foregoing embodiments of the disclosure to make O-acetylstemmadenine are further illustrated in Table C.

The foregoing methods may be performed under in vivo conditions or under in vitro conditions as hereinafter detailed.

Stemmadenine Synthesis

In one embodiment, there is provided a method of making stemmadenine. Accordingly, in one example embodiment of the disclosure, there is provided a method of making stemmadenine, the method comprising:
(a) providing strictosidine; and
(b) contacting strictosidine with a mixture of enzymes comprising catalytic quantities of (i) SGD; (ii) GS; (iii) GO; (iv) REDOX 1; and (v) REDOX 2 under reaction conditions permitting the catalytic conversion of strictosidine to form stemmadenine.

In one example embodiment of the disclosure, there is provided a method of making stemmadenine, the method comprising:
(a) providing strictosidine aglycone or a strictosidone aglycone derivative; and
(b) contacting strictosidine aglycone or the strictosidone aglycone derivative with a mixture of enzymes comprising catalytic quantities of (i) GS; (ii) GO; and (iii) REDOX 1; and (iv) REDOX 2 under reaction conditions permitting the catalytic conversion of strictosidine aglycone or the strictosidine aglycone derivative to form stemmadenine.

In one example embodiment of the disclosure, there is provided a method of making stemmadenine, the method comprising:
(a) providing 4,21-dehydrogeissoschizine; and
(b) contacting 4,21-dehydrogeissoschizine with a mixture of enzymes comprising catalytic quantities of (i) GS; (ii) GO; and (iii) REDOX 1; and (iv) REDOX 2 under reaction conditions permitting the catalytic conversion of 4,21-dehydrogeissoschizine to form stemmadenine.

In one example embodiment of the disclosure, there is provided a method of making stemmadenine, the method comprising:
(a) providing geissoschizine; and
(b) contacting geissoschizine with a mixture of enzymes comprising catalytic quantities of (i) GO; and (ii) REDOX 1; and REDOX 2 under reaction conditions permitting the catalytic conversion of geissoschizine to form stemmadenine.

In one example embodiment of the disclosure, there is provided a method of making stemmadenine, the method comprising:
(a) providing monooxygenated geissoschizine; and
(b) contacting monooxygenated geissoschizine with a mixture of enzymes comprising catalytic quantities of (i) REDOX 1; and REDOX 2 under reaction conditions permitting the catalytic conversion of monooxygenated geissoschizine to form stemmadenine.

The foregoing embodiments of the disclosure to make stemmadenine are further illustrated in Table D.

The foregoing methods may be performed under in vivo conditions or under in vitro conditions as hereinafter detailed.

In Vitro Synthesis of Tabersonine, Catharanthine, Tabersonine-Catharanthine Synthesis Intermediates and Tabersonine-Catharanthine Synthesis Derivatives In accordance with certain aspects of the present disclosure, a tabersonine-catharanthine pathway precursor compound, or a tabersonine-catharanthine pathway precursor derivative compound is brought in contact with catalytic quantities of one or more of the enzymes SGD; GS; GO; REDOX 1; REDOX 2; SAT; HL1; and HL2 under reaction conditions permitting an enzyme catalyzed chemical conversion of the tabersonine-catharanthine pathway precursor compound or tabersonine-catharanthine pathway precursor derivative compound under in vitro reaction conditions. Under such in vitro reaction conditions the initial reaction constituents are provided in more or less pure form and are mixed under conditions that permit the requisite chemical reactions to substantially proceed. Substantially pure forms of the initial tabersonine-catharanthine pathway precursor compound or tabersonine-catharanthine pathway precursor derivative compound may be chemically synthesized, or are isolated from natural sources including plants belonging to Apocynacea plant family, including the genus *Catharanthus*, including, *Catharanthus roseus*, and other species belonging to the genus *Catharanthus*, and further including plants belonging to the genus *Lonerica*, including *Lonerica japonica* and other species belonging to the genus *Lonerica*, plants belonging to the genus *Vinca*, including *Vinca minor* and other species belonging to the genus *Vinca*, plants belonging to the genus *Amsonia*, including *Amsonia hubrichtii* and other species belonging to the genus *Amsonia*, and plants belonging to the genus *Tabernaemontana*, including *Tabernaemontana elegans* and other species belonging to the genus *Tabernaemontana*. The tabersonine-catharanthine pathway precursor strictosidine may be synthesized chemically or prepared enzymatically by enzymatically coupling tryptamine to secologanin, each of which may be obtained from various fine chemical agent suppliers (e.g. Sigma-Aldrich®, St Louis, Mo., USA), using strictosidine synthase (Treimer J. F., Zenk M. H., 1979, *Eur. J. Biochem.* 101: 225-233). Alternatively secologanin may be extracted from plant sources including, for example from *Lonicera japonica* leaves which can contain 1 mg secologanin per gram fresh weight (Kawai, H. et al., 1988, *THUNB. Chem. Pherm. Bull.* 36: 3664-3666). Both tryptamine and secologanin can also be produced in yeast by metabolic pathway engineering (Brown S., et al., 2015, *Proc. Natl. Acad. Sci. USA* 112: 3205-3210).

In accordance herewith, more or less pure forms of the enzymes may be isolated from natural sources, including *Catharanthus roseus, Vinca minor, Amsonia hubrichtii* and *Tabernaemontana elegans* or they may be prepared recombinantly. Thus, provided herein is further a method for preparing an enzyme selected from the group consisting of SGD; GS; GO; REDOX 1; REDOX 2; SAT; HL1; and HL2 comprising:
  (a) providing a chimeric nucleic acid sequence comprising as operably linked components:
    (i) one or more nucleic acid sequences encoding one or more of the polypeptides selected from the group of polypeptides consisting of SGD; GS; GO; REDOX 1; REDOX 2; SAT; HL1 and HL2; and
    (ii) one or more nucleic acid sequences capable of controlling expression in a host cell;
  (b) introducing the chimeric nucleic acid sequence into a host cell and growing the host cell to produce the polypeptide selected from the group of polypeptides consisting of SGD; GS; GO; REDOX 1; REDOX 2; HL1; SAT; and HL2 and
  (c) recovering SGD; GS; GO; REDOX 1; REDOX 2; HL1; SAT; and HL2 from the host cell.

In preferred embodiments, the enzymes are polypeptides having a polypeptide sequence represented by SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 16; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; or SEQ ID NO: 56, notably:
  with respect to SGD: SEQ ID NO: 1; or any nucleic acid that is substantially similar thereto;
  with respect to GS: SEQ ID NO: 2; SEQ ID NO: 37; SEQ ID NO: 38; or SEQ ID NO: 39; or any nucleic acid that is substantially similar thereto;
  with respect to GO: SEQ ID NO: 3; SEQ ID NO: 40; SEQ ID NO: 41; or SEQ ID NO: 42; or any nucleic acid that is substantially similar thereto;
  with respect to REDOX1: SEQ ID NO: 4; SEQ ID NO: 43; SEQ ID NO: 44; or SEQ ID NO: 45; or any nucleic acid that is substantially similar thereto;
  with respect to REDOX 2: SEQ ID NO: 5; SEQ ID NO: 46; SEQ ID NO: 47; or SEQ ID NO: 48; or any nucleic acid that is substantially similar thereto;
  with respect to HL1: SEQ ID NO: 6 or any nucleic acid that is substantially similar thereto;
  with respect to HL2: SEQ ID NO: 7; SEQ ID NO: 52; SEQ ID NO: 53; SEQ ID NO: 54; SEQ ID NO: 55; or SEQ ID NO: 56; or any nucleic acid that is substantially similar thereto; and
  with respect to SAT: SEQ ID NO: 16; SEQ ID NO: 49; SEQ ID NO: 50; SEQ ID NO: 51; or any nucleic acid that is substantially similar thereto.

Growth of the host cells leads to production of the SGD; GS; GO; REDOX 1; REDOX 2; SAT; HL1 and/or HL2 polypeptides. The polypeptides subsequently may be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus substantially pure preparations of the SGD; GS; GO; REDOX 1; REDOX 2; SAT; HL1 and/or HL2 polypeptides may be obtained. Combinations of polypeptides may be selected in accordance with Tables A-G and any and all of the combinations of the enzymes set forth in Tables A-G are specifically included herein.

In accordance herewith a tabersonine-catharanthine pathway precursor compound or a tabersonine-catharanthine pathway precursor derivative compound is brought in contact with catalytic quantities of one or more of the enzymes SGD; GS; GO; REDOX 1; REDOX 2; SAT; HL1 and HL2 under reaction conditions permitting an enzyme catalyzed chemical conversion of the tabersonine-catharanthine pathway precursor compound or tabersonine-catharanthine pathway precursor derivative compound. Catalytic quantities of enzymes are preferably less than about 1% (w/w), less than about 0.5% (w/w), less than about 0.1% (w/w), less than about 0.05% (w/w), or less than about 0.01% (w/w) of the reaction mixture. In preferred embodiments, the agents are brought in contact with each other and mixed to form a mixture. In preferred embodiments, the mixture is an aqueous mixture comprising water and further optionally additional agents to facilitate enzyme catalysis, including buffering agents, salts, pH modifying agents, as well as co-factors, for example acetyl coenzyme A, NAD+ NADP+, NADH or NADPH. The reaction can be performed under a range of different conditions, including, without limitation, at a range of different temperatures. In preferred embodiments, the reaction is performed at a temperature between about 18° C. and 37° C. Upon completion of the in vitro reaction tabersonine, catharanthine or a tabersonine-catharanthine synthesis intermediate compound may be obtained in more or less pure form. It will be understood by those of skill in the art that the quantities of the terpenoid indole alkaloids that are obtained may vary, and that depending on the exact reaction conditions selected, together with catharanthine or tabersonine or a desired tabersonine-catharanthine synthesis intermediate, compounds upstream thereof may be obtained. In general, it will be possible to select, through routine optimization, the reaction conditions in such a manner that the presence of tabersonine-catharanthine synthesis intermediate compounds, upstream of tabersonine or catharanthine, or upstream of the desired selected tabersonine-catharanthine synthesis intermediate compound, is minimized. Thus the amount of buffering agents, salts, pH modifying agents, as well as co-factors, and the reaction conditions may be optimized or adjusted, for example, by preparing a plurality of samples and performing the reaction under a plurality of conditions, and evaluating the amount of tabersonine, catharanthine or tabersonine-catharanthine synthesis intermediate that is obtained. Then, a reaction condition may be selected that provides the most desirable amounts.

Figure 17:
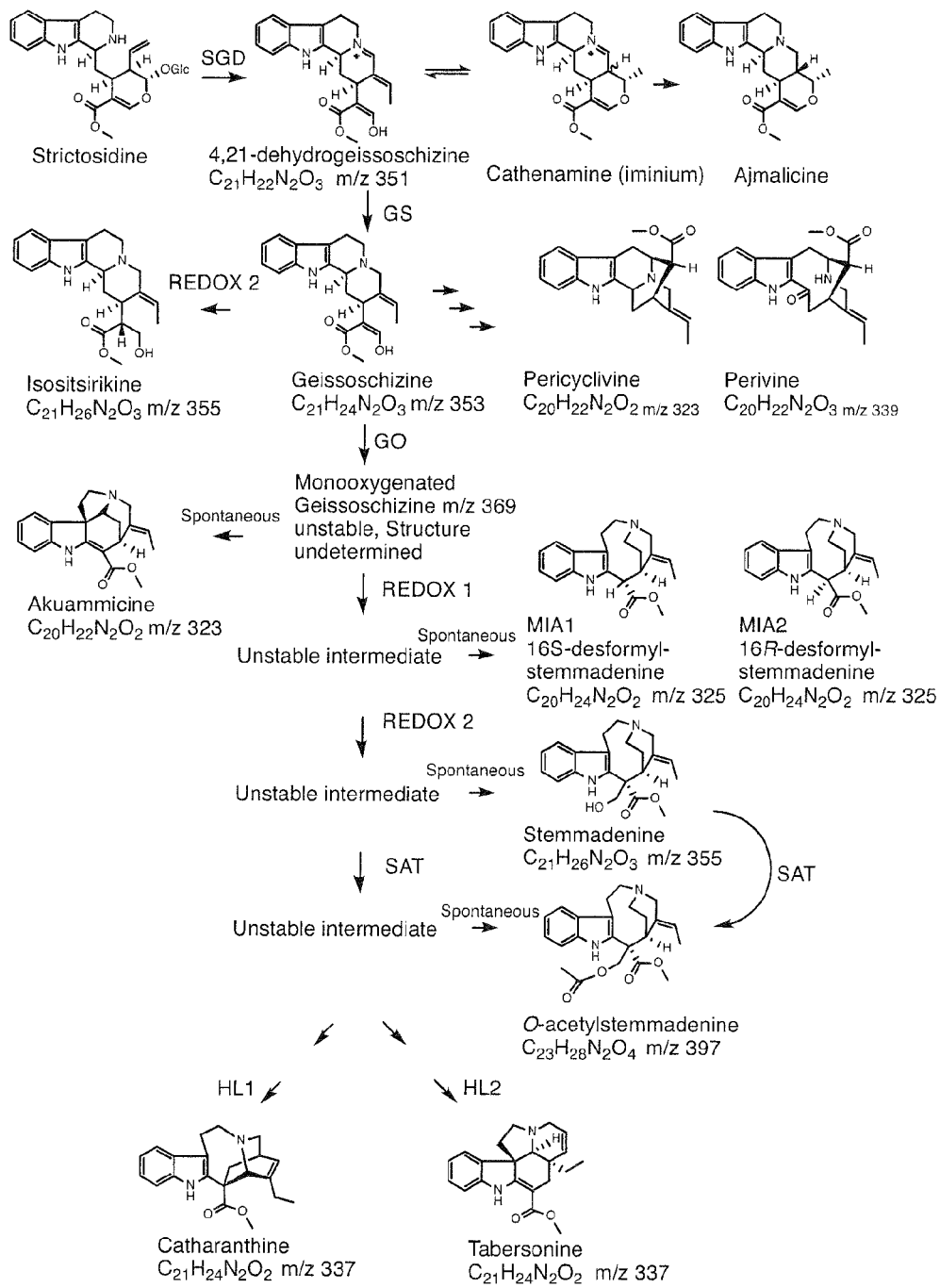
FIG. 17 depicts the tabersonine-catharanthine pathway, including several tabersonine-catharanthine synthesis derivatives. The following derivatives are shown cathenamine (iminium form), ajmalicine; isositsirikine, pericyclivine and perivine (geissoschizine derivatives); MIA1, MIA 2, akuammicine, and stemmadenine and O-acetylstemmadenine (monooxygenated geissoschizine derivatives).

In embodiments hereof where tabersonine-catharanthine synthesis derivatives are formed from tabersonine-catharanthine synthesis intermediates, the aforementioned generally described in-vitro reaction conditions will be equally applicable and implementable with reference to FIG. 17.

In Vivo Synthesis of Tabersonine, Catharanthine, Tabersonine-Catharanthine Synthesis Intermediates, and Tabersonine-Catharanthine Synthesis Derivatives In accordance with certain aspects of the present disclosure, a tabersonine-catharanthine precursor or a tabersonine-catharanthine pathway precursor derivative compound is brought in contact with catalytic quantities of one or more of the enzymes SGD; GS; GO; REDOX 1; REDOX 2; SAT; HL1; and HL2 under reaction conditions permitting an enzyme catalyzed chemical conversion of the tabersonine-catharanthine pathway precursor compound or tabersonine-catharanthine pathway precursor derivative compound under in vivo reaction conditions. Under such in vivo reaction conditions living cells are modified in such a manner that they produce tabersonine, catharanthine, a tabersonine-catharanthine synthesis intermediate, or a tabersonine-catharanthine synthesis derivative. In certain embodiments the living cells are microorganisms, including bacterial cells and fungal cells. In other embodiments the living cells are multicellular organisms, including plants.

In one embodiment, the living cells are selected to be host cells capable of producing at least one of the tabersonine-catharanthine pathway precursor compounds or tabersonine-catharanthine pathway precursor derivative compounds of the present disclosure, but are unable to produce tabersonine, catharanthine or one or more of the tabersonine-catharanthine synthesis intermediates, or tabersonine-catharanthine synthesis derivatives of the present disclosure. Such cells include, without limitation, bacteria, yeast, other fungal cells, plant cells, or animal cells. Thus, by way of example only, a host cell may be a yeast host cell capable of producing strictosidine, but not any of 4,21-dehydrogeissoschizine; geissoschizine; monooxygenated geissoschizine; tabersonine or catharanthine. In order to modulate such host cells in such a manner that they produce tabersonine or catharanthine or a tabersonine-catharanthine synthesis intermediate, one or more of the enzymes selected from the group consisting of SGD; GS; GO; REDOX 1; REDOX 2; SAT; HL1; and HL2 in accordance herewith may be heterologously introduced and expressed in the host cells.

In other embodiments, the living cells naturally produce one or more of the tabersonine-catharanthine synthesis intermediates, or tabersonine-catharanthine synthesis derivatives of the present disclosure, or, tabersonine or catharanthine, however the living cells are modulated in such a manner that the levels of one or more of the tabersonine-catharanthine synthesis intermediates, or tabersonine-catharanthine synthesis derivatives, or tabersonine or catharanthine produced in the cells is modulated, in a manner in which the concentration of these terpenoid indole alkaloids is increased relative to the concentration present without heterologous introduction of any of the aforementioned enzymes in such living cells.

In order to produce tabersonine, catharanthine, a tabersonine-catharanthine synthesis intermediate, or a tabersonine-catharanthine synthesis derivative, provided herein is further a method for preparing tabersonine, catharanthine, one or more of the tabersonine-catharanthine synthesis intermediates, or tabersonine-catharanthine synthesis derivatives, the method comprising:
(a) providing a chimeric nucleic acid sequence comprising as operably linked components:
  (i) one or more nucleic acid sequences encoding one or more of the polypeptides selected from the group of polypeptides consisting of SGD; GS; GO; REDOX 1; REDOX 2; SAT; HL1; and HL2; and
  (ii) one or more nucleic acid sequences capable of controlling expression in a host cell;
(b) introducing the chimeric nucleic acid sequence into a host cell and growing the host cell to produce the polypeptide selected from the group of polypeptides consisting of SGD; GS; GO; REDOX 1; REDOX 2; SAT; HL1; and HL2 and to produce one or more of tabersonine, catharanthine or one of the tabersonine-catharanthine synthesis intermediates, or tabersonine-catharanthine synthesis derivatives; and
(c) recovering tabersonine, catharanthine, or a tabersonine-catharanthine synthesis intermediate, or a tabersonine-catharanthine synthesis derivative.

In preferred embodiments, the nucleic acid sequences are selected from the nucleic acid sequences set forth herein as one or more of SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36 or nucleic acid sequences substantially identical to any of these sequences, notably:

with respect to SGD: SEQ ID NO: 8; or any nucleic acid that is substantially similar thereto;

with respect to GS: SEQ ID NO: 9; SEQ ID NO: 17; SEQ ID NO: 18; or SEQ ID NO: 19; or any nucleic acid that is substantially similar thereto;

with respect to GO: SEQ ID NO: 10; SEQ ID NO: 20; SEQ ID NO: 21; or SEQ ID NO: 22; or any nucleic acid that is substantially similar thereto;

with respect to REDOX1: SEQ ID NO: 11; SEQ ID NO: 23; SEQ ID NO: 24; or SEQ ID NO: 25; or any nucleic acid that is substantially similar thereto;

with respect to REDOX 2: SEQ ID NO: 12; SEQ ID NO: 26; SEQ ID NO: 27; or SEQ ID NO: 28; or any nucleic acid that is substantially similar thereto;

with respect to HL1: SEQ ID NO: 13 or any nucleic acid that is substantially similar thereto;

with respect to HL2: SEQ ID NO: 14; SEQ ID NO: 32; SEQ ID NO: 33; SEQ ID NO: 34; SEQ ID NO: 35; or SEQ ID NO: 36; or any nucleic acid that is substantially similar thereto; and with respect to SAT: SEQ ID NO: 15; SEQ ID NO: 29; SEQ ID NO: 30; SEQ ID NO: 31; or any nucleic acid that is substantially similar thereto.

The hereinbefore mentioned polypeptide or polypeptides are selected are selected in accordance with the specific tabersonine-catharanthine synthesis intermediate(s), or tabersonine-catharanthine synthesis derivative(s), or tabersonine or catharanthine that is desirable to obtain. Thus, by way of non-limiting example, if one wishes to prepare tabersonine one may introduce in a host cell capable of producing strictosidine, a chimeric nucleic acid sequence into a host cell encoding the polypeptides SGD; GS; GO; REDOX 1; REDOX 2; SAT and HL2 (e.g. a nucleic acid sequence comprising SEQ ID NO: 8; SEQ ID NO: 9; SEQ ID NO: 10; SEQ ID NO: 11; SEQ ID NO: 12; SEQ ID NO: 13; SEQ ID NO: 15 and SEQ ID NO: 14). Further combinations of nucleic acid sequences in order to produce tabersonine, catharanthin or tabersonine-catharanthine synthesis intermediates in accordance herewith may be selected by referring to Tables A-G and any and all of the combinations of nucleic acid sequences encoding the enzymes set forth in Tables A-G are specifically included herein.

In accordance herewith the nucleic acid sequence encoding SGD; GS; GO; REDOX 1; REDOX 2; HL1; SAT; and/or HL2 is linked to a nucleic acid sequence capable of controlling expression of SGD; GS; GO; REDOX 1; REDOX 2; HL1; SAT; and/or HL2 in a host cell. Accordingly, the present disclosure also provides a nucleic acid sequence encoding SGD; GS; GO; REDOX 1; REDOX 2; SAT; HL1; and/or HL2 linked to a promoter capable of controlling expression in a host cell. Nucleic acid sequences capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further nucleic acid elements capable elements of controlling expression in a host cell include transcriptional terminators, enhancers and the like, all of which may be included in the chimeric nucleic acid sequences of the present disclosure.

In accordance with the present disclosure, the chimeric nucleic acid sequences comprising a promoter capable of controlling expression in host cell linked to a nucleic acid sequence encoding SGD; GS; GO; REDOX 1; REDOX 2; SAT: HL1; and HL2, can be integrated into a recombinant expression vector which ensures good expression in the host cell. Accordingly, the present disclosure includes a recombinant expression vector comprising in the 5' to 3' direction of transcription as operably linked components:

(i) a polynucleotide capable of controlling expression in a host cell; and (ii) a polynucleotide encoding SGD; GS; GO; REDOX 1; REDOX 2; SAT; HL1; and/or HL2.

wherein the expression vector is suitable for expression in a host cell. The term "suitable for expression in a host cell" means that the recombinant expression vector comprises the chimeric nucleic acid sequence of the present disclosure linked to genetic elements required to achieve expression in a host cell. Genetic elements that may be included in the expression vector in this regard include a transcriptional termination region, one or more nucleic acid sequences encoding marker genes, one or more origins of replication and the like. The polynucleotides encoding SGD; GS; GO; REDOX 1; REDOX 2; SAT; HL1; and/or HL2 may be any polynucleotides comprising nucleic acid sequences encoding such polypeptides, including:

with respect to SGD: SEQ ID NO: 8; or any nucleic acid that is substantially similar thereto;

with respect to GS: SEQ ID NO: 9; SEQ ID NO: 17; SEQ ID NO: 18; or SEQ ID NO: 19; or any nucleic acid that is substantially similar thereto;

with respect to GO: SEQ ID NO: 10; SEQ ID NO: 20; SEQ ID NO: 21; or SEQ ID NO: 22; or any nucleic acid that is substantially similar thereto;

with respect to REDOX1: SEQ ID NO: 11; SEQ ID NO: 23; SEQ ID NO: 24; or SEQ ID NO: 25; or any nucleic acid that is substantially similar thereto;

with respect to REDOX 2: SEQ ID NO: 12; SEQ ID NO: 26; SEQ ID NO: 27; or SEQ ID NO: 28; or any nucleic acid that is substantially similar thereto;

with respect to HL1: SEQ ID NO: 13 or any nucleic acid that is substantially similar thereto;

with respect to HL2: SEQ ID NO: 14; SEQ ID NO: 32; SEQ ID NO: 33; SEQ ID NO: 34; SEQ ID NO: 35; or SEQ ID NO: 36; or any nucleic acid that is substantially similar thereto; and with respect to SAT: SEQ ID NO: 15; SEQ ID NO: 29; SEQ ID NO: 30; SEQ ID NO: 31; or any nucleic acid that is substantially similar thereto.

In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome. Further combinations of nucleic acid sequences in order to produce tabersonine, catharanthine or tabersonine-catharanthine synthesis intermediates in accordance herewith may be selected by referring to Tables A-G.

Pursuant to the present disclosure the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos.

5,268,463 and 5,599,670) and green fluorescent protein (GFP) (Niedz et al., 1995, *Plant Cell Rep.*, 14: 403).

One host cell that particularly conveniently may be used is *Escherichia coli*. The preparation of the *E. coli* vectors may be accomplished using commonly known techniques such as restriction digestion, ligation, gelectrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Other host cells may be plant cells, including, without limitation, *Catharanthus roseus, Vinca minor, Lonerica japonica, Amsonia hubrichtii* and *Tabernaemontana elegans*, and microbial cells, such as bacterial cells (including the aforementioned *E. coli*) and yeast cells, including *Saccharomyces cerevisiae* and *Yarrowia lipolytica*, and algal cells.

Further included in the present disclosure are a host cell wherein the host cell comprised a chimeric nucleic acid sequence comprising in the 5' to 3' direction of transcription as operably linked components one or more nucleic acid sequences encoding one or more of the polypeptides selected from the group of polypeptides consisting of SGD; GS; GO; REDOX 1; REDOX 2; SAT; HL1; and HL2. As hereinbefore mentioned the host cell is preferably a host cell capable of producing at least one of the tabersonine-catharanthine pathway precursor compounds of the present disclosure, but is unable to produce tabersonine, catharanthine or one or more tabersonine-catharanthine synthesis intermediates or tabersonine-catharanthine synthesis derivatives of the present disclosure, but for the introduction of the chimeric nucleic acid sequences of the present disclosure. Combinations of nucleic acid sequences in order to produce tabersonine, catharanthine, tabersonine-catharanthine synthesis intermediates, or tabersonine-catharanthine synthesis derivatives in accordance herewith may be selected by referring to Tables A-G and host cells comprising any and all of the combinations of nucleic acid sequences encoding the polypeptides set forth in Tables A-G are specifically included herein.

As hereinbefore mentioned, in other embodiments, the living cells naturally produce one or more of the tabersonine-catharanthine synthesis intermediates or tabersonine-catharanthine synthesis derivatives of the present disclosure, however the living cells are modulated in such a manner that the levels of one or more of the tabersonine-catharanthine synthesis intermediates or tabersonine-catharanthine synthesis derivatives, or tabersonine or catharanthine produced in the cells is modulated, without heterologous introduction of any of the aforementioned enzymes in such living cells.

Such modulations may be achieved by a variety of modification techniques, including, but not limited to, the modulation of one or more of the enzymatic activities of SGD; GS; GO; REDOX 1; REDOX 2; SAT; HL1; and HL2, for example by modulating the native nucleic acid sequences encoding SGD; GS; GO; REDOX 1; REDOX 2; SAT; HL1; and HL2, for example by gene silencing methodologies, such as antisense methodologies; or by the use of modification techniques resulting in modulation of activity of the enzymes using for example site directed mutagenesis, targeted mutagenesis, random mutagenesis, virus-induced gene silencing, the addition of organic solvents, gene shuffling or a combination of these and other techniques known to those of skill in the art, each methodology designed to alter the activity of the enzymes of SGD; GS; GO; REDOX 1; REDOX 2; SAT; HL1; and HL2, in such a manner that the accumulation of one or more of tabersonine, catharanthine, the tabersonine-catharanthine intermediates or the tabersonine-catharanthine synthesis derivatives in the living cells increases. Thus the present disclosure further includes embodiments which involve modulating living cells by reducing the production of HL2 in order to produce monooxygenated geissoschizine; modulating living cells by reducing the production of HL2 in order to produce O-acetylstemmadenine; modulating living cells by reducing the production of HL1 in order to produce O-acetylstemmadenine; modulating living cells by reducing the production of HL1 in order to produce monooxygenated geissoschizine; modulating living cells by reducing the production of SAT in order to produce monooxygenated geissoschizine; modulating living cells by reducing the production of SAT in order to produce stemmadenine; modulating living cells by reducing the production of REDOX 1 in order to produce monooxygenated geissoschizine and/or akuammicine; modulating living cells by reducing the production of REDOX 2 in order to produce monooxygenated geissoschizine; modulating living cells by reducing the production of REDOX 2 in order to produce MIA1 and/or MIA2; modulating living cells by reducing the production of GO in order to produce geissoschizine and/or ajmalicine; modulating living cells by reducing the production of GS in order to produce 4,21-dehydrogeissoschizine; and modulating living cells by reducing the production of SGD in order to produce strictosidine. Thus it will be clear that in accordance with the foregoing embodiments, tabersonine-catharanthine synthesis intermediates may be produced by inhibiting an enzyme that converts the desired tabersonine-catharanthine synthesis intermediate and providing the tabersonine-catharanthine synthesis intermediate immediately upstream (as depicted in FIG. 2) of the desired tabersonin-catharanthine synthesis intermediate under conditions that permit the production of the desired tabersonine-catharanthine synthesis intermediate from the immediate upstream compound. Thus, strictly by way of example, one may select a plant comprising the entire synthesis pathway depicted in FIG. 2 (*Catharanthus roseus*, for example), and inhibit GO in such plant, thereby providing 4,21-dehydrogeissoschizine under conditions that permit the production of geissoschizine therefrom; or, and again, strictly by way of example, one may select a plant comprising the entire synthesis pathway depicted in FIG. 2 (*Catharanthus roseus*, for example), and inhibit GS in such plant, thereby providing strictosidine under conditions that permit the production of 4,21-dehydrogeissoschizine therefrom.

Provided herein is further a method for preparing a tabersonine-catharanthine pathway precursor compound selected from the group of tabersonine-catharanthine precursors consisting of monooxygenated geissoschizine, geissoschizine, 4,21-dehydrogeissoschizine and strictosidine comprising:
(a) providing a chimeric nucleic acid sequence comprising (i) one or more nucleic acid sequences complementary to all or a portion of the mRNA synthesized by the nucleic acid sequence encoding the polypeptides selected from the group of polypeptides consisting of SGD; GS; GO; REDOX 1; REDOX 2; SAT; HL1; and HL2; and (ii) one or more elements capable of controlling transcription of the complementary nucleic acid sequence, wherein the chimeric nucleic acid sequence is capable of producing an antisense RNA complementary to all or a portion of the mRNA of the nucleic acid sequence encoding the polypeptides selected from the group of polypeptides consisting of SGD; GS; GO; REDOX 1; REDOX 2; SAT; HL1; and HL2;
(b) introducing the chimeric nucleic acid sequence into a host cell;
(c) growing the host cell to produce the antisense RNA and inhibit synthesis of the polypeptide selected from the group of polypeptides consisting of SGD; GS; GO; REDOX 1; REDOX 2; SAT; HL1; and HL2, and to produce one or more tabersonine-catharanthine pathway precursor compound selected from the group of tabersonine-catharanthine pathway precursor compounds consisting of monooxygenated geissoschizine, geissoschizine, 4,21-dehydrogeissoschizine and strictosidine; and
(d) recovering tabersonine-catharanthine pathway precursor compound selected from the group of tabersonine-catharanthine pathway precursor compounds consisting of monooxygenated geissoschizine, geissoschizine, 4,21-dehydrogeissoschizine and strictosidine.

In further aspects, the nucleic acid sequences encoding SGD, including the nucleic acid sequence set forth in SEQ ID NO: 8, and the nucleic acid sequences encoding GS, including the nucleic acid sequence set forth in SEQ ID NO: 9; SEQ ID NO 17; SEQ ID NO 18; and SEQ ID NO 19, and the nucleic acid sequences encoding GO, including the nucleic acid sequence set forth in SEQ ID NO: 10; SEQ ID NO 20; SEQ ID NO 21; and SEQ ID NO 22, and the nucleic acid sequences encoding REDOX 1, including the nucleic acid sequence set forth in SEQ ID NO: 11; SEQ ID NO 23; SEQ ID NO 24; and SEQ ID NO 25, and the nucleic acid sequences encoding REDOX 2, including the nucleic acid sequence set forth in SEQ ID NO: 12; SEQ ID NO 26; SEQ ID NO 27; and SEQ ID NO 28, and the nucleic acid sequences encoding SAT, including the nucleic acid sequence set forth in SEQ ID NO: 15; SEQ ID NO 29; SEQ ID NO 30; and SEQ ID NO 31, and the nucleic acid sequences encoding HL1, including the nucleic acid sequence set forth in SEQ ID NO: 13 and the nucleic acid sequences encoding HL2, including the nucleic acid sequence set forth in SEQ ID NO: 14; SEQ ID NO: 32; SEQ ID NO: 33; SEQ ID NO: 34; SEQ ID NO 35; and SEQ ID NO 36, may be used to produce a cell that has modulated levels of expression of SGD, GS, GO, REDOX 1, REDOX 2, SAT, HL1 or HL2, respectively. Such a cell may be a plant cell natively expressing SGD, GS, GO, REDOX 1, REDOX 2, SAT HL1 or HL2 and, may for example be plant cell obtainable from *Catharanthus roseus, Vinca minor, Amsonia hubrichtii* and *Tabernaemontana elegans*. Thus the present disclosure further provides a method for modulating expression of nucleic acid sequences in a cell naturally expressing SGD, GS, GO, REDOX 1, REDOX 2, SAT, HL1 or HL2 comprising:
(a) providing a cell naturally expressing SGD, GS, GO, REDOX 1, REDOX 2, SAT, HL1 or HL2;
(b) mutagenizing the cell;
(c) growing the cell to obtain a plurality of cells; and
(d) determining if the plurality of cells comprises a cell comprising modulated levels of SGD, GS, GO, REDOX 1, REDOX 2, SAT, HL1 or HL2.

In preferred embodiments, the method further comprises a step (e) as follows:
(e) selecting a cell comprising modulated levels of SGD, GS, GO, REDOX 1, REDOX 2, SAT, HL1 or HL2 and growing such cell to obtain a plurality of cells.

In further preferred embodiments, plant seed cells are used to perform the mutagenesis. Mutagenic agents that may be used are chemical agents, including without limitation, base analogues, deaminating agents, alkylating agents, intercalating agents, transposons, bromine, sodium azide, ethyl methanesulfonate (EMS) as well as physical agents, including, without limitation, radiation, such as ionizing radiation and UV radiation. Thus the present disclosure further provides a method for producing a seed setting plant comprising modulated expression of nucleic acid sequences in a cell naturally expressing SGD, GS, GO, REDOX 1, REDOX 2, SAT, HL1 or HL2, the method comprising:
(a) providing a seed setting plant naturally expressing SGD, GS, GO, REDOX 1, REDOX 2, SAT, HL1 or HL2;
(b) mutagenizing seed of the plant to obtain mutagenized seed;
(c) growing the mutagenized seed into the next generation mutagenized plants capable of setting the next generation seed; and
(d) obtaining the next generation seed, or another portion of the mutagenized plants, and analyzing if the next generation plants or next generation seed exhibits modulated SGD, GS, GO, REDOX 1, REDOX 2, SAT, HL1 or HL2 expression.

In preferred embodiments, a plurality of generations of plants and/or seed may be obtained, and portions of plants and/or seed in any or all of such generations may be analyzed. Analysis is typically performed by comparing expression levels (e.g. RNA levels or protein levels) in non-mutagenized (wild type) plants or seed with expression in mutagenized plants or seed. In further preferred embodiments, the analysis in step (d) may be performed by analyzing heteroduplex formation between wildtype DNA and mutated DNA. Thus in preferred embodiments, the analysing in step (d) comprises
i. extracting DNA from mutated plants;
ii. amplifying a portion of the DNA comprising a nucleic acid sequence encoding SGD, GS, GO, REDOX 1, REDOX 2, SAT, HL1 or HL2 to obtain amplified mutated DNA;
iii. extracting DNA from wild type plants;
iv. mixing the DNA from wild type plants with the amplified mutated DNA and form a heteroduplexed polynucleotide;
v. incubating the heteroduplexed polynucleotide with a single stranded restriction nuclease capable of restricting at a region of the heteroduplexed polynucleotide that is mismatched; and
vi. determining the site of mismatch in the heteroduplex polynucleotide.

In preferred embodiments, the nucleic acid sequence encoding SGD that is used is set forth in SEQ ID NO: 8.

In preferred embodiments, the nucleic acid sequence encoding GS that is used is set forth in SEQ ID NO: 9; SEQ ID NO: 17; SEQ ID NO: 18; or SEQ ID NO 19.

In preferred embodiments, the nucleic acid sequence encoding GO that is used is set forth in SEQ ID NO: 10; SEQ ID NO: 20; SEQ ID NO: 21; or SEQ ID NO 22.

In preferred embodiments, the nucleic acid sequence encoding REDOX 1 that is used is set forth in SEQ ID NO: 11; SEQ ID NO: 23; SEQ ID NO: 24; or SEQ ID NO 25.

In preferred embodiments, the nucleic acid sequence encoding REDOX 2 that is used is set forth in SEQ ID NO: 12; SEQ ID NO: 26; SEQ ID NO: 27; or SEQ ID NO 28.

In preferred embodiments, the nucleic acid sequence encoding SAT that is used is set forth in SEQ ID NO: 15; SEQ ID NO: 29; SEQ ID NO: 30; or SEQ ID NO 31.

In preferred embodiments, the nucleic acid sequence encoding HL1 that is used is set forth in SEQ ID NO: 13.

In preferred embodiments, the nucleic acid sequence encoding HL2 that is used is set forth in SEQ ID NO: 14; SEQ ID NO: 32; SEQ ID NO: 33; SEQ ID NO: 34; SEQ ID NO: 35; or SEQ ID NO 36.

In further aspects, the nucleic acid sequences encoding may be used to produce a cell that has modulated levels of expression of SGD, GS, GO, REDOX 1, REDOX 2, SAT HL1 or HL2 by gene silencing. Thus the present disclosure further includes a method of reducing the expression of SGD, GS, GO, REDOX 1, REDOX 2, SAT, HL1 or HL2 in a cell, comprising:
(a) providing a cell expressing SGD, GS, GO, REDOX 1, REDOX 2, SAT, HL1 or HL2; and
(b) silencing expression of SGD, GS, GO, REDOX 1, REDOX 2, SAT, HL1 or HL2 in the cell.

In preferred embodiments, the cell is a plant cell, including *Catharanthus roseus*. A preferred methodology to silence SGD, GS, GO, REDOX 1, REDOX 2, SAT, HL1 or HL2 that is used is virus induced gene silencing (known to the art as VIGS). In general, in plants infected with unmodified viruses, the viral genome is targeted. However, when viral vectors have been modified to carry inserts derived from host genes (e.g. portions of sequences encoding SGD, GS, GO, REDOX 1, REDOX 2, SAT, HL1 or HL2), the process is additionally targeted against the corresponding mRNAs. Thus the present disclosure further includes a method of producing a plant expressing reduced levels of SGD, GS, GO, REDOX 1, REDOX 2, SAT, HL1 or HL2, the method comprising
(a) providing a plant expressing codeine SGD, GS, GO, REDOX 1, REDOX 2, SAT, HL1 or HL2; and
(b) reducing expression of SGD, GS, GO, REDOX 1, REDOX 2, SAT, HL1 or HL2 in the plant using virus induced gene silencing.

The hereinbefore mentioned methods to modulate expression levels of SGD, GS, GO, REDOX 1, REDOX 2, SAT, HL1 or HL2 may result in modulations in the levels of plant terpenoid indole alkaloid compounds, in plants including, without limitation, strictosidine; 4,21-dehydrogeissoschizine; geissoschizine; monooxygenated geissoschizine; stemmadenine, tabersonine and catharanthine. Thus the present disclosure includes the use of the methodologies to modify the levels of plant alkaloids in a plant naturally capable of producing plant alkaloids. Preferably, such plants belong to the plant genus of *Catharanthus*.

In yet further aspects of the present disclosure, the nucleic acid sequences encoding SGD, GS, GO, REDOX 1, REDOX 2, SAT, HL1 or HL2 may be used to genotype plants. Preferably, the plant is a member belonging to the plant genus of *Catharanthus*. In general, genotyping provides a means of distinguishing homologs of a chromosome pair and can be used to identify segregants in subsequent generations of a plant population. Molecular marker methodologies can be used for phylogenetic studies, characterizing genetic relationships among plant varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methodologies, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21. The particular method of genotyping in accordance with the present disclosure may involve the employment of any molecular marker analytic technique including, but not limited to, restriction fragment length polymorphisms (RFLPs). RFLPs reflect allelic differences between DNA restriction fragments caused by nucleotide sequence variability. As is known to those of skill in the art, RFLPs are typically detected by extraction of plant genomic DNA and digestion of the genomic DNA with one or more restriction enzymes. Typically, the resulting fragments are separated according to size and hybridized with a nucleic acid probe. Restriction fragments from homologous chromosomes are revealed. Differences in fragment size among alleles represent an RFLP. Thus, the present disclosure further provides a means to follow segregation of a portion or genomic DNA encoding SGD, GS, GO, REDOX 1, REDOX 2, SAT, HL1 or HL2, as well as chromosomal nucleic acid sequences genetically linked to these SGD, GS, GO, REDOX 1, REDOX 2, SAT, HL1 or HL2 encoding nucleic acid sequences using such techniques as RFLP analysis. Linked chromosomal nucleic sequences are within 50 centiMorgans (cM), often within 40 or 30 cM, preferably within 20 or 10 cM, more preferably within 5, 3, 2, or 1 cM of a genomic nucleic acid sequence encoding SGD, GS, GO, REDOX 1, REDOX 2, SAT, HL1 or HL2. Thus, in accordance with the present disclosure the SGD, GS, GO, REDOX 1, REDOX 2, SAT, HL1 or HL2 encoding sequences of the present disclosure may be used as markers to evaluate in a plant population the segregation of nucleic acid sequences genetically linked thereto. Preferably, the plant population comprises or consists of plants belonging to the plant families *Catharanthus*.

In accordance with the present disclosure, the nucleic acid probes employed for molecular marker mapping of plant nuclear genomes selectively hybridize, under selective hybridization conditions, to a genomic sequence encoding SGD, GS, GO, REDOX 1, REDOX 2, HL1 or HL2. In preferred embodiments, the probes are selected from the nucleic acid sequences encoding SGD, GS, GO, REDOX 1, REDOX 2, SAT, HL1 or HL2 provided by the present disclosure. Typically, these probes are cDNA probes. Typically these probes are at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid plant chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves a polynucleotide at a specific nucleotide sequence.

Other methods of differentiating polymorphic (allelic) variants of the nucleic acid sequences of the present disclosure can be used by utilizing molecular marker techniques well known to those of skill in the art, including, without limitation: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include, without limitation, clamped denaturing gel electrophoresis (CDGE); heteroduplex analysis (HA), and chemical mismatch cleavage (CMC). Thus, the present disclosure further provides a method of genotyping comprising the steps of contacting, under stringent hybridization conditions, a sample suspected of comprising a nucleic acid encoding SGD, GS, GO, REDOX 1, REDOX 2, SAT, HL1 or HL2, with a nucleic acid probe capable of hybridizing thereto. Generally, the sample is a plant sample; preferably, a sample suspected of comprising a *Catharanthus roseus* nucleic acid sequence encoding SGD, GS, GO, REDOX 1, REDOX 2, SAT, HL1 or HL2 (e.g., gene, mRNA). The nucleic acid probe selectively hybridizes, under stringent conditions, to a subsequence of the nucleic acid sequence encoding SGD, GS, GO, REDOX 1, REDOX 2, SAT, HL1 or HL2 comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a portion of a nucleic acid sequence encoding SGD, GS, GO, REDOX 1, REDOX 2, SAT, HL1 or HL2.

In embodiments hereof where tabersonine-catharanthine synthesis derivatives are formed from tabersonine-catharanthine synthesis intermediates, the aforementioned generally described in vivo reaction conditions will be equally applicable and implementable with reference to FIG. 17.

Nucleotide Sequences and Polypeptide Sequences

In one embodiment, the present disclosure provides a polypeptide comprising one or more of the polypeptide sequences set forth in SEQ ID NO: 1; SEQ ID NO: 2; SEQ ID NO: 3; SEQ ID NO: 4; SEQ ID NO: 5; SEQ ID NO: 6; and SEQ ID NO: 7; SEQ ID NO: 16; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; and SEQ ID NO: 56.

In one embodiment, the present disclosure provides a polynucleotide, comprising one or more of the nucleotide sequences set forth in SEQ ID NO: 8; SEQ ID NO: 9; SEQ ID NO: 10; SEQ ID NO: 11; SEQ ID NO: 12; SEQ ID NO: 13; SEQ ID. NO: 14; SEQ ID NO: 15; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; and SEQ ID NO: 36.

In some embodiments, the polynucleotides and polypeptides are substantially pure.

In some embodiments, the polynucleotides and polypeptides are substantially free of native plant cell constituents.

In some embodiments, the polynucleotide and polypeptides are obtained in a formulation suitable to perform the methods of the present disclosure, including, without limitation, in the case of the polypeptides in a form suitable to perform the in vitro or in vivo methods of the present disclosure.

Use of Tabersonine-Catharanthine Pathway Enzymes

In one aspect the present disclosure further includes uses of enzymes, including for the purpose of catalytically convert certain substrate terpenoid indole alkaloid compounds to certain product terpenoid indole alkaloid compounds.

In one embodiment, the present disclosure provides a use of SGD as an enzyme to catalytically convert strictosidine or strictosidine aglycone to form 4,21-dehydrogeissoschizine.

In one embodiment, the present disclosure provides a use of SGD as an enzyme to catalytically convert strictosidine to form cathenamine and/or ajmalicine.

In one embodiment, the present disclosure provides a use of GS as an enzyme to catalytically convert 4,21-dehydrogeissoschizine to form geissoschizine.

In one embodiment, the present disclosure provides a use of GS as an enzyme to catalytically convert 4,21-dehydrogeissoschizine to form pericyclivine and/or perivine.

In one embodiment, the present disclosure provides a use of GO as an enzyme to catalytically convert geissoschizine to form monooxygenated geissoschizine.

In one embodiment, the present disclosure provides a use of REDOX 1 and REDOX 2 as enzymes to catalytically convert monooxygenated geissoschizine to form stemmadenine.

In one embodiment, the present disclosure provides a use of a mixture of enzymes comprising REDOX1, REDOX 2, SAT and HL1 to catalytically convert monooxygenated geissoschizine to form catharanthine.

In one embodiment, the present disclosure provides a use of a mixture of enzymes comprising REDOX1, REDOX 2, SAT and HL2 to catalytically convert monooxygenated geissoschizine to form tabersonine.

In one embodiment, the present disclosure provides a use of a mixture of enzymes comprising GO, REDOX1, REDOX 2, SAT and HL2 to catalytically convert geissoschizine to form tabersonine.

In one embodiment, the present disclosure provides a use of a mixture of enzymes comprising GO, REDOX1, REDOX 2, SAT and HL1 to catalytically convert geissoschizine to form catharanthine.

In one embodiment, the present disclosure provides a use of a mixture of enzymes comprising GO, REDOX1, REDOX 2, and SAT to catalytically convert geissoschizine to form O-acetylstemmadenine.

In one embodiment, the present disclosure provides a use of a mixture of enzymes comprising GO, REDOX1, and REDOX 2 to catalytically convert geissoschizine to form stemmadenine.

In one embodiment, the present disclosure provides a use of a mixture of enzymes comprising GO and REDOX 2 to catalytically convert geissoschizine to form MIA1 and/or MIA2.

In one embodiment, the present disclosure provides a use of REDOX 2 as an enzyme to catalytically convert geissoschizine to form isositsirikine.

In one embodiment, the present disclosure provides a use of REDOX 1 as an enzyme to catalytically convert monooxygenated geissoschizine to form MIA1 and/or MIA2.

In one embodiment, the present disclosure provides a use of a mixture of enzymes comprising REDOX 1 and REDOX 2 to catalytically convert monooxygenated geissoschizine to form stemmadenine.

In one embodiment, the present disclosure provides a use of a mixture of enzymes comprising REDOX 1, REDOX 2 and SAT to catalytically convert monooxygenated geissoschizine to form O-acetylstemmadenine.

In one embodiment, the present disclosure provides a use of SAT as enzymes to catalytically convert stemmadenine to form O-acetylstemmadenine.

In some embodiments, the use is a use to convert the substrate terpenoid indole alkaloid compound in vitro to the product terpenoid indole alkaloid compound.

In some embodiments, the use is a use to convert the substrate terpenoid indole alkaloid compound in vivo to the product terpenoid indole alkaloid compound.

In some embodiments, the reaction mixture is substantially free of plant constituents, other than the enzymes and substrate, and product terpenoid indole alkaloid compounds, including, without limitation tabersonine, catharanthine, tabersonine-catharanthine synthesis intermediates and tabersonine-catharanthine synthesis derivatives.

Use of Tabersonine, Catharanthine, Tabersonine-Catharanthine Synthesis Intermediates and Tabersonine-Catharanthine Synthesis Derivatives In accordance with the present disclosure certain substrate terpenoid indole alkaloids may be used as a substrate to obtain certain product terpenoid indole alkaloids.

In one embodiment, the present disclosure provides a use of strictosidine as a substrate for catalytic conversion to form 4,21-dehydrogeissoschizine in a reaction mixture comprising SGD.

In one embodiment, the present disclosure provides a use of 4,21-dehydrogeissoschizine as a substrate for catalytic conversion to form geissoschizine in a reaction mixture comprising GS.

In one embodiment, the present disclosure provides a use of geissoschizine as a substrate for catalytic conversion to form monooxygenated geissoschizine in a reaction mixture comprising GO.

In one embodiment, the present disclosure provides a use of geissoschizine as a substrate for catalytic conversion to form MIA1 and/or MIA 2 in a reaction mixture comprising GO, and REDOX 1.

In one embodiment, the present disclosure provides a use of geissoschizine as a substrate for catalytic conversion to form stemmadenine in a reaction mixture comprising GO, REDOX 1, and REDOX 2.

In one embodiment, the present disclosure provides a use of geissoschizine as a substrate for catalytic conversion to form O-acetylstemmadenine in a reaction mixture comprising GO, REDOX 1, REDOX 2, and SAT.

In one embodiment, the present disclosure provides a use of geissoschizine as a substrate for catalytic conversion to form tabersonine in a reaction mixture comprising GO, REDOX 1, REDOX 2, SAT, and HL2.

In one embodiment, the present disclosure provides a use of geissoschizine as a substrate for catalytic conversion to form catharanthine in a reaction mixture comprising GO, REDOX 1, REDOX 2, SAT, and HL1.

In one embodiment, the present disclosure provides a use of monooxygenated geissoschizine as a substrate for catalytic conversion to form stemmadenine in a reaction mixture comprising REDOX 1 and REDOX 2.

In one embodiment, the present disclosure provides a use of monooxygenated geissoschizine as a substrate for catalytic conversion to form O-acetylstemmadenine in a reaction mixture comprising REDOX 1, REDOX 2 and SAT.

In one aspect, the present disclosure provides a use of monooxygenated geissoschizine as a substrate for catalytic conversion to form catharanthine in a reaction mixture comprising REDOX 1, REDOX 2, SAT and HL1.

In one aspect, the present disclosure provides a use of monooxygenated geissoschizine as a substrate for catalytic conversion to form tabersonine in a reaction mixture comprising REDOX 1, REDOX 2, SAT and HL2.

In one embodiment, the present disclosure provides a use of stemmadenine as a substrate for catalytic conversion to form O-acetylstemmadenine in a reaction mixture comprising SAT.

In one embodiment, the present disclosure provides a use of geissoschizine as a substrate for catalytic conversion to form isositsirikine in a reaction mixture comprising REDOX 2.

In one embodiment, the present disclosure provides a use of monooxygenated geissoschizine as a substrate for catalytic conversion to form MIA1 and/or MIA2 in a reaction mixture comprising REDOX 1.

In some embodiments, the reaction mixture is prepared for the performance of an in vitro reaction.

In some embodiments, the reaction mixture is prepared for the performance of an in vivo reaction.

In some embodiments, the reaction mixture is substantially free of plant constituents, other than the enzymes and substrate and product terpenoid indole alkaloids.

The terpenoid indole alkaloids obtained in accordance with the present disclosure further may be used as agents to prepare a pharmaceutical drug, therapeutic agent or medicinal agent. In particular embodiments, the terpenoid indole alkaloids of the present disclosure may be used to prepare chemotherapeutic agents. Furthermore in particular embodiments, the terpenoid indole alkaloids obtained in accordance with the present disclosure may be used to prepare vinblastine and vincristine. FIG. 4 in this regard depicts the preparation of vindoline from tabersonine (FIG. 4A), and the preparation of vincristine and vinblastine from vindoline and catharanthine (FIG. 4B). The foregoing syntheses may be performed chemically or biosynthetically (Zhu et al., Pharmacogn. Rev. 2015 9 (17) 24-28; Verma, A. et al. Molecules 2007 12 1307-1315).

In further particular embodiments, the tabersonine-catharanthine synthesis derivative akuammicine may be used as a receptor agonist, including as a kappa-opioid receptor agonist (Menzies J R et al. (1998) Opioid activity of alkaloids extracted from *Picralima nitida* (fam. Apocynaceae) *Eur. J. Pharmacol.* 350(1):101-8).

In further particular embodiments, perivine and stemmadenine may be used as a hypotensive pharmacological agent (Perera P. et al. (1985) Muscle relaxant activity and hypotensive activity of some *Tabernaemontana* alkaloids. *J. Ethnopharmacol.* 13(2):165:73).

In further particular embodiments, isositsirikine may be used as antineoplastic pharmacological agent (Mukhopadhyay S. et al. (1983) *Catharanthus* alkaloids XXXVII. 16-Epi-Z-isositsirikine, a monomeric indole alkaloid with antineoplastic activity from *Catharanthus roseus* and *Rhazya stricta. J. Nat. Prod.* 46(3):409-13).

In further particular embodiments, tabersonine may be used to inhibit amyloid gibril formation and may be used as a medicinal agent to treat Alzheimer disease (*ACS Chem. Neurosci.* 2015, 6, 879-888)

In further particular embodiments, the tabersonine-catharanthine synthesis derivative ajmalicine may be used as a medicinal agent to modulate high blood pressure.

EXAMPLES

Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

Example 1—In Vitro Production of Geissoschizine

Figure 5:
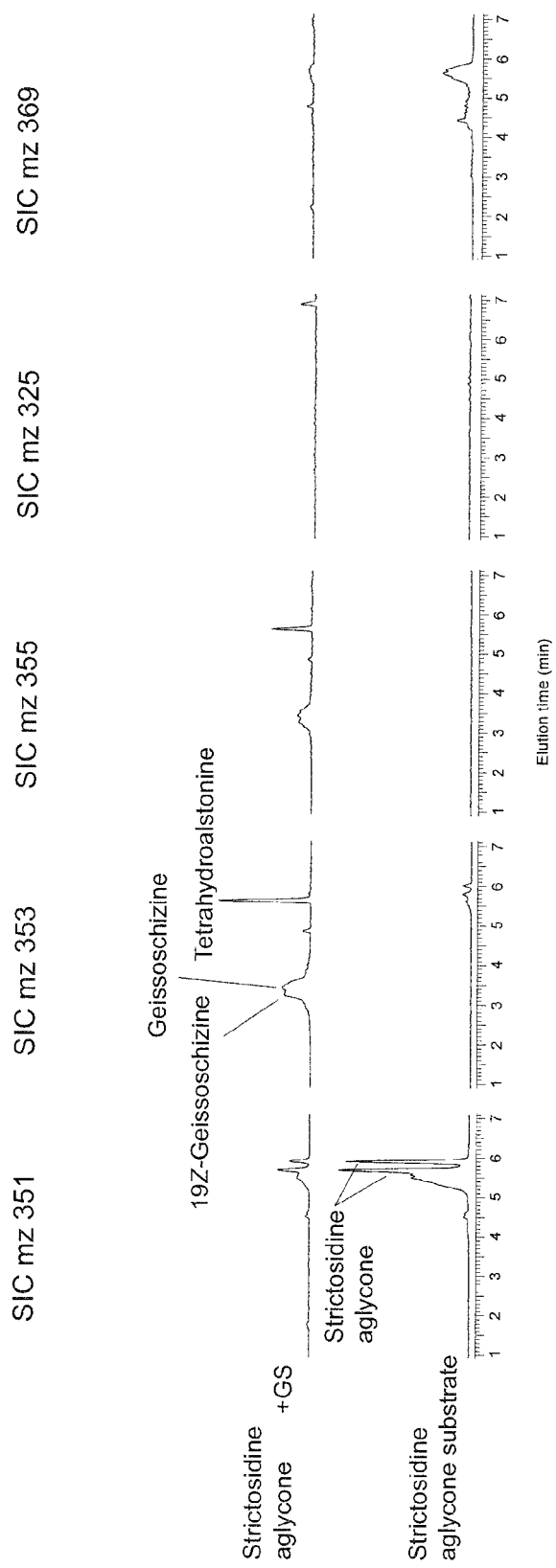
FIG. 5 depicts results obtained in certain experiments designed to evaluate the production of geissoschizine using GS as a catalyzing enzyme. Shown is an LC-MS chromatogram showing the conversion of strictosidine aglycone to geissoschizine as selected ion chromatogram (SIC) SIC m/z 353.

This example illustrates the in vitro production of geissoschizine using GS as a catalyzing enzyme. In vitro reactions (200 µl) containing 20 mM Tris pH 7.5, 1 mM NADPH, 5 µg strictosidine aglycone and 2.5 µg of recombinantly E. coli produced and purified GS were prepared. Reactions were set up to take place at 30° C. for 1 hr and the reaction products were dissolved in methanol and analyzed by LC-MS as selected ion chromatogram (SIC). As shown in FIG. 5, under the reaction conditions GS catalyzes the production of geissoschizine, as well as its isomer (m/z 353). In addition, tetrahydroalstonine is detected as a byproduct. It is noted however that in that in VIGS-GO plants only geissoschizine accumulates (see: Example 8).

Example 2—In Vitro Production of Monooxygenated Geissoschizine

Figure 6:
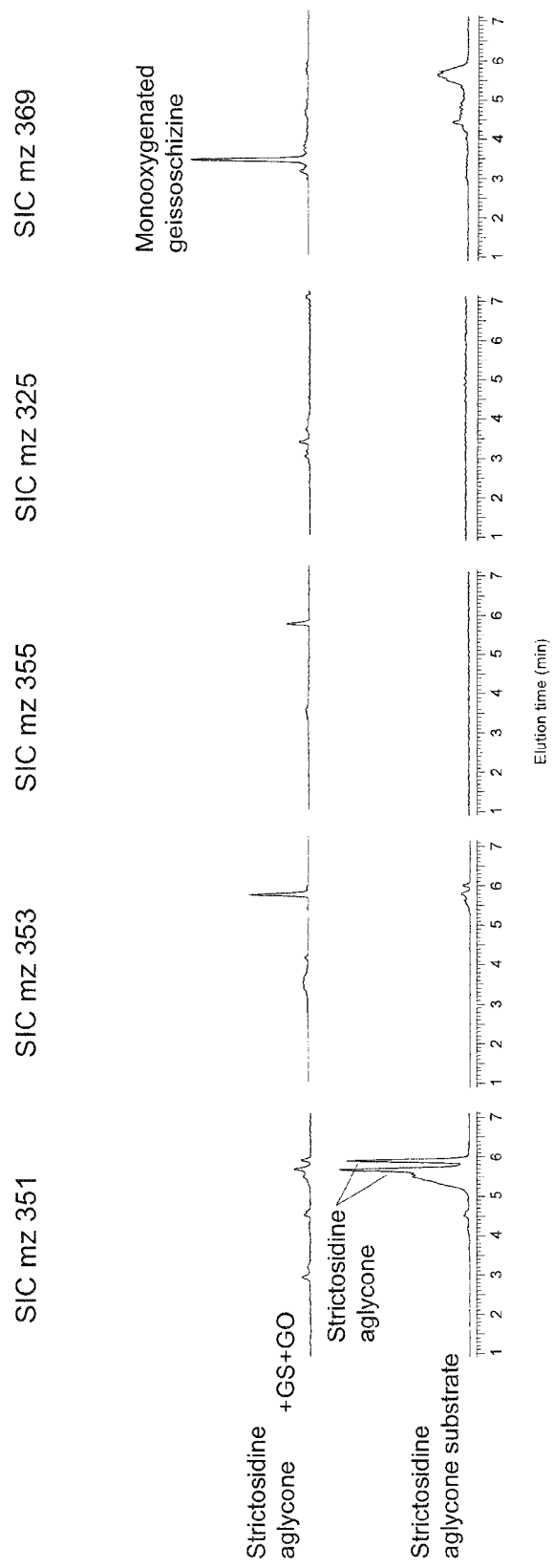
FIG. 6 depicts results obtained in certain experiments designed to evaluate the production of monooxygenated geissoschizine using a mixture of GS and GO as catalyzing enzymes. Shown is an LC-MS chromatogram showing the conversion of strictosidine aglycone to monooxygenated geissoschizine as selected ion chromatogram (SIC) SIC m/z 369.

This example illustrates the in vitro production of monooxygenated geissoschizine using GS and GO as a catalyzing enzymes. In vitro reactions (200 µl) containing 20 mM Tris pH 7.5, 1 mM NADPH, 5 µg strictosidine aglycone and 2.5 µg of each recombinantly produced and purified E. coli GS and 200 mg yeast microsome containing GO were prepared. Reactions were set up to take place at 30° C. for 1 hr and the reaction products were dissolved in methanol and analyzed by LC-MS as selected ion chromatogram (SIC). As shown in FIG. 6, under the reaction conditions the GS and GO enzyme mixture catalyzes the production of monooxygenated geissoschizine. It is noted that monooxygenated geissoschizine also accumulate in VIGS-REDOX 1 plants (see: Example 9)

Example 3—In Vitro Production of Isositsirikine

Figure 7:
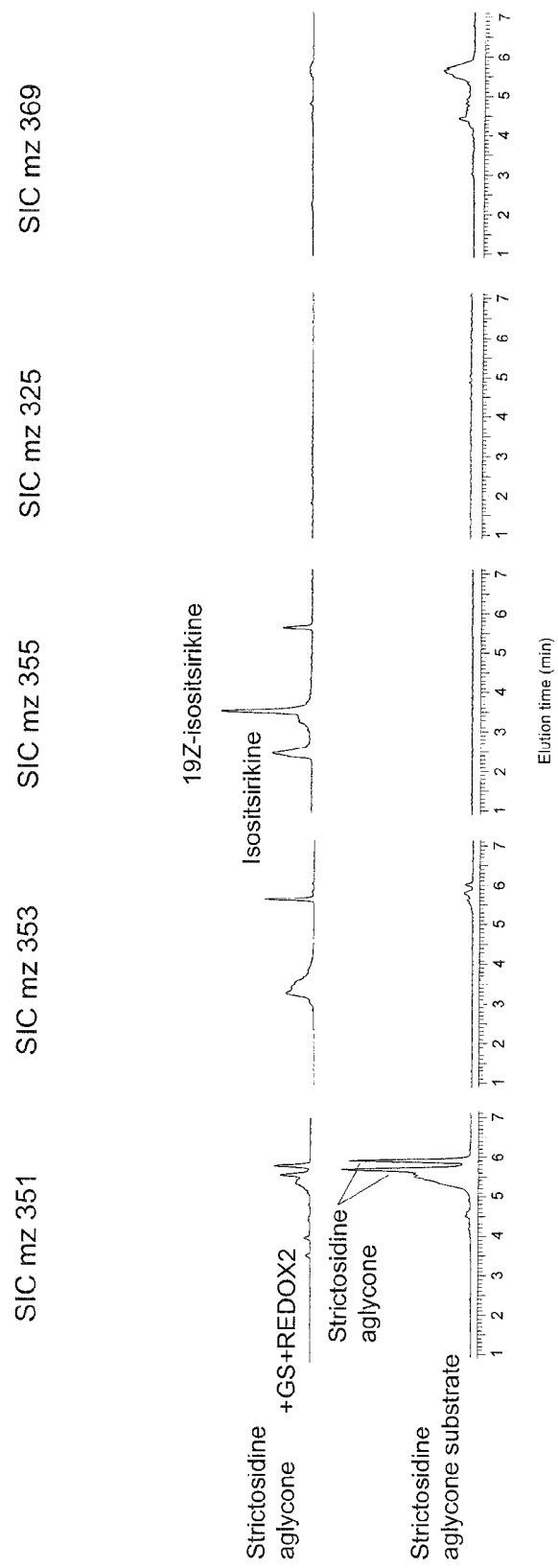
FIG. 7 depicts results obtained in certain experiments designed to evaluate the production of isositsirikine using a mixture of GS and REDOX 2 as catalyzing enzymes. Shown is an LC-MS chromatogram showing the conversion of strictosidine aglycone to isositsirikine as selected ion chromatogram (SIC) SIC m/z 355.

This example illustrates the in vitro production of isositsirikine using GS and REDOX 2 as catalyzing enzymes. In vitro reactions (200 µl) containing 20 mM Tris pH 7.5, 1 mM NADPH, 5 µg strictosidine aglycone and 2.5 µg of each recombinantly E. coli produced and purified GS and REDOX 2 were prepared. Reactions were set up to take place at 30° C. for 1 hr and the reaction products were dissolved in methanol and analyzed by LC-MS as selected ion chromatogram (SIC). As shown in FIG. 7, under the reaction conditions the GS and REDOX 2 enzyme mixture catalyzes the production of two isomeric forms of isositsirikine. It is noted that isositsirikine also accumulate in VIGS-GO plants (see: Example 8).

Figure 8:
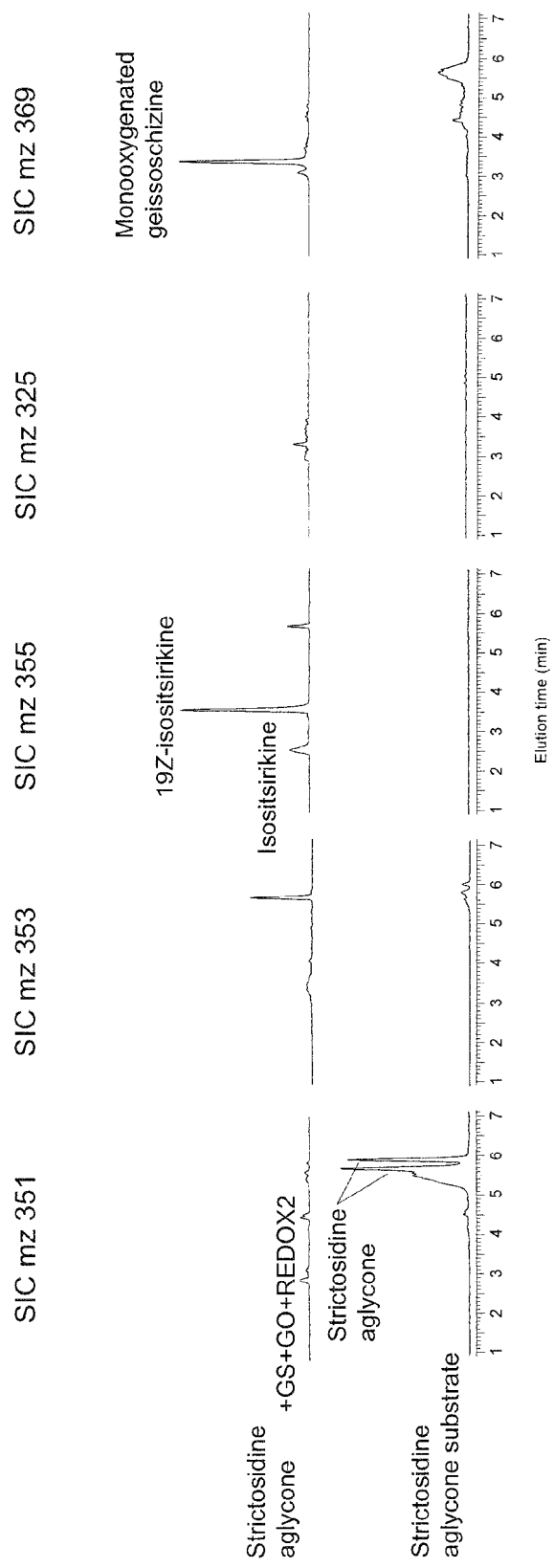
FIG. 8 depicts results obtained in certain experiments designed to evaluate the production of isositsirikine using a mixture of GS, GO and REDOX 2 as catalyzing enzymes. Shown is an LC-MS chromatogram showing the conversion of strictosidine aglycone to isositsirikine as selected ion chromatogram (SIC) SIC m/z 355.

Example 4—In Vitro Production of Isositsirikine and Monooxygenated Geissoschizine This example illustrates the in vitro production of isositsirikine using GS, GO and REDOX 2 as catalyzing enzymes. In vitro reactions (200 µl) containing 20 mM Tris pH 7.5, 1 mM NADPH, 5 µg strictosidine aglycone and 2.5 µg of each recombinantly produced-purified GS (E. coli), REDOX 2 (E. coli), and 200 µg yeast microsome containing GO, were prepared. Reactions were set up to take place at 30° C. for 1 hr and the reaction products were dissolved in methanol and analyzed by LC-MS as selected ion chromatogram (SIC). As shown in FIG. 8, under the reaction conditions the GS, GO and REDOX 2 enzyme mixture catalyzes the simultaneous production of isositsirikine (two isomeric forms), and monooxygenated geissoschizine. It is noted that isositsirikine also accumulate in VIGS-GO plants (see Example 8).

Example 5—In Vitro Production of MIA 1 and MIA 2

Figure 9:
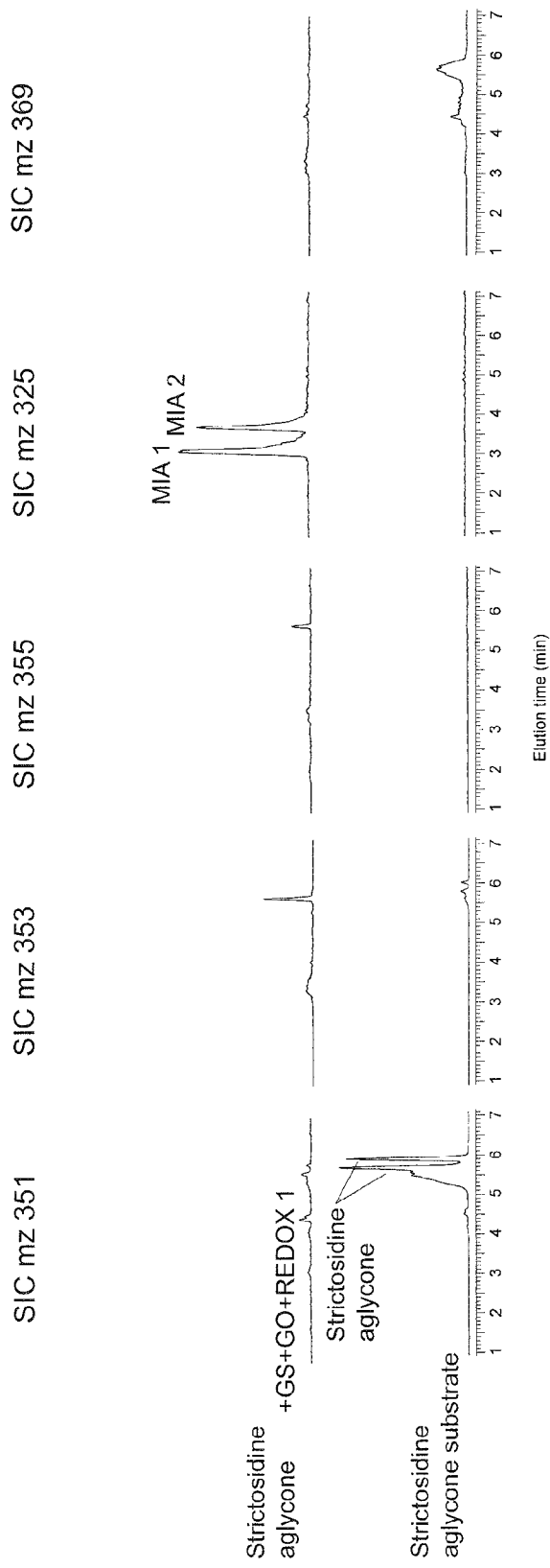
FIG. 9 depicts results obtained in certain experiments designed to evaluate the production of MIA 1 and MIA 2 using a mixture of GS, GO and REDOX 1 as catalyzing enzymes. Shown is an LC-MS chromatogram showing the conversion of strictosidine aglycone to MIA 1 and MIA 2 as selected ion chromatogram (SIC) SIC m/z 325.
Figure 18:
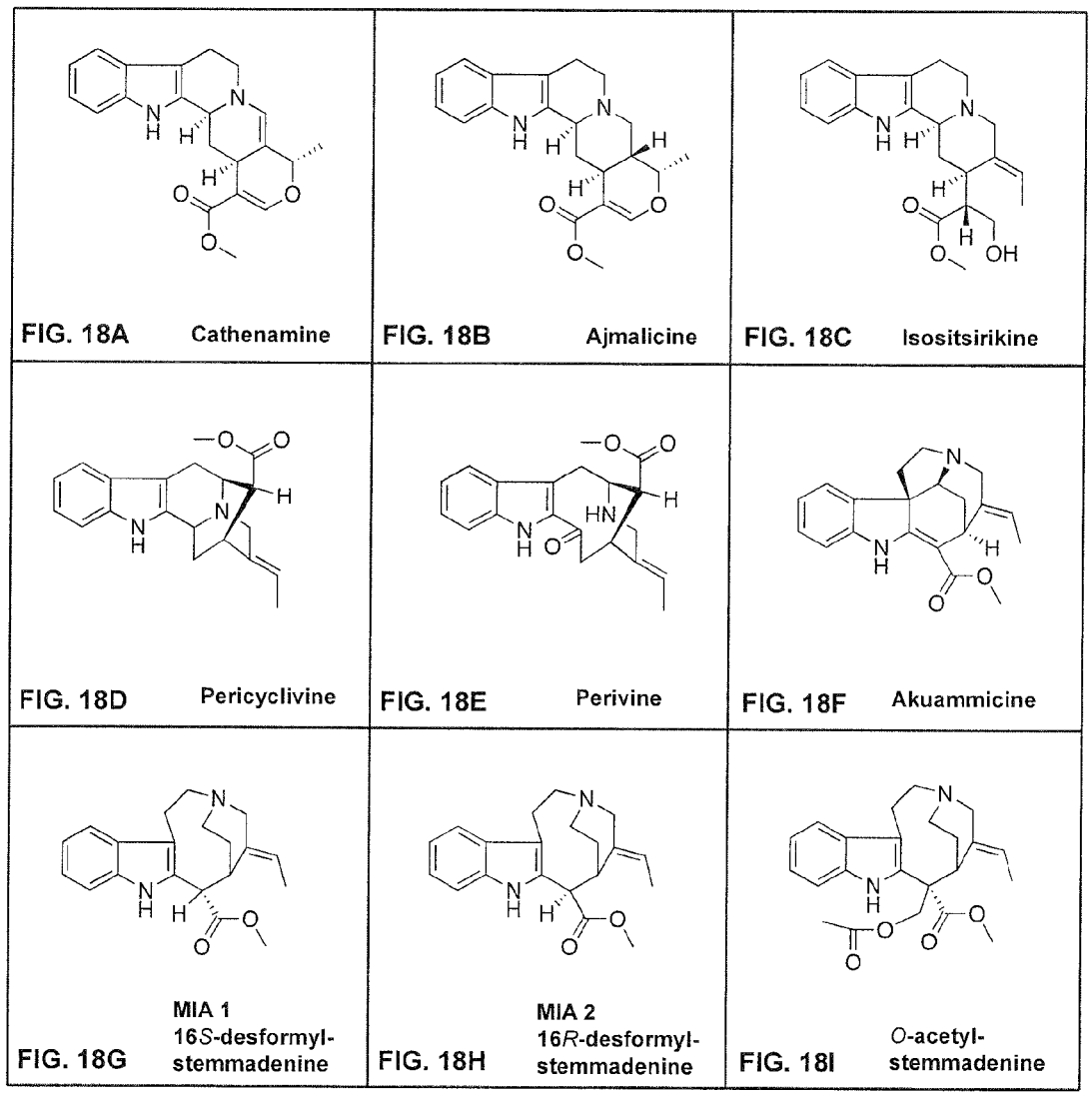
FIG. 18 depicts the chemical structures of certain tabersonine catharanthine intermediate derivatives including cathenamine (FIG. 18A); ajmalicine (FIG. 18B); isositsirikine (FIG. 17C); isositsirikine, pericyclivine and perivine (geissoschizine derivatives) (FIGS. 18C, 18D and 18E, respectively); akuammicine, MIA1, MIA2 and O-acetylstemmadenine (monooxygenated geissoschizine derivatives) (FIGS. 18F, 18G, 18H and 18I, respectively).

This example illustrates the in vitro production of MIA1 and MIA 2 using GS, GO, and REDOX 1 as a catalyzing enzymes. The chemical structures of MIA 1 and MIA 2 are shown in FIG. 18. In vitro reactions (200 µl) containing 20 mM Tris pH 7.5, 1 mM NADPH, 5 µg strictosidine aglycone and 2.5 µg of each recombinantly produced GS (E. coli), REDOX 1 (E. coli), and 200 µg yeast microsome containing GO were prepared. Reactions were set up to take place at 30° C. for 1 hr and the reaction products were dissolved in methanol and analyzed by LC-MS as selected ion chromatogram (SIC). As shown in FIG. 9, under the reaction conditions the GS, GO and REDOX 1 enzyme mixture catalyzes the production of MIA 1 and MIA 2. It is noted that MIA 1 and MIA 2 also accumulate in VIGS-REDOX 2 plants (see: Example 9).

Example 6—In Vitro Production of Stemmadenine

Figure 10:
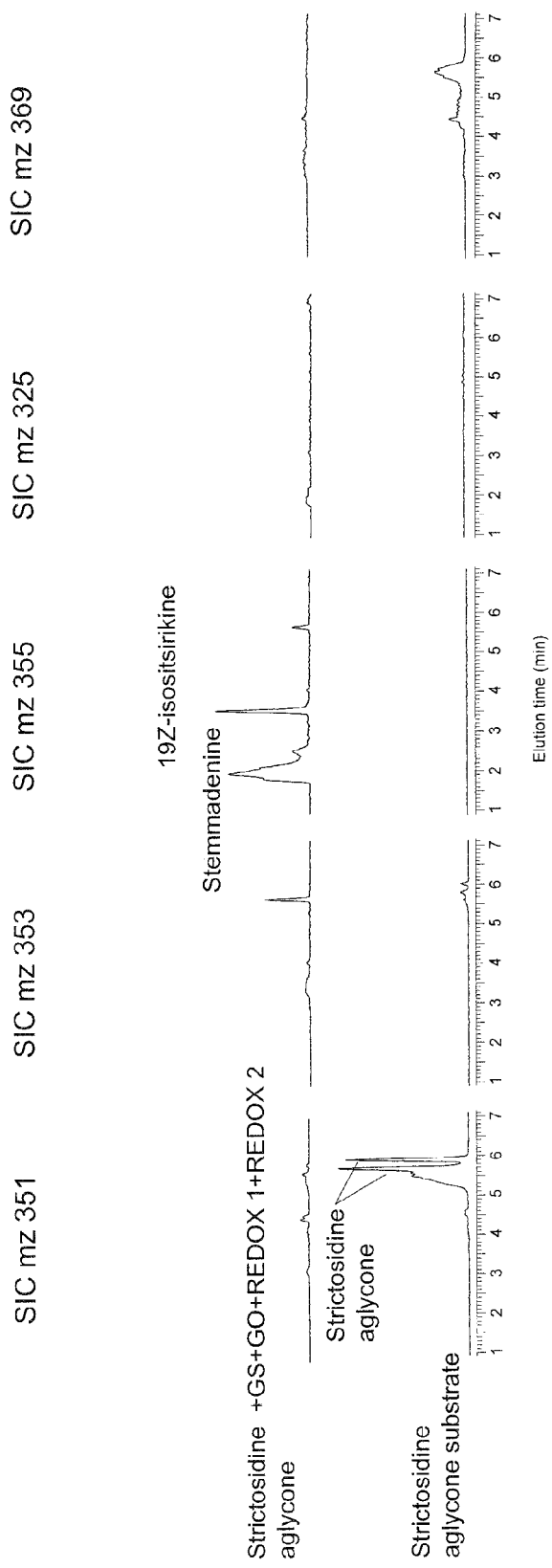
FIG. 10 depicts results obtained in certain experiments designed to evaluate the production of stemmadenine using a mixture of GS, GO, REDOX 1 and REDOX 2 as catalyzing enzymes. Shown is an LC-MS chromatogram showing the conversion of strictosidine aglycone to stemmadenine as selected ion chromatogram (SIC) SIC m/z 355.

This example illustrates the in vitro production of stemmadenine using GS, GO, REDOX 1 and REDOX 2 as a catalyzing enzymes. In vitro reactions (200 µl) containing 20 mM Tris pH 7.5, 1 mM NADPH, 5 µg strictosidine aglycone and 2.5 µg of each recombinantly produced purified GS (E. coli), REDOX 1 (E. coli), REDOX 2 (E. coli), and 200 µg yeast microsome containing GO were prepared. Reactions were set up to take place at 30° C. for 1 hr and the reaction products were dissolved in methanol and analyzed by LC-MS as selected ion chromatogram (SIC). As shown in FIG. 10, under the reaction conditions the GS, GO, REDOX 1 and REDOX 2 enzyme mixture catalyzes the production of stemmadenine.

Example 7—In Vivo Suppression of Geissoschizine Synthase (GS)

This example provides reduced transcript levels of GS in leaves of Catharanthus roseus using the tobacco rattle virus (TRV) vector system (virus induced gene silencing (VIGS). Following infiltration, virus induced gene silenced leaves were analyzed for the relative quantities of terpenoid indole alkaloids and chromatographic and spectral data were collected.

Figure 12:
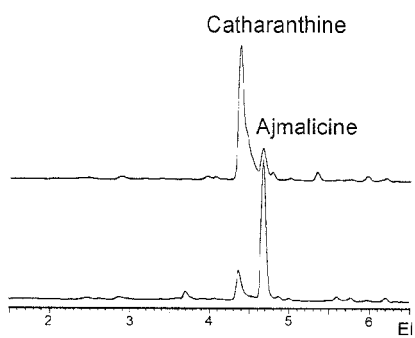
FIG. 12 depicts results obtained in certain experiments designed to evaluate silencing of the nucleic acid sequence encoding GS. Shown are an LC profile of leaf surface alkaloids of control plants (EV) and VIGS-GS plants at 280 nm (FIG. 12A); an LC profile of leaf body alkaloids of control plants (EV) and VIGS-GS plants at 300 nm (FIG. 12B); transcript levels of GS in control plants (EV) and VIGS-GS plants (FIG. 12C); alkaloid constituents of EV and VIGS-GS plants (FIG. 12D).
Figure 12:
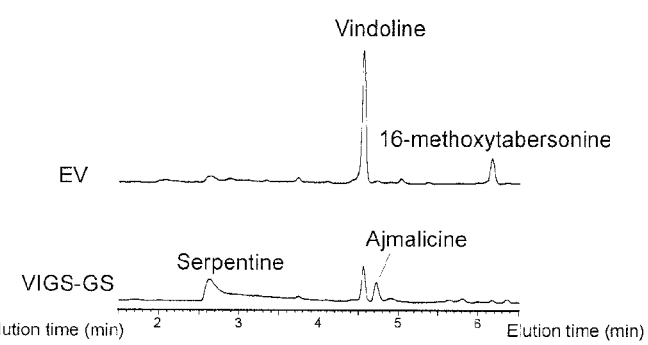
Figure 12:
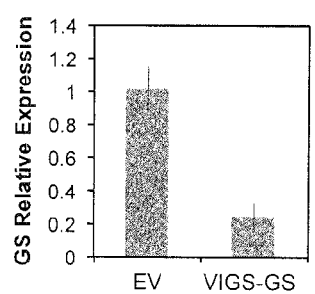
Figure 12:
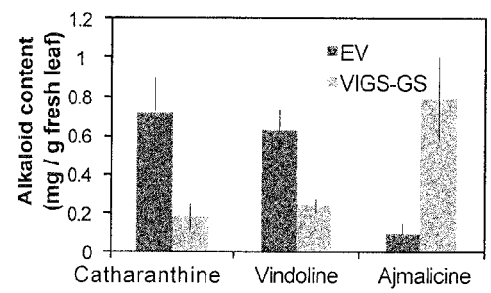

Shown in FIG. 12 are a representative LC profile of leaf surface alkaloid revealed at 280 nm showing the reduction of catharanthine and the increase of ajmalicine (FIG. 12A); a representative LC profile of leaf body alkaloid revealed at 300 nm showing the reduction of vindoline and 16-methoxytabersonine and the increase of serpentine (FIG. 12B); the relative transcripts level of GS in the leaves of the empty vector control plants (EV) and the VIGS-GS plants (FIG. 12C); the alkaloid contents in the EV plants and the VIGS-GS plants (FIG. 12D). The mean values were analyzed from 5 individual EV or VIGS plants, and the error bars indicate the standard deviation.

GS converts the strictosidine aglycone to geissoschizine with reduced nicotinamide adenine dinucleotide phosphate (NADPH) as the cofactor. Silencing GS in Catharanthus leaf by 76% caused a reduction of catharanthine and vindoline levels by 74% and 62%, respectively (Table 1). In contrast an earlier branch point leading to the formation of ajmalicine, also known to be derived from strictosidine aglycone was increased by 785% in GS-silenced plants (Table 1).

The results suggest that GS channels the common precursor, strictosidine, for the biosynthesis of catharanthine and tabersonine.

TABLE 1

GS trancripts and MIA accumulation in VIGS-GS plants comparing to VIGS-EV plants (Biological replicates n = 5).

|  |  | Transcripts | Catharanthine (mg/g fresh leaf) | Vindoline (mg/g fresh leaf) | Ajmalicine (mg/g fresh leaf) |
| --- | --- | --- | --- | --- | --- |
| VIGS-EV | Mean | 1.000 | 0.714 | 0.631 | 0.101 |
|  | SD | 0.141 | 0.178 | 0.096 | 0.052 |
| VIGS-GS | Mean | 0.241 | 0.184 | 0.240 | 0.793 |
|  | SD | 0.077 | 0.071 | 0.041 | 0.218 |

Example 8—In Vivo Suppression of Geissoschizine Oxidase (GO)

This example provides reduced transcript levels of GO in leaves of *Catharanthus roseus* using the tobacco rattle virus (TRV) vector system (virus induced gene silencing (VIGS). Following infiltration, virus induced gene silenced leaves were analyzed for the relative quantities of terpenoid indole alkaloids and chromatographic and spectral data were collected.

Shown in FIG. 13 are a representative LC profile of leaf surface alkaloid revealed at 280 nm showing the reduction of catharanthine and the increase of geissoschizine, pericyclivine, and perivine (FIG. 13A); a representative LC profile of leaf body alkaloid revealed at 300 nm showing the reduction of vindoline and 16-methoxytabersonine and the increase of perivine (FIG. 13B); the relative transcript levels of GO in the leaves of the empty vector control plants (EV) and the VIGS-GO plants (FIG. 13C); The alkaloid contents in the EV plants and the VIGS-GO plants (FIG. 13D). The mean values were analyzed from 5 individual EV or VIGS plants, and the error bars indicate the standard deviation.

GO oxidizes geissoschizine, the product of GS, to an unstable intermediate (m/z 369, addition of an oxygen atom to geissoschizine m/z 353) that gradually decomposes to the MIA akuammicine, with the co-enzyme cytochrome P450 reductase (CPR) and NADPH cofactor. Silencing GO in *Catharanthus* leaves by 92% reduced catharanthine and vindoline levels by 88% and 77%, respectively. In addition, geissoschizine that is not detected in wild type plant accumulated in GO-silenced plants, together with a few other MIAs (e.g. perivine, pericyclivine; FIG. 13, FIG. 17, Table 2). This suggests that back up of geissoschizine is channeled towards the formation of perivine and pericyclivine.

TABLE 2

GO trancripts and MIA accumulation in VIGS-GO plants comparing to VIGS-EV plants (Biological replicates n = 5).

|  |  | Transcripts | Catharanthine (mg/g fresh leaf) | Vindoline (mg/g fresh leaf) | Ajmalicine (mg/g fresh leaf) | Geissoschizine (mg/g fresh leaf) | Pericyclivine (mg/g fresh leaf) | Perivine (mg/g fresh leaf) |
| --- | --- | --- | --- | --- | --- | --- | --- | --- |
| VIGS-EV | Mean | 1.000 | 0.714 | 0.631 | 0.101 | 0.000 | 0.000 | 0.038 |
|  | SD | 0.141 | 0.178 | 0.096 | 0.052 | 0.000 | 0.000 | 0.018 |
| VIGS-GO | Mean | 0.078 | 0.084 | 0.145 | 0.094 | 0.649 | 0.451 | 0.340 |
|  | SD | 0.038 | 0.048 | 0.059 | 0.044 | 0.259 | 0.182 | 0.148 |

Example 9—In Vivo Suppression of Reductase 1 and Reductase 2 (REDOX 1 and REDOX 2)

This example provides reduced transcript levels of REDOX 1 and REDOX 2 in leaves of *Catharanthus roseus* using the tobacco rattle virus (TRV) vector system (virus induced gene silencing (VIGS)). Following infiltration, virus induced gene silenced leaves were analyzed for the relative quantities of terpenoid indole alkaloids and chromatographic and spectral data were collected.

Figure 14:
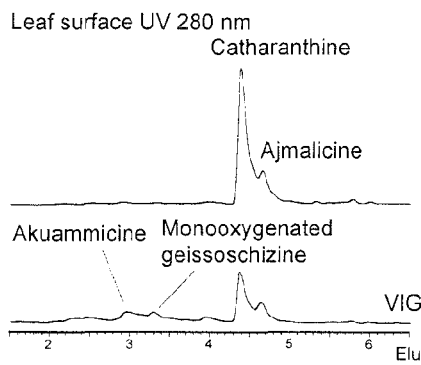
FIG. 14 depicts results obtained in certain experiments designed to evaluate silencing of the nucleic acid sequence encoding REDOX 1. Shown are an LC profile of leaf surface alkaloids of control plants (EV) and VIGS-REDOX 1 plants at 280 nm.
Figure 14:
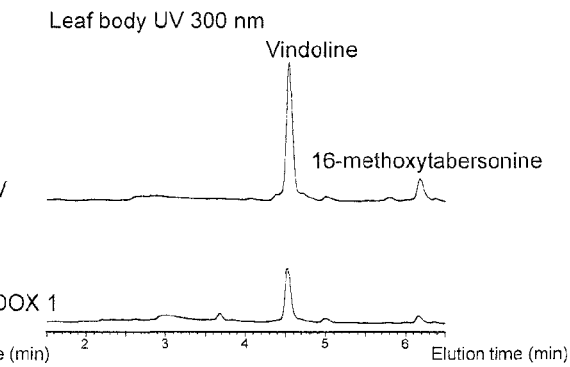
Figure 14:
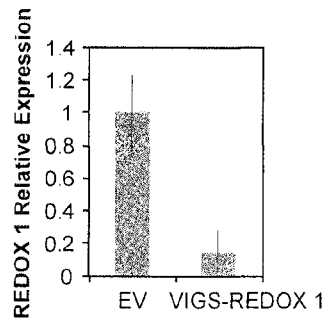
Figure 14:
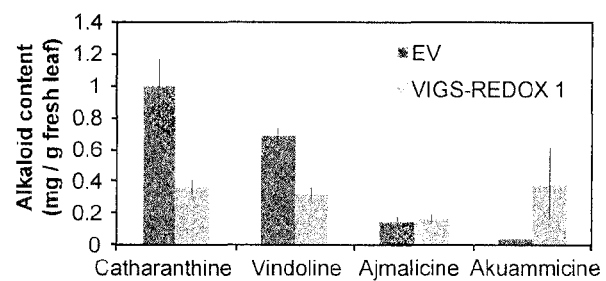
Figure 14:
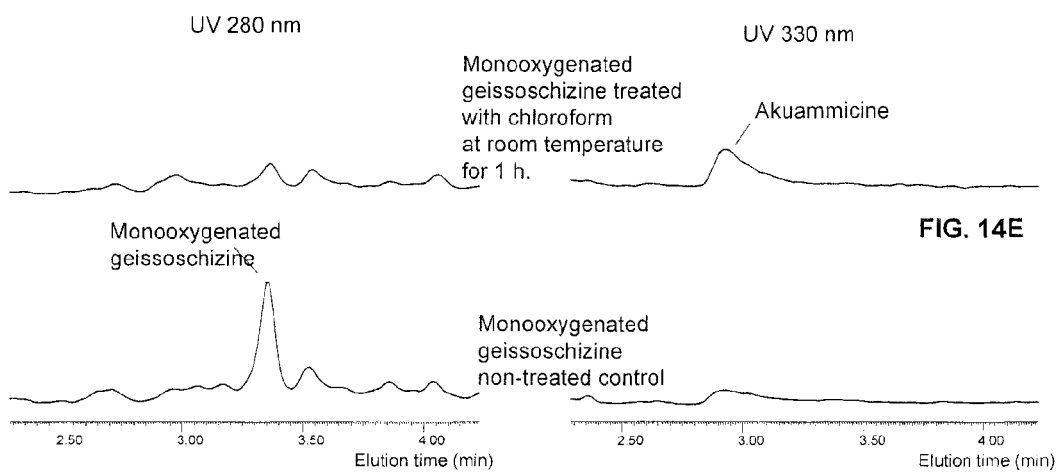

Shown in FIG. 14 are results obtained when silencing REDOX 1. Shown is a representative LC profile of leaf surface alkaloid revealed at 280 nm showing the reduction of catharanthine and the increase of unstable intermediate oxidized geissoschizine (m/z 369) and its decomposed byproduct akuammicine (FIG. 14A); a representative LC profile of leaf body alkaloid revealed at 300 nm showing the reduction of vindoline and 16-methoxytabersonine (FIG. 14B); The relative transcripts level of REDOX 1 in the leaves of the empty vector control plants (EV) and the VIGS-REDOX 1 plants (FIG. 14C); The alkaloid contents in the EV plants and the VIGS-REDOX 1 plants (FIG. 14D). The mean values were analyzed from 4 individual EV or VIGS plants, and the error bars indicate the standard deviation.

Figure 15:
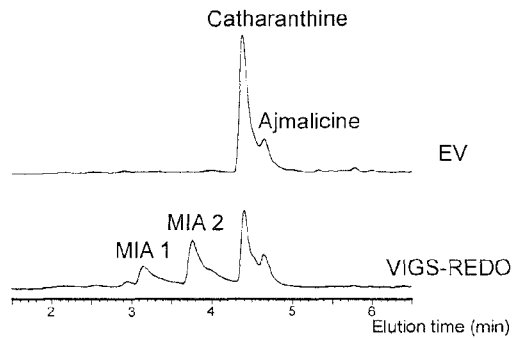
FIG. 15 depicts results obtained in certain experiments designed to evaluate silencing of the nucleic acid sequence encoding REDOX 2. Shown is an LC profile of leaf surface alkaloids of control plants (EV) and VIGS-REDOX 2 plants at 280 nm (FIG. 15A); an LC profile of leaf body alkaloids of control plants (EV) and VIGS-REDOX 2 plants at 300 nm (FIG. 15B); transcripts level of REDOX 2 in the leaves of the empty vector control plants (EV) and the VIGS-REDOX 2 plants (FIG. 15C); alkaloid contents in the EV plants and the VIGS-REDOX 2 plants (FIG. 15D).
Figure 15:
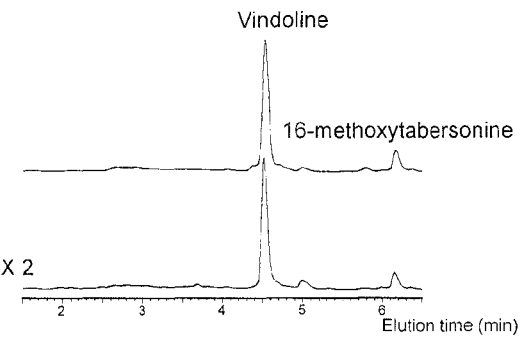
Figure 15:
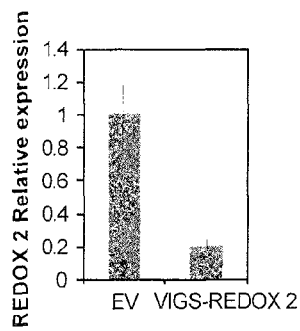
Figure 15:
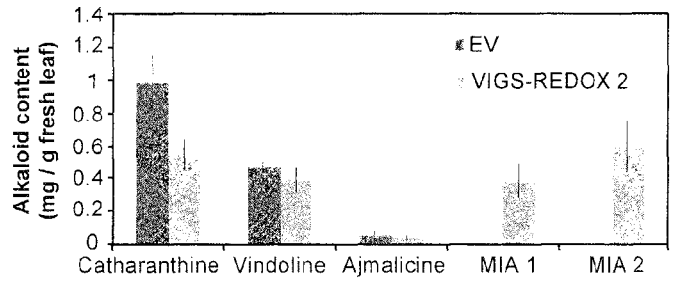

Shown in FIG. 15 are results obtained when silencing REDOX 2. Shown is a representative LC profile of leaf surface alkaloid revealed at 280 nm showing the reduction of catharanthine and the increase of isomeric MIA 1 and 2 (m/z 325) (FIG. 15A); a representative LC profile of leaf body alkaloid revealed at 300 nm showing the slight reduction of vindoline and 16-methoxytabersonine (FIG. 15B); relative transcripts level of REDOX 2 in the leaves of the empty vector control plants (EV) and the VIGS-REDOX 2 plants (FIG. 15C); alkaloid contents in the EV plants and the VIGS-REDOX 2 plants (FIG. 15D). The mean values were analyzed from 4 individual EV or VIGS plants, and the error bars indicate the standard deviation.

The VIGS silencing of REDOX 1 in *Catharanthus* leaves by 85% reduced catharanthine and vindoline levels by 64% and 54%, respectively; while akuammicine normally found in low-abundance increased 14-fold in REDOX 1-silenced plants (FIG. 14, FIG. 17, Table 3) compared to empty vector controls.

The VIGS silencing of REDOX 2 in *Catharanthus* leaf by 79% reduced catharanthine by 44% while vindoline levels were only slightly reduced by 16%. However, MIA 1 and MIA 2, the products of GO and REDOX 1 that are not detected in the wild type plants, accumulated at to levels comparable to catharanthine and vindoline found in VIGS silenced plants (FIG. 15, FIG. 17, Table 4).

TABLE 3

Redox 1 trancripts and MIA accumulation in VIGS-Redox 1 plants comparing to VIGS-EV plants (Biological replicates n = 4).

|  |  | Transcripts | Catharanthine (mg/g fresh leaf) | Vindoline (mg/g fresh leaf) | Ajmalicine (mg/g fresh leaf) | Akuammicine (mg/g fresh leaf) |
|---|---|---|---|---|---|---|
| VIGS-EV | Mean | 1.000 | 1.000 | 0.692 | 0.137 | 0.028 |
|  | SD | 0.235 | 0.201 | 0.045 | 0.029 | 0.009 |
| VIGS-Redox 1 | Mean | 0.148 | 0.359 | 0.320 | 0.162 | 0.383 |
|  | SD | 0.129 | 0.045 | 0.042 | 0.028 | 0.222 |

TABLE 4

Redox 2 trancripts and MIA accumulation in VIGS-Redox 2 plants comparing to VIGS-EV plants (Biological replicates n = 4)

|  |  | Transcripts | Catharanthine (mg/g fresh leaf) | Vindoline (mg/g fresh leaf) | Ajmalicine (mg/g fresh leaf) | MIA 1 (mg/g fresh leaf) | MIA 2 (mg/g fresh leaf) |
|---|---|---|---|---|---|---|---|
| VIGS-EV | Mean | 1.000 | 0.981 | 0.463 | 0.052 | 0.000 | 0.000 |
|  | SD | 0.235 | 0.173 | 0.033 | 0.031 | 0.000 | 0.000 |
| VIGS-Redox 2 | Mean | 0.206 | 0.547 | 0.390 | 0.036 | 0.378 | 0.590 |
|  | SD | 0.055 | 0.095 | 0.078 | 0.022 | 0.099 | 0.157 |

Example 10—In Vivo Suppression of Hydrolase 1 and Hydrolase 2 (HL1 and HL2)

This example provides reduced transcript levels of HL1 and HL2 in leaves of *Catharanthus roseus* using the tobacco rattle virus (TRV) vector system (virus induced gene silencing (VIGS). Following infiltration, virus induced gene silenced leaves were analyzed for the relative quantities of terpenoid indole alkaloids and chromatographic and spectral data were collected.

Shown in FIG. 16 are results obtained when silencing hydrolases 1 and 2 (HL1 and 2) in leaves of *Catharanthus* by VIGS. Shown are a representative LC profile of leaf total alkaloid revealed at 280 nm in empty vector control plants or when silenced by individual HLs (HL1 or HL2) (FIG. 16A); Shown are the relative HL1 and/or HL2 transcript levels in empty vector control plants or when silenced by individual HLs (HL1, HL2) (FIG. 16B); Shown are the alkaloid contents in the EV plants or when silenced by individual HLs (HL1, HL2) (FIG. 16C). The mean values were analyzed from 4 individual EV or VIGS plants, and the error bars indicate the standard deviation.

In *Catharanthus* leaves, two homologs hydrolases (HL1; HL2) of 78% identity at amino acids level are found. The expression levels of HL1 and HL2 are comparable (FIG. 16B).

Silencing HL1 in *Catharanthus* leaves by 93% reduced catharanthine levels by 80%6 with an increase of 164% for vindoline (FIG. 16, Table 5).

Silencing HL2 in *Catharanthus* leaves by 92% reduced vindoline by 66% with an increase of 210% for catharanthine (FIG. 16, Table 5).

TABLE 5

HL trancripts and MIA accumulation in VIGS-HL1-2 plants comparing to VIGS-EV plants (Biological replicates n = 4).

|  |  | Transcripts | Catharanthine (mg/g fresh leaf) | Vindoline (mg/g fresh leaf) |
|---|---|---|---|---|
| VIGS-EV | Mean-HL1 | 0.580 | 0.567 | 0.325 |
|  | SD | 0.133 | 0.119 | 0.041 |
|  | Mean-HL2 | 0.350 |  |  |
|  | SD | 0.055 |  |  |
| VIGS-HL1 | Mean-HL1 | 0.044 | 0.113 | 0.534 |
|  | SD | 0.025 | 0.036 | 0.149 |
|  | Mean-HL2 | 0.185 |  |  |
|  | SD | 0.038 |  |  |
| VIGS-HL2 | Mean-HL1 | 0.376 | 1.190 | 0.112 |
|  | SD | 0.139 | 0.348 | 0.051 |
|  | Mean-HL2 | 0.028 |  |  |
|  | SD | 0.018 |  |  |

Example 11—In Vitro Production of O-Acetylstemmadenine

Figure 11:
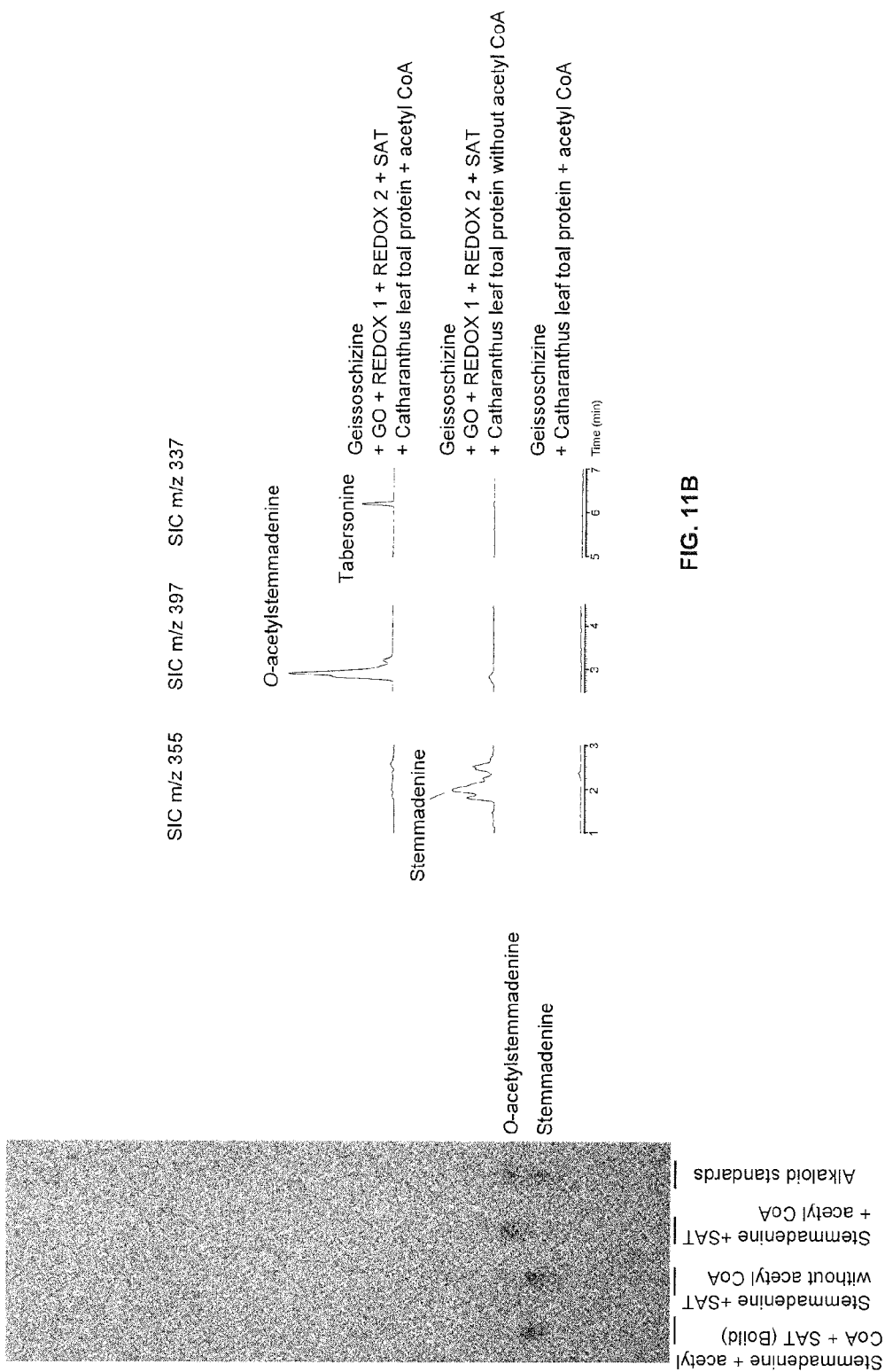
FIG. 11 depicts results obtained in certain experiments designed to evaluate the production of O-acetylstemmadenine and tabersonine using GO, REDOX 1, REDOX 2 and SAT as catalyzing enzymes. Shown is a TLC plate showing the conversion of stemmadenine to O-acetylstemmadenine (FIG. 11A), and an LC-MS chromatogram showing the conversion of geissoschizine to tabersonine and O-acetylstemmadenine with the presence of acetyl coenzyme A (acetyl CoA) and *Catharanthus* leaf total proteins as selected ion chromatogram (SIC) SIC m/z 337 and m/z 397, respectively (FIG. 11B).

This example illustrates the in vitro production of O-acetylstemmadenine using SAT as a catalyzing enzyme. In vitro reactions (200 µl) containing 20 mM Tris pH 7.5, 0.1 mM acetyl coenzyme A, 2 µg stemmadenine, and 1 µg of recombinantly produced and puridied SAT (*E. coli*) were prepared. Reactions were set up to take place at 30° C. for 1 hr and the reaction products were dissolved in acetone and analyzed by thin layer chromatography (TLC). As shown in FIG. 11A, under the reaction conditions the SAT enzyme catalyzes the production of O-acetylstemmadenine.

Example 12—In Vitro Production of Tabersonine

This example illustrates the in vitro production of tabersonine using GO, REDOX 1, REDOX 2, SAT and *Catharanthus* leaf total protein as a catalyzing enzymes. In vitro reactions (200 µl) containing 20 mM Tris pH 7.5, 1 mM NADPH, 0.1 mM acetyl coenzyme A, 2 μg geissoschizine, 2.5 μg of each recombinantly produced purified REDOX 1 (*E. coli*), REDOX 2 (*E. coli*), SAT (*E. coli*), 200 μg yeast microsome containing GO, and 100 μg *Catharanthus* leaf total protein (desalted) were prepared. Reactions were set up to take place at 30° C. for 1 hr and the reaction products were dissolved in methanol and analyzed by LC-MS as selected ion chromatogram (SIC). As shown in FIG. 11B, under the reaction conditions the enzyme mixture comprising GO, REDOX1, REDOX 2, SAT, and *Catharanthus* leaf total protein that contains HL2 catalyzes the production of tabersonine.

TABLE A

| | | | | | Tabersonine | | | |
|---|---|---|---|---|---|---|---|---|
| | | SGD | GS | GO | REDOX1 | REDOX2 | SAT | HL2 |
| Strictosidine | 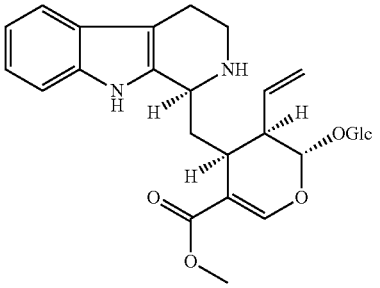 | ✓ | ✓ | ✓ | ✓ | ✓ | ✓ | ✓ |
| Strictosidine aglycone | 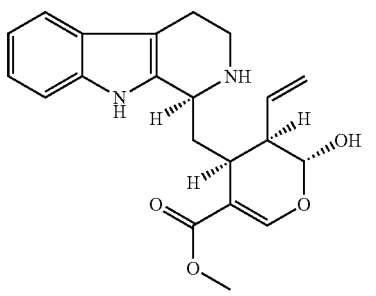 | | ✓ | ✓ | ✓ | ✓ | ✓ | ✓ |
| 4,21-dehydrogeissoschizine | 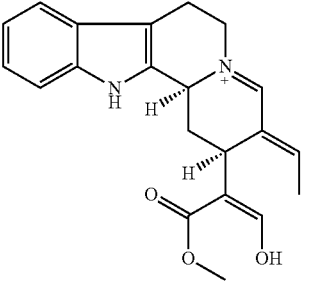 | | ✓ | ✓ | ✓ | ✓ | ✓ | ✓ |
| Geissoschizine | 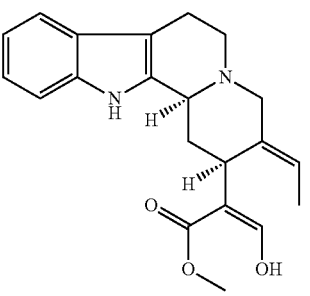 | | | ✓ | ✓ | ✓ | ✓ | ✓ |
| Monooxygenated geissoschizine | | | | | ✓ | ✓ | ✓ | ✓ |

TABLE B
| | Catharanthine | | | | | | |
|---|---|---|---|---|---|---|---|
| | SGD | GS | GO | REDOX1 | REDOX2 | SAT | HL1 |
| 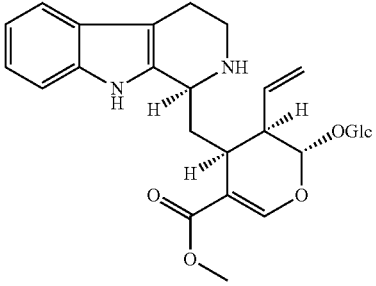Strictosidine | ✓ | ✓ | ✓ | ✓ | ✓ | ✓ | ✓ |
| 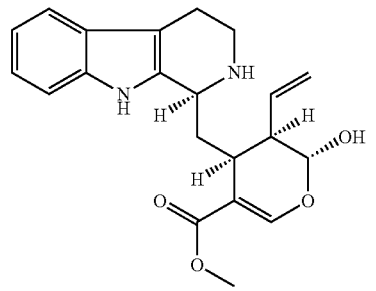Strictosidine aglycone | | ✓ | ✓ | ✓ | ✓ | ✓ | ✓ |
| 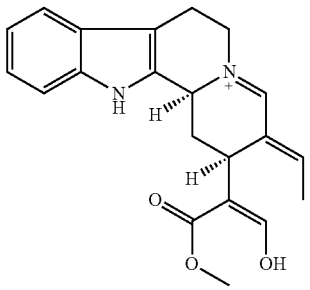4,21-dehydrogeissoschizine | | ✓ | ✓ | ✓ | ✓ | ✓ | ✓ |
| 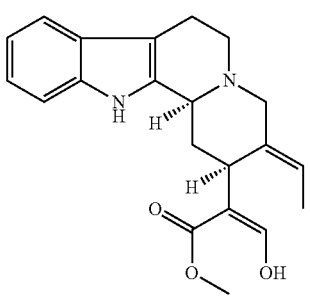Geissoschizine | | | ✓ | ✓ | ✓ | ✓ | ✓ |
| Monooxygenated geissoschizine | | | | ✓ | ✓ | ✓ | ✓ |

TABLE C
| | O-acetylstemmadenine | | | | | |
|---|---|---|---|---|---|---|
| | SGD | GS | GO | REDOX1 | REDOX2 | SAT |
| 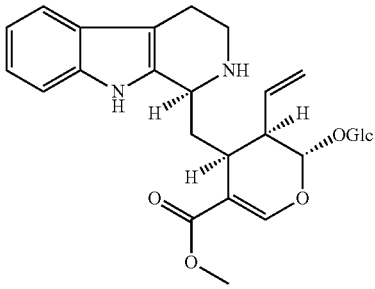 Strictosidine | ✓ | ✓ | ✓ | ✓ | ✓ | ✓ |
| 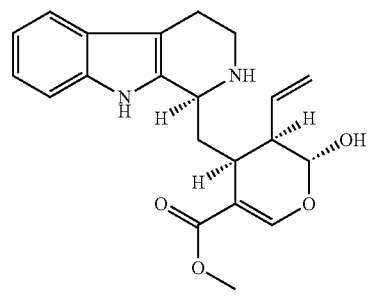 Strictosidine aglycone | | ✓ | ✓ | ✓ | ✓ | ✓ |
| 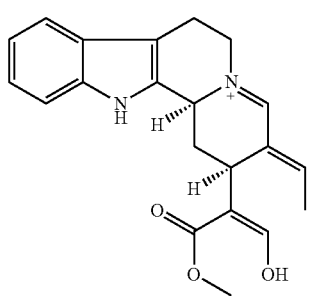 4,21-dehydrogeissoschizine | | ✓ | ✓ | ✓ | ✓ | ✓ |
| 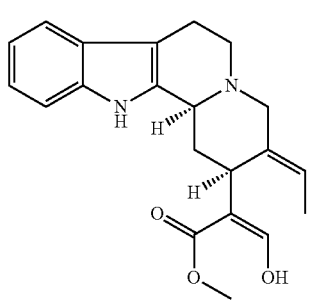 Geissoschizine | | | ✓ | ✓ | ✓ | ✓ |
| Monooxygenated geissoschizine | | | | ✓ | ✓ | ✓ |

TABLE C-continued
| O-acetylstemmadenine | | | | | | |
|---|---|---|---|---|---|---|
| | SGD | GS | GO | REDOX1 | REDOX2 | SAT |
| | | | | | | ✓ |
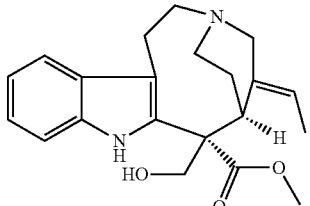
Stemmadenine
TABLE D
| Stemmadenine | | | | | |
|---|---|---|---|---|---|
| | SGD | GS | GO | REDOX1 | REDOX2 |
| Strictosidine | ✓ | ✓ | ✓ | ✓ | ✓ |
| Strictosidine aglycone | | ✓ | ✓ | ✓ | ✓ |
| 4,21-dehydrogeissoschizine | | ✓ | ✓ | ✓ | ✓ |

TABLE D-continued

Stemmadenine

| | SGD | GS | GO | REDOX1 | REDOX2 |
|---|---|---|---|---|---|

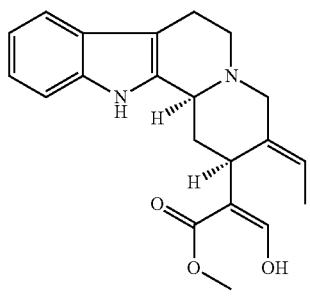

Geissoschizine: ✓ (GO), ✓ (REDOX1), ✓ (REDOX2)

Monooxygenated geissoschizine: ✓ (REDOX1), ✓ (REDOX2)

TABLE E

Monooxygenated geissoschizine

| | SGD | GS | GO |
|---|---|---|---|

Strictosidine: ✓ ✓ ✓

Strictosidine aglycone: ✓ ✓

4,21-dehydrogeissoschizine: ✓ ✓

TABLE E-continued

Monooxygenated geissoschizine

| | SGD | GS | GO |
|---|---|---|---|

Geissoschizine: ✓ (GO)

TABLE F

Geissoschizine

| | SGD | GS |
|---|---|---|

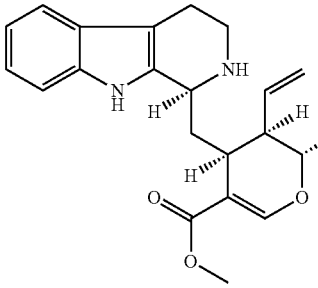

Strictosidine: ✓ ✓

TABLE F-continued

Geissoschizine

| | SGD | GS |
|---|---|---|
| 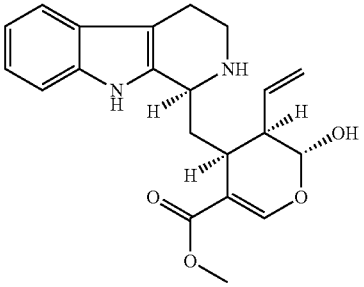 Strictosidine aglycone | | ✓ |
| 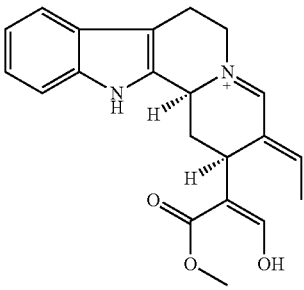 4,21-dehydrogeissoschizine | | ✓ |

TABLE G 4,21-dehydrogeissoschizine

| | SGD |
|---|---|
| 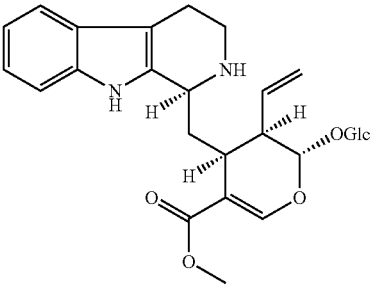 Strictosidine | ✓ |

Summary of Sequences

SEQ ID NO: 1 and SEQ ID NO: 8 set forth deduced amino acid sequences and nucleotide sequences, respectively, of certain strictosidine β-glucosidases (SGD).

(SEQ ID NO: 2; SEQ ID NO: 37; SEQ ID NO: 38 and SEQ ID NO: 39) and (SEQ ID NO: 9; SEQ ID NO: 17; SEQ ID NO: 18 and SEQ ID NO: 19) set forth deduced amino acid sequences and nucleotide sequences, respectively, of certain geissoschizine synthases (GS).

(SEQ ID NO: 3; SEQ ID NO: 40; SEQ ID NO: 41; and SEQ ID NO: 42) and (SEQ ID NO: 10; SEQ ID NO: 20; SEQ ID NO: 21; and SEQ ID NO: 22) set forth deduced amino acid sequences and nucleotide sequences, respectively, of certain geissoschizine oxidases (GO).

(SEQ ID NO: 4; SEQ ID NO: 43; SEQ. ID NO: 44 and SEQ ID NO: 45) and (SEQ ID NO: 11; SEQ ID NO: 23; SEQ ID NO: 24; and SEQ. ID NO: 25) set forth deduced amino acid sequences and nucleotide sequences, respectively, of certain reductases 1 (REDOX 1).

(SEQ ID NO: 5; SEQ ID NO: 46; SEQ ID NO: 47; and SEQ. ID NO: 48) and (SEQ ID NO: 12; SEQ ID NO: 26; SEQ ID NO: 27; and SEQ. ID NO: 28) set forth deduced amino acid sequences and nucleotide sequences, respectively, of certain reductases 2 (REDOX 2).

(SEQ ID NO: 6) and (SEQ ID NO: 13) set forth deduced amino acid sequences and nucleotide sequences, respectively, of certain hydrolases 1 (HL1).

(SEQ ID NO: 7; SEQ ID NO: 52; SEQ ID NO: 53; SEQ ID NO: 54; SEQ ID NO: 55 and SEQ ID 56) and (SEQ ID NO: 14; SEQ ID NO: 32; SEQ ID NO: 33; SEQ ID NO: 34; SEQ ID NO: 35 and SEQ ID NO: 36) set forth deduced amino acid sequences and nucleotide sequences, respectively, of certain hydrolases 2 (HL2).

(SEQ ID NO: 16; SEQ ID NO: 49; SEQ ID NO: 50; and SEQ ID NO: 51) and (SEQ ID NO: 15; SEQ ID NO: 29; SEQ ID NO: 30; and SEQ ID NO: 31) set forth the deduced amino acid sequences and nucleotide sequences, respectively of certain stemmadeninine acetyl transferases (SAT).

The invention claimed is:

1. A method of making tabersonine, comprising:
   (a) providing a terpenoid indole alkaloid compound; and
   (b) contacting the terpenoid indole alkaloid compound with catalytic quantities of a set of enzymes selected from
      (A) reductase 1 (REDOX 1), reductase 2 (REDOX 2), stemmadenine acetyltransferase (SAT), and hydrolase 2 (HL2);
      (B) geissoschizine oxidase (GO), reductase 1 (REDOX 1), reductase 2 (REDOX 2), stemmadenine acetyltransferase (SAT), and hydrolase 2 (HL2);
      (C) geissoschizine synthase (GS), geissoschizine oxidase (GO), reductase 1 (REDOX 1), reductase 2 (REDOX 2), stemmadenine acetyltransferase (SAT), and hydrolase 2 (HL2);or
      (D) strictosidine β-glucosidase (SGD), geissoschizine synthase (GS), geissoschizine oxidase (GO), reductase 1 (REDOX 1), reductase 2 (REDOX 2), stemmadenine acetyltransferase (SAT), and hydrolase 2 (HL2);
   wherein,
      (i) strictosidine β-glucosidase (SGD) comprises SEQ ID NO: 1 or a polypeptide having a sequence that is at least 85% identical thereto;
      (ii) geissoschizine synthase (GS) comprises SEQ ID NO: 2, 37, 38, or 39, or a polypeptide having a sequence that is at least 85% identical thereto;
      (iii) geissoschizine oxidase (GO) comprises SEQ ID NO: 3, 40, 41, or 42, or a polypeptide having a sequence that is at least 85% identical thereto;
      (iv) reductase 1 (REDOX 1) comprises SEQ ID NO: 4, 43, 44, or 45, or a polypeptide having a sequence that is at least 85% identical thereto;
      (v) reductase 2 (REDOX 2) comprises SEQ ID NO: 5, 46, 47, or 48, or a polypeptide having a sequence that is at least 85% identical thereto;
      (vi) stemmadenine acetyltransferase (SAT) comprises SEQ ID NO: 16, 49, 50 or 51, or a polypeptide having a sequence that is at least 85% identical thereto; and
      (vii) hydrolyase 2 (HL2) comprises SEQ ID NO: 7, 52, 53, 54, 55, or 56, or a polypeptide having a sequence that is at least 85% identical thereto;
   under reaction conditions permitting the catalysis of the terpenoid indole alkaloid compound to form tabersonine.

2. The method according to claim 1 wherein the terpenoid indole alkaloid is a tabersonine-catharanthine pathway precursor compound or a tabersonine-catharanthine pathway precursor derivative compound.

3. The method according to claim 1 wherein the terpenoid indole alkaloid compound is selected from the group consisting of strictosidine; 4,21-dehydrogeissoschizine; geissoschizine; monooxygenated geissoschizine; strictosidine aglycone; and a strictosidine aglycone derivative.

4. The method of making tabersonine according to claim 1, wherein the terpenoid indole alkaloid compound is strictosidine, and the enzymes are (i) SGD; (ii) GS; (iii) GO; (iv) REDOX 1; (v) REDOX 2; (vi) SAT; and (vii) HL2.

5. The method of making tabersonine according to claim 1, wherein the terpenoid indole alkaloid compound is strictosidine aglycone or a strictosidine aglycone derivative and the enzymes are (i) GS; (ii) GO; (iii) REDOX 1; (iv) REDOX 2; (v) SAT; and (vi) HL2.

6. The method of making tabersonine according to claim 1, wherein the terpenoid indole alkaloid compound is 4,21-dehydrogeissoschizine, and the enzymes are (i) GS; (ii) GO; (iii) REDOX 1; (iv) REDOX 2; (v) SAT; and (vi) HL2.

7. The method of making tabersonine according to claim 1, wherein the terpenoid indole alkaloid compound is geissoschizine, and the enzymes are (i) GO; (ii) REDOX 1; (iii) REDOX 2; (iv) SAT; and (v) HL2.

8. The method of making tabersonine according to claim 1, wherein the terpenoid indole alkaloid compound is monooxygenated geissoschizine, and the enzymes are (i) REDOX 1; (ii) REDOX 2; (iii) SAT; and (iv) HL2.

9. The method according to claim 1 wherein the reaction conditions are in vitro reaction conditions.

10. The method according to claim 1 wherein the reaction conditions are in vivo reaction conditions.

11. A method for preparing tabersonine, wherein the method comprises:
(a) providing a chimeric nucleic acid sequence comprising as operably linked components:
(i) one or more nucleic acid sequences encoding a set of polypeptides selected from
(A) reductase 1 (REDOX 1), reductase 2 (REDOX 2), stemmadenine acetyltransferase (SAT), and hydrolase 2 (HL2);
(B) geissoschizine oxidase (GO), reductase 1 (REDOX 1), reductase 2 (REDOX 2), stemmadenine acetyltransferase (SAT), and hydrolase 2 (HL2);
(C) geissoschizine synthase (GS), geissoschizine oxidase (GO), reductase 1 (REDOX 1), reductase 2 (REDOX 2), stemmadenine acetyltransferase (SAT), and hydrolase 2 (HL2); or
(D) strictosidine β-glucosidase (SGD), geissoschizine synthase (GS), geissoschizine oxidase (GO), reductase 1 (REDOX 1), reductase 2 (REDOX 2), stemmadenine acetyltransferase (SAT), and hydrolase 2 (HL2);
wherein,
strictosidine β-glucosidase (SGD) comprises SEQ ID NO: 1 or a polypeptide having a sequence that is at least 85% identical thereto;
geissoschizine synthase (GS) comprises SEQ ID NO: 2, 37, 38, or 39, or a polypeptide having a sequence that is at least 85% identical thereto;
geissoschizine oxidase (GO) comprises SEQ ID NO: 3, 40, 41, or 42, or a polypeptide having a sequence that is at least 85% identical thereto;
reductase 1 (REDOX 1) comprises SEQ ID NO: 4, 43, 44, or 45, or a polypeptide having a sequence that is at least 85% identical thereto;
reductase 2 (REDOX 2) comprises SEQ ID NO: 5, 46, 47 or 48, or a polypeptide having a sequence that is at least 85% identical thereto;
stemmadenine acetyltransferase (SAT) comprises SEQ ID NO: 16, 49, 50 or 51, or a polypeptide having a sequence that is at least 85% identical thereto; and
hydrolyase 2 (HL2) comprises SEQ ID NO: 7, 52, 53, 54, 55, or 56, or a polypeptide having a sequence that is at least 85% identical thereto; and
(ii) one or more nucleic acid sequences capable of controlling expression in a host cell;
(b) introducing the chimeric nucleic acid sequence into a host cell and growing the host cell to produce the encoded polypeptides; and
(c) recovering tabersonine.

12. A method according to any one oaf claim 1, 9 or 10, wherein the enzymes are selected from the group consisting of (i) strictosidine β-glucosidase (SGD) comprising SEQ ID NO: 1 or a polypeptide having a sequence that is at least 85% identical thereto; (ii) geissoschizine synthase (GS) comprising SEQ ID NO: 2 or a polypeptide having a sequence that is at least 85% identical thereto; (iii) geissoschizine oxidase (GO) comprising SEQ ID NO: 3 or a polypeptide having a sequence that is at least 85% identical thereto; (iv) reductase 1 (REDOX 1) comprising SEQ ID NO: 4 or a polypeptide having a sequence that is at least 85% identical thereto; (v) reductase 2 (REDOX 2) comprising SEQ ID NO: 5 or a polypeptide having a sequence that is at least 85% identical thereto; (vi) stemmadenine acetyltransferase (SAT) comprising SEQ ID NO: 16 or a polypeptide having a sequence that is at least 85% identical thereto; and (vii) hydrolyase 2 (HL2) comprising SEQ ID NO: 7 or a polypeptide having a sequence that is at least 85% identical thereto.

13. A method according to claim 12, wherein the enzymes are selected from the group consisting of (i) strictosidine β-glucosidase (SGD) comprising SEQ ID NO: 1 or a polypeptide having a sequence that is at least 90% identical thereto; (ii) geissoschizine synthase (GS) comprising SEQ ID NO: 2 or a polypeptide having a sequence that is at least 90% identical thereto; (iii) geissoschizine oxidase (GO) comprising SEQ ID NO: 3 or a polypeptide having a sequence that is at least 90% identical thereto; (iv) reductase 1 (REDOX 1) comprising SEQ ID NO: 4 or a polypeptide having a sequence that is at least 85% identical thereto; (v) reductase 2 (REDOX 2) comprising SEQ ID NO: 5 or a polypeptide having a sequence that is at least 90% identical thereto; (vi) stemmadenine acetyltransferase (SAT) comprising SEQ ID NO: 16 or a polypeptide having a sequence that is at least 90% identical thereto; and (vii) hydrolyase 2 (HL2) comprising SEQ ID NO: 7 or a polypeptide having a sequence that is at least 90% identical thereto.

14. A method according to claim 13, wherein the enzymes are selected from the group consisting of (i) strictosidine β-glucosidase (SGD) comprising SEQ ID NO: 1 or a polypeptide having a sequence that is at least 95% identical thereto; (ii) geissoschizine synthase (GS) comprising SEQ ID NO: 2 or a polypeptide having a sequence that is at least 95% identical thereto; (iii) geissoschizine oxidase (GO) comprising SEQ ID NO: 3 or a polypeptide having a sequence that is at least 95% identical thereto; (iv) reductase 1 (REDOX 1) comprising SEQ ID NO: 4 or a polypeptide having a sequence that is at least 85% identical thereto; (v) reductase 2 (REDOX 2) comprising SEQ ID NO: 5 or a polypeptide having a sequence that is at least 95% identical thereto; (vi) stemmadenine acetyltransferase (SAT) comprising SEQ ID NO: 16 or a polypeptide having a sequence that is at least 95% identical thereto; and (vii) hydrolyase 2 (HL2) comprising SEQ ID NO: 7 or a polypeptide having a sequence that is at least 95% identical thereto.

15. A method according to claim 14, wherein the enzymes are selected from the group consisting of (i) strictosidine β-glucosidase (SGD) comprising SEQ ID NO: 1; (ii) geissoschizine synthase (GS) comprising SEQ ID NO: 2; (iii) geissoschizine oxidase (GO) comprising SEQ ID NO: 3; (iv) reductase 1 (REDOX 1) comprising SEQ ID NO: 4; (v) reductase 2 (REDOX 2) comprising SEQ ID NO: 5; (vi) stemmadenine acetyltransferase (SAT) comprising SEQ ID NO: 16; and (vii) hydrolyase 2 (HL2) comprising SEQ ID NO: 7.

\* \* \* \* \*

SEQUENCE LISTING

<160> NUMBER OF SEQ ID NOS: 56

<210> SEQ ID NO 1
<211> LENGTH: 555
<212> TYPE: PRT
<213> ORGANISM: Catharanthus roseus
<220> FEATURE:
<221> NAME/KEY: MISC_FEATURE
<223> OTHER INFORMATION: SGD (Strictosidine beta-glucosidase)

<400> SEQUENCE: 1

Met Gly Ser Lys Asp Asp Gln Ser Leu Val Val Ala Ile Ser Pro Ala
1               5                   10                  15

Ala Glu Pro Asn Gly Asn His Ser Val Pro Ile Pro Phe Ala Tyr Pro
            20                  25                  30

Ser Ile Pro Ile Gln Pro Arg Lys His Asn Lys Pro Ile Val His Arg
        35                  40                  45

Arg Asp Phe Pro Ser Asp Phe Ile Leu Gly Ala Gly Ser Ala Tyr
    50                  55                  60

Gln Cys Glu Gly Ala Tyr Asn Glu Gly Asn Arg Gly Pro Ser Ile Trp
65                  70                  75                  80

Asp Thr Phe Thr Asn Arg Tyr Pro Ala Lys Ile Ala Asp Gly Ser Asn
                85                  90                  95

Gly Asn Gln Ala Ile Asn Ser Tyr Asn Leu Tyr Lys Glu Asp Ile Lys
            100                 105                 110

Ile Met Lys Gln Thr Gly Leu Glu Ser Tyr Arg Phe Ser Ile Ser Trp
        115                 120                 125

Ser Arg Val Leu Pro Gly Gly Asn Leu Ser Gly Gly Val Asn Lys Asp
130                 135                 140

Gly Val Lys Phe Tyr His Asp Phe Ile Asp Glu Leu Leu Ala Asn Gly
145                 150                 155                 160

Ile Lys Pro Phe Ala Thr Leu Phe His Trp Asp Leu Pro Gln Ala Leu
                165                 170                 175

Glu Asp Glu Tyr Gly Gly Phe Leu Ser Asp Arg Ile Val Glu Asp Phe
            180                 185                 190

Thr Glu Tyr Ala Glu Phe Cys Phe Trp Glu Phe Gly Asp Lys Val Lys
        195                 200                 205

Phe Trp Thr Thr Phe Asn Glu Pro His Thr Tyr Val Ala Ser Gly Tyr
210                 215                 220

Ala Thr Gly Glu Phe Ala Pro Gly Arg Gly Gly Ala Asp Gly Lys Gly
225                 230                 235                 240

Asn Pro Gly Lys Glu Pro Tyr Ile Ala Thr His Asn Leu Leu Leu Ser
                245                 250                 255

His Lys Ala Ala Val Glu Val Tyr Arg Lys Asn Phe Gln Lys Cys Gln
            260                 265                 270

Gly Gly Glu Ile Gly Ile Val Leu Asn Ser Met Trp Met Glu Pro Leu
        275                 280                 285

Asn Glu Thr Lys Glu Asp Ile Asp Ala Arg Glu Arg Gly Pro Asp Phe
290                 295                 300

Met Leu Gly Trp Phe Ile Glu Pro Leu Thr Thr Gly Glu Tyr Pro Lys
305                 310                 315                 320

Ser Met Arg Ala Leu Val Gly Ser Arg Leu Pro Glu Phe Ser Thr Glu
                325                 330                 335

Asp Ser Glu Lys Leu Thr Gly Cys Tyr Asp Phe Ile Gly Met Asn Tyr
            340                 345                 350

Tyr Thr Thr Thr Tyr Val Ser Asn Ala Asp Lys Ile Pro Asp Thr Pro
        355                 360                 365

Gly Tyr Glu Thr Asp Ala Arg Ile Asn Lys Asn Ile Phe Val Lys Lys
            370                 375                 380

Val Asp Gly Lys Glu Val Arg Ile Gly Glu Pro Cys Tyr Gly Gly Trp
385                 390                 395                 400

Gln His Val Val Pro Ser Gly Leu Tyr Asn Leu Leu Val Tyr Thr Lys

```
                405                 410                 415
Glu Lys Tyr His Val Pro Val Ile Tyr Val Ser Glu Cys Gly Val Val
            420                 425                 430

Glu Glu Asn Arg Thr Asn Ile Leu Leu Thr Glu Gly Lys Thr Asn Ile
        435                 440                 445

Leu Leu Thr Glu Ala Arg His Asp Lys Leu Arg Val Asp Phe Leu Gln
    450                 455                 460

Ser His Leu Ala Ser Val Arg Asp Ala Ile Asp Asp Gly Val Asn Val
465                 470                 475                 480

Lys Gly Phe Phe Val Trp Ser Phe Asp Asn Phe Glu Trp Asn Leu
            485                 490                 495

Gly Tyr Ile Cys Arg Tyr Gly Ile Ile His Val Asp Tyr Lys Thr Phe
            500                 505                 510

Gln Arg Tyr Pro Lys Asp Ser Ala Ile Trp Tyr Lys Asn Phe Ile Ser
            515                 520                 525

Glu Gly Phe Val Thr Asn Thr Ala Lys Lys Arg Phe Arg Glu Glu Asp
            530                 535                 540

Lys Leu Val Glu Leu Val Lys Lys Gln Lys Tyr
545                 550                 555

<210> SEQ ID NO 2
<211> LENGTH: 364
<212> TYPE: PRT
<213> ORGANISM: Catharanthus roseus
<220> FEATURE:
<221> NAME/KEY: MISC_FEATURE
<223> OTHER INFORMATION: GS (Geissoschizine synthase)

<400> SEQUENCE: 2

Met Ala Gly Glu Thr Thr Lys Leu Asp Leu Ser Val Lys Ala Val Gly
1               5                   10                  15

Trp Gly Ala Ala Asp Ala Ser Gly Val Leu Gln Pro Ile Lys Phe Tyr
            20                  25                  30

Arg Arg Val Pro Gly Glu Arg Asp Val Lys Ile Arg Val Leu Tyr Ser
        35                  40                  45

Gly Val Cys Asn Phe Asp Met Glu Met Val Arg Asn Lys Trp Gly Phe
    50                  55                  60

Thr Arg Tyr Pro Tyr Val Phe Gly His Glu Thr Ala Gly Glu Val Val
65                  70                  75                  80

Glu Val Gly Ser Lys Val Glu Lys Phe Lys Val Gly Asp Lys Val Ala
            85                  90                  95

Val Gly Cys Met Val Gly Ser Cys Gln Cys Tyr Asn Cys Gln Ser
            100                 105                 110

Gly Met Glu Asn Tyr Cys Pro Glu Pro Asn Met Ala Asp Gly Ser Val
        115                 120                 125

Tyr Arg Glu Gln Gly Glu Arg Ser Tyr Gly Gly Cys Ser Asn Val Met
    130                 135                 140

Val Val Asp Glu Lys Phe Val Leu Arg Trp Pro Glu Asn Leu Pro Gln
145                 150                 155                 160

Asp Lys Gly Val Ala Leu Leu Cys Ala Gly Val Val Tyr Ser Pro
            165                 170                 175

Met Lys His Leu Gly Leu Asp Lys Pro Gly Lys His Ile Gly Val Phe
            180                 185                 190

Gly Leu Gly Gly Leu Gly Ser Val Ala Val Lys Phe Ile Lys Ala Phe
        195                 200                 205
```

Gly Gly Lys Ala Thr Val Ile Ser Thr Ser Arg Arg Lys Glu Lys Glu
            210                 215                 220

Ala Ile Glu Glu His Gly Ala Asp Ala Phe Val Val Asn Thr Asp Ser
225                 230                 235                 240

Glu Gln Leu Lys Ala Leu Ala Gly Thr Met Asp Gly Val Val Asp Thr
                245                 250                 255

Thr Pro Gly Gly Arg Thr Pro Met Ser Leu Met Leu Asn Leu Leu Lys
            260                 265                 270

Phe Asp Gly Ala Val Met Leu Val Gly Ala Pro Glu Ser Leu Phe Glu
275                 280                 285

Leu Pro Ala Ala Pro Leu Ile Met Gly Arg Lys Lys Ile Ile Gly Ser
            290                 295                 300

Ser Thr Gly Gly Leu Lys Glu Tyr Gln Glu Met Leu Asp Phe Ala Ala
305                 310                 315                 320

Lys His Asn Ile Val Cys Asp Thr Glu Val Ile Gly Ile Asp Tyr Leu
                325                 330                 335

Ser Thr Ala Met Glu Arg Ile Lys Asn Leu Asp Val Lys Tyr Arg Phe
            340                 345                 350

Ala Ile Asp Ile Gly Asn Thr Leu Lys Phe Glu Glu
                355                 360

<210> SEQ ID NO 3
<211> LENGTH: 501
<212> TYPE: PRT
<213> ORGANISM: Catharanthus roseus
<220> FEATURE:
<221> NAME/KEY: MISC_FEATURE
<223> OTHER INFORMATION: GO (Geissoschizine oxidase)

<400> SEQUENCE: 3

Met Glu Phe Ser Phe Ser Ser Pro Ala Leu Tyr Ile Val Tyr Phe Leu
1               5                   10                  15

Leu Phe Phe Val Val Arg Gln Leu Leu Lys Pro Lys Ser Lys Lys Lys
                20                  25                  30

Leu Pro Pro Gly Pro Arg Thr Leu Pro Leu Ile Gly Asn Leu His Gln
            35                  40                  45

Leu Ser Gly Pro Leu Pro His Arg Thr Leu Lys Asn Leu Ser Asp Lys
50                  55                  60

His Gly Pro Leu Met His Val Lys Met Gly Glu Arg Ser Ala Ile Ile
65                  70                  75                  80

Val Ser Asp Ala Arg Met Ala Lys Ile Val Leu His Asn Asn Gly Leu
                85                  90                  95

Ala Val Ala Asp Arg Ser Val Asn Thr Val Ala Ser Ile Met Thr Tyr
            100                 105                 110

Asn Ser Leu Gly Val Thr Phe Ala Gln Tyr Gly Asp Tyr Leu Thr Lys
            115                 120                 125

Leu Arg Gln Ile Tyr Thr Leu Glu Leu Leu Ser Gln Lys Lys Val Arg
130                 135                 140

Ser Phe Tyr Ser Cys Phe Glu Asp Glu Leu Asp Thr Phe Val Lys Ser
145                 150                 155                 160

Ile Lys Ser Asn Val Gly Gln Pro Met Val Leu Tyr Glu Lys Ala Ser
                165                 170                 175

Ala Tyr Leu Tyr Ala Thr Ile Cys Arg Thr Ile Phe Gly Ser Val Cys
            180                 185                 190

Lys Glu Lys Glu Lys Met Ile Lys Ile Val Lys Lys Thr Ser Leu Leu
            195                 200                 205

-continued

```
Ser Gly Thr Pro Leu Arg Leu Glu Asp Leu Phe Pro Ser Met Ser Ile
    210                 215                 220

Phe Cys Arg Phe Ser Lys Thr Leu Asn Gln Leu Arg Gly Leu Leu Gln
225                 230                 235                 240

Glu Met Asp Asp Ile Leu Glu Glu Ile Ile Val Glu Arg Glu Lys Ala
                245                 250                 255

Ser Glu Val Ser Lys Glu Ala Lys Asp Glu Asp Met Leu Ser Val
                260                 265                 270

Leu Leu Arg His Lys Trp Tyr Asn Pro Ser Gly Ala Lys Phe Arg Ile
            275                 280                 285

Thr Asn Ala Asp Ile Lys Ala Ile Ile Phe Glu Leu Ile Leu Ala Ala
        290                 295                 300

Thr Leu Ser Val Ala Asp Val Thr Glu Trp Ala Met Val Glu Ile Leu
305                 310                 315                 320

Arg Asp Pro Lys Ser Leu Lys Lys Val Tyr Glu Glu Val Arg Gly Ile
                325                 330                 335

Cys Lys Glu Lys Lys Arg Val Thr Gly Tyr Asp Val Glu Lys Met Glu
                340                 345                 350

Phe Met Arg Leu Cys Val Lys Glu Ser Thr Arg Ile His Pro Ala Ala
            355                 360                 365

Pro Leu Leu Val Pro Arg Glu Cys Arg Glu Asp Phe Glu Val Asp Gly
        370                 375                 380

Tyr Thr Val Pro Lys Gly Ala Trp Val Ile Thr Asn Cys Trp Ala Val
385                 390                 395                 400

Gln Met Asp Pro Thr Val Trp Pro Glu Pro Lys Phe Asp Pro Glu
                405                 410                 415

Arg Tyr Ile Arg Asn Pro Met Asp Phe Tyr Gly Ser Asn Phe Glu Leu
            420                 425                 430

Ile Pro Phe Gly Thr Gly Arg Arg Gly Cys Pro Gly Ile Leu Tyr Gly
        435                 440                 445

Val Thr Asn Ala Glu Phe Met Leu Ala Ala Met Phe Tyr His Phe Asp
450                 455                 460

Trp Glu Ile Ala Asp Gly Lys Lys Pro Glu Glu Ile Asp Leu Thr Glu
465                 470                 475                 480

Asp Phe Gly Ala Gly Cys Ile Met Lys Tyr Pro Leu Lys Leu Val Pro
                485                 490                 495

His Leu Val Asn Asp
            500

<210> SEQ ID NO 4
<211> LENGTH: 354
<212> TYPE: PRT
<213> ORGANISM: Catharanthus roseus
<220> FEATURE:
<221> NAME/KEY: MISC_FEATURE
<223> OTHER INFORMATION: REDOX 1 (Reductase 1)

<400> SEQUENCE: 4

Met Ala Asp Arg Val Lys Thr Val Gly Trp Ala Ala His Asp Ser Ser
1               5                   10                  15

Gly Phe Leu Ser Pro Phe Gln Phe Thr Arg Arg Ala Thr Gly Glu Glu
                20                  25                  30

Asp Val Arg Leu Lys Val Leu Tyr Cys Gly Val Cys His Ser Asp Leu
            35                  40                  45

His Asn Ile Lys Asn Glu Met Gly Phe Thr Ser Tyr Pro Cys Val Pro
```

Gly His Glu Val Val Gly Glu Val Thr Glu Val Gly Asn Lys Val Lys
65                  70                  75                  80

Lys Phe Ile Ile Gly Asp Lys Val Gly Val Gly Leu Phe Val Asp Ser
                85                  90                  95

Cys Gly Glu Cys Glu Gln Cys Val Asn Asp Val Glu Thr Tyr Cys Pro
            100                 105                 110

Lys Leu Lys Met Ala Tyr Leu Ser Ile Asp Asp Gly Thr Val Ile
            115                 120                 125

Gln Gly Gly Tyr Ser Lys Glu Met Val Ile Lys Glu Arg Tyr Val Phe
        130                 135                 140

Arg Trp Pro Glu Asn Leu Pro Leu Pro Ala Gly Thr Pro Leu Leu Gly
145                 150                 155                 160

Ala Gly Ser Thr Val Tyr Ser Pro Met Lys Tyr Tyr Gly Leu Asp Lys
                165                 170                 175

Ser Gly Gln His Leu Gly Val Val Gly Leu Gly Gly Leu Gly His Leu
            180                 185                 190

Ala Val Lys Phe Ala Lys Ala Phe Gly Leu Lys Val Thr Val Ile Ser
        195                 200                 205

Thr Ser Pro Ser Lys Lys Asp Glu Ala Ile Asn His Leu Gly Ala Asp
    210                 215                 220

Ala Phe Leu Val Ser Thr Asp Gln Glu Gln Thr Gln Lys Ala Met Ser
225                 230                 235                 240

Thr Met Asp Gly Ile Ile Asp Thr Val Ser Ala Pro His Ala Leu Met
                245                 250                 255

Pro Leu Phe Ser Leu Leu Lys Pro Asn Gly Lys Leu Val Val Val Gly
            260                 265                 270

Ala Pro Asn Lys Pro Val Glu Leu Asp Ile Leu Phe Leu Val Met Gly
        275                 280                 285

Arg Lys Met Leu Gly Thr Ser Ser Val Gly Gly Val Lys Glu Thr Gln
    290                 295                 300

Glu Met Ile Asp Phe Ala Ala Lys His Gly Ile Val Ala Asp Val Glu
305                 310                 315                 320

Val Val Glu Met Glu Asn Val Asn Asn Ala Met Glu Arg Leu Ala Lys
                325                 330                 335

Gly Asp Val Arg Tyr Arg Phe Val Leu Asp Ile Gly Asn Ala Thr Val
            340                 345                 350

Ala Val

<210> SEQ ID NO 5
<211> LENGTH: 323
<212> TYPE: PRT
<213> ORGANISM: Catharanthus roseus
<220> FEATURE:
<221> NAME/KEY: MISC_FEATURE
<223> OTHER INFORMATION: REDOX 2 (Reductase 2)

<400> SEQUENCE: 5

Met Glu Lys Gln Val Glu Ile Pro Glu Val Glu Leu Asn Ser Gly His
1               5                   10                  15

Lys Met Pro Ile Val Gly Tyr Gly Thr Cys Val Pro Glu Pro Met Pro
                20                  25                  30

Pro Leu Glu Glu Leu Thr Ala Ile Phe Leu Asp Ala Ile Lys Val Gly
            35                  40                  45

Tyr Arg His Phe Asp Thr Ala Ser Ser Tyr Gly Thr Glu Glu Ala Leu

```
                    50                  55                  60
Gly Lys Ala Ile Ala Glu Ala Ile Asn Ser Gly Leu Val Lys Ser Arg
 65                  70                  75                  80

Glu Glu Phe Phe Ile Ser Cys Lys Leu Trp Ile Glu Asp Ala Asp His
                     85                  90                  95

Asp Leu Ile Leu Pro Ala Leu Asn Gln Ser Leu Gln Ile Leu Gly Val
                100                 105                 110

Asp Tyr Leu Asp Leu Tyr Met Ile His Met Pro Val Arg Val Arg Lys
                115                 120                 125

Gly Ala Pro Met Phe Asn Tyr Ser Lys Glu Asp Phe Leu Pro Phe Asp
            130                 135                 140

Ile Gln Gly Thr Trp Lys Ala Met Glu Glu Cys Ser Lys Gln Gly Leu
145                 150                 155                 160

Ala Lys Ser Ile Gly Val Ser Asn Tyr Ser Val Glu Lys Leu Thr Lys
                165                 170                 175

Leu Leu Glu Thr Ser Thr Ile Pro Pro Ala Val Asn Gln Val Glu Met
                180                 185                 190

Asn Val Ala Trp Gln Gln Arg Lys Leu Leu Pro Phe Cys Lys Glu Lys
            195                 200                 205

Asn Ile His Ile Thr Ser Trp Ser Pro Leu Leu Ser Tyr Gly Val Ala
        210                 215                 220

Trp Gly Ser Asn Ala Val Met Glu Asn Pro Val Leu Gln Gln Ile Ala
225                 230                 235                 240

Ala Ser Lys Gly Lys Thr Val Ala Gln Val Ala Leu Arg Trp Ile Tyr
                245                 250                 255

Glu Gln Gly Ala Ser Leu Ile Thr Arg Thr Ser Asn Lys Asp Arg Met
            260                 265                 270

Phe Glu Asn Val Gln Ile Phe Asp Trp Glu Leu Ser Lys Glu Glu Leu
        275                 280                 285

Asp Gln Ile His Glu Ile Pro Gln Arg Arg Gly Thr Leu Gly Glu Glu
    290                 295                 300

Phe Met His Pro Glu Gly Pro Ile Lys Ser Pro Glu Glu Leu Trp Asp
305                 310                 315                 320

Gly Asp Leu

<210> SEQ ID NO 6
<211> LENGTH: 330
<212> TYPE: PRT
<213> ORGANISM: Catharanthus roseus
<220> FEATURE:
<221> NAME/KEY: MISC_FEATURE
<223> OTHER INFORMATION: HL1 (Hydrolase 1)

<400> SEQUENCE: 6

Met Asn Ser Ser Thr Asp Pro Thr Ser Asp Glu Thr Ile Trp Asp Leu
 1               5                  10                  15

Ser Pro Tyr Ile Lys Ile Phe Lys Asp Gly Arg Val Glu Arg Leu His
                20                  25                  30

Asn Ser Pro Tyr Val Pro Pro Ser Leu Asn Asp Pro Glu Thr Gly Val
            35                  40                  45

Ser Trp Lys Asp Val Pro Ile Ser Gln Val Ser Ala Arg Val Tyr
        50                  55                  60

Ile Pro Lys Ile Ser Asp His Glu Lys Leu Pro Ile Phe Val Tyr Val
 65                  70                  75                  80

His Gly Ala Gly Phe Cys Leu Glu Ser Ala Phe Arg Ser Phe Phe His
```

85                  90                  95
Thr Phe Val Lys His Phe Val Ala Glu Thr Lys Val Ile Gly Val Ser
            100                 105                 110

Ile Glu Tyr Arg Leu Ala Pro Glu His Leu Pro Ala Ala Tyr Glu
        115                 120                 125

Asp Cys Trp Glu Ala Leu Gln Trp Val Ala Ser His Val Gly Leu Asp
130                 135                 140

Asn Ser Gly Leu Lys Thr Ala Ile Asp Lys Asp Pro Trp Ile Ile Asn
145                 150                 155                 160

Tyr Gly Asp Phe Asp Arg Leu Tyr Leu Ala Gly Asp Ser Pro Gly Ala
                165                 170                 175

Asn Ile Val His Asn Thr Leu Ile Arg Ala Gly Lys Glu Lys Leu Lys
                180                 185                 190

Gly Gly Val Lys Ile Leu Gly Ala Ile Leu Tyr Tyr Pro Tyr Phe Ile
                195                 200                 205

Ile Pro Thr Ser Thr Lys Leu Ser Asp Asp Phe Glu Tyr Asn Tyr Thr
        210                 215                 220

Cys Tyr Trp Lys Leu Ala Tyr Pro Asn Ala Pro Gly Gly Met Asn Asn
225                 230                 235                 240

Pro Met Ile Asn Pro Ile Ala Glu Asn Ala Pro Asp Leu Ala Gly Tyr
                245                 250                 255

Gly Cys Ser Arg Leu Leu Val Thr Leu Val Ser Met Ile Ser Thr Thr
                260                 265                 270

Pro Asp Glu Thr Lys Asp Ile Asn Ala Val Tyr Ile Glu Ala Leu Glu
        275                 280                 285

Lys Ser Gly Trp Lys Gly Glu Leu Glu Val Ala Asp Phe Asp Ala Asp
290                 295                 300

Tyr Phe Glu Leu Phe Thr Leu Glu Thr Glu Met Gly Lys Asn Met Phe
305                 310                 315                 320

Arg Arg Leu Ala Ser Phe Ile Lys His Glu
                325                 330

<210> SEQ ID NO 7
<211> LENGTH: 319
<212> TYPE: PRT
<213> ORGANISM: Catharanthus roseus
<220> FEATURE:
<221> NAME/KEY: MISC_FEATURE
<223> OTHER INFORMATION: HL2 (Hydrolase 2)

<400> SEQUENCE: 7

Met Gly Ser Ser Asp Glu Thr Ile Phe Asp Leu Pro Pro Tyr Ile Lys
1               5                   10                  15

Val Phe Lys Asp Gly Arg Val Glu Arg Leu His Ser Ser Pro Tyr Val
            20                  25                  30

Pro Pro Ser Leu Asn Asp Pro Glu Thr Gly Gly Val Ser Trp Lys Asp
        35                  40                  45

Val Pro Ile Ser Ser Val Val Ser Ala Arg Ile Tyr Leu Pro Lys Ile
    50                  55                  60

Asn Asn His Asp Glu Lys Leu Pro Ile Ile Val Tyr Phe His Gly Ala
65                  70                  75                  80

Gly Phe Cys Leu Glu Ser Ala Phe Lys Ser Phe Phe His Thr Tyr Val
                85                  90                  95

Lys His Phe Val Ala Glu Ala Lys Ala Ile Ala Val Ser Val Glu Phe
            100                 105                 110

```
Arg Leu Ala Pro Glu Asn His Leu Pro Ala Ala Tyr Glu Asp Cys Trp
            115                 120                 125

Glu Ala Leu Gln Trp Val Ala Ser His Val Gly Leu Asp Ile Ser Ser
        130                 135                 140

Leu Lys Thr Cys Ile Asp Lys Asp Pro Trp Ile Ile Asn Tyr Ala Asp
145                 150                 155                 160

Phe Asp Arg Leu Tyr Leu Trp Gly Asp Ser Thr Gly Ala Asn Ile Val
                165                 170                 175

His Asn Thr Leu Ile Arg Ser Gly Lys Glu Lys Leu Asn Gly Gly Lys
            180                 185                 190

Val Lys Ile Leu Gly Ala Ile Leu Tyr Tyr Pro Tyr Phe Leu Ile Arg
        195                 200                 205

Thr Ser Ser Lys Gln Ser Asp Tyr Met Glu Asn Glu Tyr Arg Ser Tyr
    210                 215                 220

Trp Lys Leu Ala Tyr Pro Asp Ala Pro Gly Gly Asn Asp Asn Pro Met
225                 230                 235                 240

Ile Asn Pro Thr Ala Glu Asn Ala Pro Asp Leu Ala Gly Tyr Gly Cys
                245                 250                 255

Ser Arg Leu Leu Ile Ser Met Val Ala Asp Glu Ala Arg Asp Ile Thr
            260                 265                 270

Leu Leu Tyr Ile Asp Ala Leu Glu Lys Ser Gly Trp Lys Gly Glu Leu
        275                 280                 285

Asp Val Ala Asp Phe Asp Lys Gln Tyr Phe Glu Leu Phe Glu Met Glu
    290                 295                 300

Thr Glu Val Ala Lys Asn Met Leu Arg Arg Leu Ala Ser Phe Ile
305                 310                 315

<210> SEQ ID NO 8
<211> LENGTH: 1668
<212> TYPE: DNA
<213> ORGANISM: Catharanthus roseus
<220> FEATURE:
<221> NAME/KEY: misc_feature
<223> OTHER INFORMATION: SGD (Strictosidine beta-glucosidase)

<400> SEQUENCE: 8
atgggatcta aagatgatca gtcccttgtt gttgccattt ctccagctgc tgaaccaaat      60
ggaaatcatt ctgtccccat cccattcgcc taccccagta tcccattca  acctagaaag    120 cacaacaagc ccatcgttca tcgtcgagat ttcccctcag atttcatctt gggtgccgga    180
ggatctgctt atcagtgtga gggtgcatat aatgaaggca accgcggtcc cagtatatgg    240
gatactttca caaccgata tccagccaaa atagctgatg gatctaatgg caatcaagcc     300
atcaattctt acaatttgta caaggaagat atcaagatta tgaagcaaac aggcttggaa    360
tcatataggt tttcaattc atggtcaaga gtattgccag gtggaaatct atccggtgga    420
gtgaataaag atggtgtcaa gttctatcat gactttatag atgagcttct agccaatggc    480
atcaaaccct ttgcaactct cttccactgg gatcttcccc aagctcttga agacgagtat    540
ggaggcttct tgagtgatcg aattgtggaa gattttacgg agtatgcaga attttgcttt    600
tgggaattcg gtgacaaagt aaaattttgg acgactttca tgaaccaca tacttatgtt     660 gcaagtggat atgccactgg tgaatttgca ccaggaagag gtggtgcaga tggcaagggg    720
aaccctggca agaaccccta tagcgacaca taatttac  ttctttctca caaagctgct    780
gtggaagtat ataggaaaaa ttttcagaaa tgtcaaggag gtgaaattgg aattgtactt    840
aattcaatgt ggatggagcc tctcaatgaa accaagaag atattgatgc tcgggaaagg    900
```

```
ggtcctgatt tcatgctcgg atggttcata gagccattaa caacgggtga atacccaaaa      960
tccatgagag ctcttgtagg aagccgtctt ccagaatttt caacagaaga ttccgaaaaa     1020
ttaacaggat gctatgattt tatcggaatg aattattata caactactta tgtttctaat     1080
gcagacaaaa ttcccgatac tccgggttac gaaacagatg ctcgaattaa taagaatatt     1140
tttgtcaaaa aagttgatgg gaaggaagtg cgcattggtg aaccgtgcta tgggggatgg     1200
cagcatgttg ttccatctgg actctacaat ctcttggttt acactaagga gaaataccat     1260
gttccagtga tttatgtctc agaatgtggt gtggttgagg aaaatagaac caacatatta     1320
cttacagaag gtaaaaccaa catattactt acagaagctc gtcacgataa actcagggtt     1380
gattttctac aaagtcatct cgctagcgtg cgagatgcta ttgatgatgg tgtgaatgta     1440
aaaggattct ttgtttggtc attcttcgac aacttcgaat ggaatttggg atatatatgc     1500
cgttatggaa ttatccatgt tgattataaa acttttcaaa gatatccaaa ggattctgcc     1560
atatggtaca agaatttcat tagtgaagga tttgttacga atacagctaa aaagagattc     1620
cgagaagaag ataaactagt tgagttagtc aagaagcaaa aatactaa                  1668

<210> SEQ ID NO 9
<211> LENGTH: 1095
<212> TYPE: DNA
<213> ORGANISM: Catharanthus roseus
<220> FEATURE:
<221> NAME/KEY: misc_feature
<223> OTHER INFORMATION: GS (Geissoschizine synthase)

<400> SEQUENCE: 9
atggccggag aaacaaccaa actcgacctt tcagtgaagg ctgtgggatg gggtgctgca       60
gatgcatctg gtgtccttca gcccatcaag ttctatagaa gagtccctgg tgaacgggat      120
gtgaagatta gagttttgta ctctggtgtt tgcaatttcg atatggaaat ggtcagaaac      180
aagtggggtt tcaccagata tccttatgtg tttggacatg aaactgccgg tgaggtggta      240
gaagttggca gcaaagtaga gaaattcaag gttggagaca aggtagctgt gggatgtatg      300
gtcggatctt gtggtcaatg ttataattgt caaagtggaa tggagaatta ctgcccagag      360
cccaatatgg ctgatggatc tgtttaccgt gagcaagggg aacgatccta tgggggttgt      420
tcaaatgtga tggttgttga tgaaaagttc gtcctccgat ggcccgaaaa cttgcctcaa      480
gataaagggg ttgctctcct tgtgctgggg ttgttgtttt atagcccaat gaaacatttg      540
ggactcgata agccaggaaa gcatattggg gttttcgggc tgggaggtct tggttctgtt      600
gctgttaagt ttattaaggc ttttggtggt aaggctactg ttattagtac atcaaggcgt      660
aaggagaagg aagccattga gaacatggt gctgatgctt tgttgtcaa cactgactct      720 gagcaattga aggctctggc aggtactatg gatggtgttg tggacaccac cccaggtggc      780
cgcactccta tgtcacttat gctcaatttg ctcaagtttg acggcgcggt tatgctcgta      840
ggtgcaccgg agtcgctatt tgagctccct gcggcacctc tcattatggg aaggaaaaag      900
ataatcggaa gttccactgg aggtctcaaa gagtaccaag aaatgcttga tttcgcagcc      960
aaacataaca ttgtatgtga tactgaagtt attgggattg actatctcag cactgctatg     1020
gaacgtatca agaatttgga tgtcaagtac cgttttgcga ttgacattgg aaatacattg     1080
aaatttgagg aatga                                                      1095

<210> SEQ ID NO 10
<211> LENGTH: 1506
```

<212> TYPE: DNA
<213> ORGANISM: Catharanthus roseus
<220> FEATURE:
<221> NAME/KEY: misc_feature
<223> OTHER INFORMATION: GO (Geissoschizine oxidase)

<400> SEQUENCE: 10

```
atggagtttt ctttctcctc accagctctc tacatagttt atttcttgct tttctttgtg      60
gtaaggcaat tattgaaacc caaaagtaag aaaaaattgc caccaggtcc aagaacacta     120
cccttaattg gaaaccttca tcaactctcg ggacctttac ctcatcgtac cctaaaaaat     180
ttgtccgata acatggtcc tttgatgcac gtgaaaatgg cgaacgttc ggcaattata      240
gtatcagatg caagaatggc aaaaatagtt cttcataata acggtttagc cgttgcagat     300
cggtcagtaa atactgtcgc aagtattatg acttataata gtttgggtgt tacctttgct     360
cagtatggag attacttaac aaaattacgt caaatctata ctttggaact tttaagtcag     420
aaaaaagttc gatctttcta cagttgtttt gaagatgaac tcgatacttt tgttaagtca     480
attaagtcta acgttggaca acctatggtt ttgtacgaga aagcttctgc ttatttgtat     540
gctaccattt gtagaactat ttttgggagt gtttgcaagg aaaaggagaa aatgattaag     600
atagtgaaga aaacgtcgtt actgtctgga acaccactta gattggagga tctttttcct     660
tctatgagca ttttttgtag atttagtaaa actttgaatc aattgagagg acttttgcaa     720
gaaatggatg atattttgga gaaaatcata gttgaaaggg aaaaggcttc tgaagtctca     780
aaagaggcaa aggatgatga agatatgctt agtgttctgt tgaggcataa atggtacaat     840
ccaagtggtg ctaaattcag aatcactaat gcagacatca aagccattat ctttgagttg     900
atcttagcag caaccctaag tgtagcagat gttacagaat gggctatggt tgaaattcta     960
agggatccca aaagtttgaa aaagtgtac gaagaagtac gaggtatttg taagaaaag    1020
aaaagagtga caggatacga cgttgaaaaa atggaattta tgcgtctttg tgtgaaggaa    1080
tcaacaagaa tacatccagc tgctcctctt ttagttccta gagaatgcag agaagatttt    1140
gaagtagatg gatacacagt tccaaagggg gcttgggtta taacaaattg ctgggctgtt    1200
caaatggatc ctacagtatg gcccgaacca gagaagtttg atccagaaag atatattcgt    1260
aacccaatgg atttctatgg aagtaacttt gaattgatac catttgggac aggtagaaga    1320
ggatgtcctg gtattttata tggagtgaca aatgctgagt ttatgttggc tgctatgttt    1380
tatcattttg attgggaaat agcagatggt aaaaaaccag aagaaattga tttgactgag    1440
gactttggtg ctggttgcat tatgaagtat cctttgaaat tggttcctca tcttgttaac    1500
gattag                                                                1506
```

<210> SEQ ID NO 11
<211> LENGTH: 1065
<212> TYPE: DNA
<213> ORGANISM: Catharanthus roseus
<220> FEATURE:
<221> NAME/KEY: misc_feature
<223> OTHER INFORMATION: REDOX 1 (Reductase 1)

<400> SEQUENCE: 11

```
atggctgatc gcgtgaagac cgtaggatgg gcagctcacg acagctccgg cttcctctct      60
cccttccaat tcactcgaag ggcaacaggt gaagaagatg tgaggttgaa ggtgttgtac     120
tgtggtgtct gtcactcaga ccttcataac atcaagaacg aaatgggatt cacctcctac     180
ccttgtgtcc ccgggcatga ggttgtgggg gaagtgacgg aagtggggaa caaagtaaag     240
```

| | |
|---|---|
| aaattcataa ttggtgataa agttggggtt ggattattcg ttgactcatg tggcgaatgc | 300 |
| gaacaatgtg tgaatgatgt agaaacctat tgtcccaaat tgaaaatggc ttatttatcc | 360 |
| attgatgatg atggaactgt gattcaagga gggtactcaa aggaaatggt catcaaagaa | 420 |
| cgctacgttt tccggtggcc ggaaaatctt cctctacccg ccggtacacc gcttctgggt | 480 |
| gccggtagta cagtttatag tccaatgaaa tactatggac ttgataagtc aggacaacat | 540 |
| ctaggagttg ttggccttgg tggacttggt catttagctg ttaaatttgc aaaggctttt | 600 |
| ggacttaaag ttactgtcat tagtacctct cctagcaaga aggatgaagc catcaatcac | 660 |
| cttggtgctg atgcattttt agttagcact gatcaagagc aaacccagaa agcaatgagc | 720 |
| acaatggatg gcataattga cacagtatca gctcctcatg cattgatgcc attgttttcc | 780 |
| ctattgaaac caaatgggaa gctagttgtt gttggtgcac caaataaacc agttgaatta | 840 |
| gatattctat ttcttgtcat gggaaggaaa atgctcggaa catcttctgt tgggggagtg | 900 |
| aaggagacac aagagatgat cgattttgca gcaaaacatg gtatagttgc agatgtagaa | 960 |
| gttgtggaaa tggagaatgt gaacaatgca atggagcggc ttgcgaaggg ggatgttaga | 1020 |
| tatagatttg ttcttgatat tgggaatgca acagtagctg tctga | 1065 |

<210> SEQ ID NO 12
<211> LENGTH: 972
<212> TYPE: DNA
<213> ORGANISM: Catharanthus roseus
<220> FEATURE:
<221> NAME/KEY: misc_feature
<223> OTHER INFORMATION: REDOX 2 (Reductase 2)

<400> SEQUENCE: 12

| | |
|---|---|
| atggaaaagc aagttgagat ccctgaagta gaattgaatt caggacataa aatgccaatt | 60 |
| gtgggatacg gaacatgcgt gccagaaccc atgccaccgt tggaagaact aaccgcaatc | 120 |
| ttcttagatg caataaaggt tggttaccgg cacttcgaca cggcttcgag ttacggcaca | 180 |
| gaggaggcac ttggtaaagc catagctgag gctataaaca gcggtttggt taaaagtagg | 240 |
| gaggaattct tcatcagttg taagctgtgg attgaagatg cagatcatga ccttatcttg | 300 |
| cctgccctca accagtcact tcagattctt ggggttgatt atttggatct atatatgata | 360 |
| cacatgccgg tgagagtgag gaaaggtgct cccatgttca attattcaaa gaggatttc | 420 |
| cttccatttg acatacaagg tacatggaag gccatggaag agtgcagcaa acaaggattg | 480 |
| gccaagtcta ttggtgtcag caactactct gttgaaaaac tcactaaact cctagaaacc | 540 |
| tccactattc cccccgccgt taatcaggtt gagatgaatg tagcttggca acagagaaaa | 600 |
| ttgctgccat tttgcaaaga gaaaaacatt catataacat catggtctcc actcctatct | 660 |
| tatggtgtcg cttggggaag taatgctgtc atggaaaatc ctgttctcca acaaattgcg | 720 |
| gcttccaaag gcaaaactgt ggcacaggtg gcactaagat ggatatacga gcaaggagca | 780 |
| agtctcatta caaggacttc caacaaggac agaatgtttg aaaatgttca aattttgat | 840 |
| tgggaactca gtaaagaaga attggatcaa attcatgaaa tcccacaacg taggggtact | 900 |
| ttaggtgaag aatttatgca tccagaagga ccgatcaaat ccccagagga gctttgggat | 960 |
| ggagacttgt ga | 972 |

<210> SEQ ID NO 13
<211> LENGTH: 993
<212> TYPE: DNA
<213> ORGANISM: Catharanthus roseus
<220> FEATURE:

<221> NAME/KEY: misc_feature
<223> OTHER INFORMATION: HL1 (Hydrolase 1)

<400> SEQUENCE: 13

```
atgaattcct caactgatcc aacttcagat gagactattt gggatctttc tccatatatt      60
aaaattttca aagatggaag agtagaaaga ctccataata gtccttatgt tcccccatca     120
cttaatgatc cagaaactgg cgtttcttgg aaagatgtcc cgatttcatc acaagtttcc     180
gctagggtat acattccaaa atcagcgac catgaaaaac tccctatttt tgtgtatgtg      240
catggggctg gcttttgtct agaatctgcc ttcagatcat ttttccacac ttttgtcaaa     300
cacttcgtag ccgaaaccaa agttattggg gtttcgattg aatatagact tgccccagag     360
cacctttac ccgcagctta tgaagattgt tgggaagccc ttcaatgggt tgcttctcat      420
gtgggtctcg acaattccgg cctaaagaca gctattgata aagatccatg gataataaac     480
tatggtgatt tcgatagact gtatttggcg ggtgacagtc ctggtgctaa tattgttcac     540
aacacactta tcagagctgg aaaagagaaa ctgaagggcg gagtgaaaat ttgggggca      600
attctttact acccatattt cattatccca accagcacga aacttagtga tgattttgag     660
tataactaca catgttactg gaaattggct tatccaaatg ctcctggcgg gatgaataac     720
ccaatgataa accccatagc tgaaaatgct ccagacttgg ctggatacgg ttgctcgagg     780
ttgttggtta ccctggtttc catgatttca acgactccag atgagactaa agacataaat     840
gcggtttata ttgaggcatt agaaaagagt ggatggaaag gggaattgga agtggctgat     900
tttgacgcag attattttga actcttcacc ttggaaacgg agatgggcaa gaatatgttc     960
agacgtttag catctttcat caaacatgag taa                                  993
```

<210> SEQ ID NO 14
<211> LENGTH: 963
<212> TYPE: DNA
<213> ORGANISM: Catharanthus roseus
<220> FEATURE:
<221> NAME/KEY: misc_feature
<223> OTHER INFORMATION: HL2 (Hydrolase 2)

<400> SEQUENCE: 14

```
atgggttcct cagatgagac tatttttgat cttcctccat acatcaaagt cttcaaagat      60
ggaagagtag aaagactcca ttcttcccca tatgttcccc catctcttaa tgatccagaa     120
accggtggag tctcttggaa agacgtccca atttcttcag tagtttcagc tagaatttac     180
cttcctaaaa tcaacaacca tgatgaaaaa ctccccatta gtctatttt ccatggagct      240
ggttttttgtc ttgaatcggc cttcaaatca tttttccaca cttatgtgaa acactttgta     300
gcagaagcca aagctattgc ggtttctgtt gagttcaggc tcgcccctga aaaccattta     360
cccgcagctt atgaagattg ctgggaagcc cttcaatggg ttgcttctca tgtgggtctc     420
gacatttcca gcttgaagac atgtattgat aaagatccat ggataatcaa ctatgccgat     480
ttcgatagac tctatttgtg gggtgatagc accggtgcca atattgttca acacacactt     540
atcagatctg gtaaagagaa attgaacggc ggcaaagtga agattttggg ggcaattctt     600
tactacccat atttcttaat caggacgagt tcaaaacaga gtgattatat ggagaatgag     660
tatagatctt actggaaatt ggcttaccca gatgctcctg gtggaaatga taccccaatg     720
ataaacccta cagctgagaa tgctcctgat ctggctggat atggttgctc gaggttgctg     780
atttccatgg ttgccgatga agctagagat ataactcttc tttatattga tgcattggaa     840
aagagtggat ggaaaggtga attagatgtg gctgattttg ataaacagta ttttgaactg     900
```

```
tttgaaatgg aaacagaggt tgccaagaac atgctcagac gtttagcttc tttcatcaag    960
taa                                                                  963

<210> SEQ ID NO 15
<211> LENGTH: 1266
<212> TYPE: DNA
<213> ORGANISM: Catharanthus roseus
<220> FEATURE:
<221> NAME/KEY: misc_feature
<223> OTHER INFORMATION: SAT (stemmadenine acetyltransferase)

<400> SEQUENCE: 15
atggcacccc agatgcagat attgtcagag gaactgattc aaccatcatc tccgacaccc     60
caaaccttga aacccataa actttcccat cttgatcaag ttttattaac atgtcatatc    120
cctattattc tcttttatcc aaatcaattg gactcaaatc tcgatcgagc ccaaagatct    180
gagaatctaa aacgatcttt atcaacagtg ttaactcaat tttacccttt agccggaaga    240
atcaatataa attcttccgt agattgtaat gattccggag tccctttttct tgaagctcga    300 gttcattccc aactctcaga agcaattaaa aatgtcgcca tagatgaact caatcaatac    360
ctgccattcc aaccttatcc cggtggggag gaaagtgggt tgaaaaaaga tatcccctta    420
gctgtaaaaa tcagttgttt cgaatgtggc ggaacagcaa ttggggtctg tatttcccac    480
aagattgccg atgcgttgtc cttggctacc ttcctcaatt catggaccgc aacatgccag    540
gaagagactg atattgttca acctaatttc gatctgggat cccatcattt tccgcctatg    600
gaaagcatcc cagcacctga atttctaccg gatgaaaata ttgtgatgaa acggttcgtg    660
ttcgataaag aaaaattaga agctctaaaa gcccaattag cttcctctgc aacagaagtg    720
aagaattcaa gtcgggtaca aattgttatt gctgttatat ggaagcaatt cattgacgtg    780 accgggcaa aattcgatac caagaacaaa ttagtagcag ctcaagcagt gaatttgaga    840
tcaagaatga atccaccatt tcctcaatct gctatgggga atatagccac aatggcatat    900
gccgttgcag aggaggataa ggattttca gatcttgtcg gtccattgaa aaccagtctt    960
gcaaaaattg atgatgaaca tgttaaagaa ttacaaaaag gagtaacata tttggattat   1020
gaagctgaac cacaagaatt gttctctttt agtagttggt gcaggcttgg gtttatgat   1080 ttggattttg gatggggaaa gcctgtttct gtttgtacaa caactgtgcc tatgaagaat   1140
ttggtatatt tgatggatac aagaaatgaa gatggaatgg aagcatggat cagcatggct   1200
gaagatgaga tgtctatgct ttcctctgat tttctttcac ttctggacac tgattttagc   1260
aattga                                                             1266

<210> SEQ ID NO 16
<211> LENGTH: 421
<212> TYPE: PRT
<213> ORGANISM: Catharanthus roseus
<220> FEATURE:
<221> NAME/KEY: MISC_FEATURE
<223> OTHER INFORMATION: SAT (stemmadenine acetyltransferase)

<400> SEQUENCE: 16

Met Ala Pro Gln Met Gln Ile Leu Ser Glu Glu Leu Ile Gln Pro Ser
1               5                   10                  15

Ser Pro Thr Pro Gln Thr Leu Lys Thr His Lys Leu Ser His Leu Asp
            20                  25                  30

Gln Val Leu Leu Thr Cys His Ile Pro Ile Ile Leu Phe Tyr Pro Asn
        35                  40                  45
```

Gln Leu Asp Ser Asn Leu Asp Arg Ala Gln Arg Ser Glu Asn Leu Lys
    50                  55                  60

Arg Ser Leu Ser Thr Val Leu Thr Gln Phe Tyr Pro Leu Ala Gly Arg
65                  70                  75                  80

Ile Asn Ile Asn Ser Ser Val Asp Cys Asn Asp Ser Gly Val Pro Phe
                85                  90                  95

Leu Glu Ala Arg Val His Ser Gln Leu Ser Glu Ala Ile Lys Asn Val
            100                 105                 110

Ala Ile Asp Glu Leu Asn Gln Tyr Leu Pro Phe Gln Pro Tyr Pro Gly
        115                 120                 125

Gly Glu Glu Ser Gly Leu Lys Lys Asp Ile Pro Leu Ala Val Lys Ile
    130                 135                 140

Ser Cys Phe Glu Cys Gly Gly Thr Ala Ile Gly Val Cys Ile Ser His
145                 150                 155                 160

Lys Ile Ala Asp Ala Leu Ser Leu Ala Thr Phe Leu Asn Ser Trp Thr
                165                 170                 175

Ala Thr Cys Gln Glu Glu Thr Asp Ile Val Gln Pro Asn Phe Asp Leu
            180                 185                 190

Gly Ser His His Phe Pro Pro Met Glu Ser Ile Pro Ala Pro Glu Phe
        195                 200                 205

Leu Pro Asp Glu Asn Ile Val Met Lys Arg Phe Val Phe Asp Lys Glu
    210                 215                 220

Lys Leu Glu Ala Leu Lys Ala Gln Leu Ala Ser Ser Ala Thr Glu Val
225                 230                 235                 240

Lys Asn Ser Ser Arg Val Gln Ile Val Ile Ala Val Ile Trp Lys Gln
                245                 250                 255

Phe Ile Asp Val Thr Arg Ala Lys Phe Asp Thr Lys Asn Lys Leu Val
            260                 265                 270

Ala Ala Gln Ala Val Asn Leu Arg Ser Arg Met Asn Pro Pro Phe Pro
        275                 280                 285

Gln Ser Ala Met Gly Asn Ile Ala Thr Met Ala Tyr Ala Val Ala Glu
    290                 295                 300

Glu Asp Lys Asp Phe Ser Asp Leu Val Gly Pro Leu Lys Thr Ser Leu
305                 310                 315                 320

Ala Lys Ile Asp Asp Glu His Val Lys Glu Leu Gln Lys Gly Val Thr
                325                 330                 335

Tyr Leu Asp Tyr Glu Ala Glu Pro Gln Glu Leu Phe Ser Phe Ser Ser
            340                 345                 350

Trp Cys Arg Leu Gly Phe Tyr Asp Leu Asp Phe Gly Trp Gly Lys Pro
        355                 360                 365

Val Ser Val Cys Thr Thr Thr Val Pro Met Lys Asn Leu Val Tyr Leu
    370                 375                 380

Met Asp Thr Arg Asn Glu Asp Gly Met Glu Ala Trp Ile Ser Met Ala
385                 390                 395                 400

Glu Asp Glu Met Ser Met Leu Ser Ser Asp Phe Leu Ser Leu Leu Asp
                405                 410                 415

Thr Asp Phe Ser Asn
            420

<210> SEQ ID NO 17
<211> LENGTH: 1098
<212> TYPE: DNA
<213> ORGANISM: Amsonia hubrichtii
<220> FEATURE:

<221> NAME/KEY: misc_feature
<223> OTHER INFORMATION: GS (Geissoschizine synthase)

<400> SEQUENCE: 17

```
atggctggag aatcaaccca acttgacctt tcggtgaagg ctattggatg gggtgctaaa      60
gatgcatctg gggaacttca tgccatcaag ttctcaagaa gggcccctgg tgagcgcgat     120
gtgaagataa gagttttata ctgtggtatc tgcaattttg acatggaaat ggtcaggaac     180
aaatggggtt tcactagata tccttacgta tttggacatg agaccgccgg agaagttgta     240
gaagttggca gcaaggtgca gaaattcaag gttggtgaca agtggctgt ggggtgcatg      300
gttgggtctt gcgaaaaatg ttacaattgt gaaaatggta tggaaaatta ctgtccagag     360
cccaacatgg ctgatggttc tgtttaccgt gaacaaggag agcgttccta tggtggctgt     420
tccaatgtca tggttgttga tgagaaattc gtgctccgtt ggccggaaaa tttccctcaa     480
gatactggcg ttcctctact ttgtgctggg gttgttgttt atagcccatt gaaacatgtt     540
ggactcgaca aacctggaat gcacattggt gttttttggcc tcggaggtct tggttctata   600
gctgtcaagt atattaaggc ttttggtggt aaggcaactg tgatcagtac atcaaagcgt    660
aaggagaagg aagccattga agagcacggt gcagatgcat ttgttgtaaa cagtgatact    720
gaacaattgc aggctttaac aggaacaatg gatggtgtaa ttgacactac cccaggtgga   780
cgaactccta tggcactcat gctcaatttg ctaaagtttg acggaacagt gatacttgtt   840
ggtgcaccag aaacactatt tgagctccca gtgcaacctc taattcttgg gaggagaaag   900
gtaattggga gctccactgg aggtctgagg gagtaccaag agatgcttga ctttctcagcc  960
aaacacaaca ttttatgtga tactgaggtg atcccgattg actatctcag cactgccatg    1020
gagcgcatca gaatctgga tgtcaaatac cgatttgtga ttgacattgg aaatacactg     1080
aaatatgatg aagaatga                                                  1098
```

<210> SEQ ID NO 18
<211> LENGTH: 1067
<212> TYPE: DNA
<213> ORGANISM: Tabernaemontana elegans
<220> FEATURE:
<221> NAME/KEY: misc_feature
<223> OTHER INFORMATION: GS (Geissoschizine synthase)

<400> SEQUENCE: 18

```
tctctgtcaa ggctgtcggc tggggtgctg ctgatgcatc tgggactctt cagcccatca     60
aattcttcag aagggtacct ggcgaacgcg atgtgaagat cagagttttg tattgtggtg   120
tttgcaattt tgatatggaa atggtcagaa acaaatgggg ttttactaga tatccttatg   180
tatttggaca cgaaaccgcg ggtgaggtgg tagaagttgg gagcaaggtt gggaaattca   240
aggttggaga caaagtagct gtgggatgta tggtgggatc ttgtgggaaa tgtttaaatt   300
gtgaaactgg atttgaaaat tactgcccag aacccaatat ggctgatggt tctgtttatc   360
gtgaacaagg agagagatct tatggggggtt gttctaatgt aatggttgtt gatgagaaat   420
tcgtcctccg atggcccgaa aactaccctc aagataccgg tgttcctatc ctctgtgctg   480
ggattgttgt ttacagtcca ttgaaacata tgggacttga taaacccgga aagcatatcg   540
gtgttttttgg gtttggaggt attggtgcta tggctgttaa atttattaag gcctttggtg   600
gtaaagctac ggttattagt acatcaaagc gtaaggagaa ggaagccatt gaagaacatg   660
gtgctgatga ctttgttgtc aacactgaca ctgagaaatt gcaggcttta gctggtacta   720
tggatggtgt tgttgatact accccctggtg gacgaactcc catgtcactg atgctcaatt   780
```

```
tgttgaagtt tgatggcgct gttctacttg ttggtgcacc agagacacta tttgagcttc      840
cagtccaacc tctcatcctt ggaaggagaa agataattgg gagctcaact ggaggtctaa      900
aggaatatca agcgatgctt gattttgcag cccaacataa cattatatgt gatactgagg      960
ttattggaat tgactatctt gagactgcca tggaacacat caggaatctg gatgtcaagt     1020
accgattttc gattgatatt ggaaatacat tgaaatttga ggaatga                   1067

<210> SEQ ID NO 19
<211> LENGTH: 1095
<212> TYPE: DNA
<213> ORGANISM: Vinca minor
<220> FEATURE:
<221> NAME/KEY: misc_feature
<223> OTHER INFORMATION: GS (Geissoschizine synthase)

<400> SEQUENCE: 19
atggctgcag aaacaaccca actcgatctc tctgtcaagg ctgtcggctg gggtgctgct       60
gatgcatctg ggactcttca gcccatcaaa ttcttcagaa gggtacctgg cgaacgcgat      120
gtgaagatca gagttttgta ttgtggtgtt tgcaattttg atatggaaat ggtcagaaac      180
aaatggggtt ttactagata tccttatgta tttggacacg aaaccgcggg tgaggtggta      240
gaagttggga gcaaggttgg gaaattcaag gttggagaca agtagctgt gggatgtatg       300 gtgggatctt gtgggaaatg tttaaattgt gaaactggat tgaaaatta ctgcccagaa       360 cccaatatgg cagatggctc tgtttatcgc gaacaaggag agagatctta tggggggttgt    420 tctaatgtaa tggttgttga tgagaaattt gtcctccgat ggcccgaaaa ctaccctcaa      480
gataccggtg ttcctatcct ctgtgctggg attgttgttt atagtccatt gaaacatatg      540
ggacttgaca aacctggaaa acatattggt gttttttggt ttggaggtat tggtgctatg      600
gctgttaaat ttattaaggc ctttggtggt aaagctacgg ttattagtac atcaaagcgt      660
aaggagaagg aagccattga gaacatggt gctgatgact ttgttgtcaa cactgacact       720
gagaaattgc aggctttagc tggtactatg gatggtgttg ttgatactac ccctggcgga     780
cgaactccca tggcactcat gctcagtttg cttaagtttg atggctctgt tatacttgtt    840
ggtgcaccag agtgcctatt tgagcttcca gtccaacctc tcattgttgg aaggagaaag     900
ataattggta gctcaactgg aggtctcaag gagtatcaag atgcttga ttttgcagcc       960 caacataaga ttatgtgtga tactgaggtt attggtattg actatcttga tactgccatg    1020
gaacgcatca ggaatcttga tgtcaagtac cgattttcaa ttgatattgg caatacattg    1080
aaatttgagg aatga                                                    1095

<210> SEQ ID NO 20
<211> LENGTH: 1506
<212> TYPE: DNA
<213> ORGANISM: Amsonia hubrichtii
<220> FEATURE:
<221> NAME/KEY: misc_feature
<223> OTHER INFORMATION: GO (Geissoschizine Oxidase)

<400> SEQUENCE: 20
atggagttct ctttctcctc accacttctc tacatcgtct acttcttgct tttctttctc       60
gtaaggtatc tgttaaagcc caaaagcaac aagaaattgc ccccaggtcc tagaacacta     120
cccataatcg gaaacttgca ccagcttatg ggaccattgc ctcatcgcac tctcaaggag     180
ttgtctgata gacatggacc tttgatgcac gtgaagatgg gtgaacgttc agcaattatc     240
```

-continued

```
gtatccaatg caagaatggc gaaaatagtc ctgcacaatc atggacttgc ggtggctgac      300
cggtcggtga atactgttgc tagcatcatg acctacaaca gtttgggagt tacatttgct      360
caatatggtg attacttgac gaagctgcgt cagatttaca ctttggaact cctgagtccg      420
aagaaagttc gatcgttcta cggttgcttc gaagaggagc ttgatgtttt tgttgagtca      480
atcaagtctt cagtgggaca acccatggta atgtacgaga aatgttctaa atacttgtat      540
gccaccattt gcagaactat ttttggaagt gtatgcaagg agagggagaa gatgatcaag      600
atagttaaaa aaacatcatt actctctgga accccccctca ggttggagga tttgttccct      660
tcaatgagtg tgtttgccag gttcagcaaa acactgaagc agttgagagg tctgttacag      720
gaaatggatg atattcttga ggacattatc actgagcgtg aaaagactac tgaaatctcg      780
acagaatcaa aggacgatga agatatgctt agcgtcctac tcaggcataa atggcacaac      840
cccagcggtg caaaattcag aatcaccaac gcagacatca aagccatcat ttttgagttg      900
atcttagcag caactcttag tgtagcagat gttgcagagt gggcgatggt ggaaatactg      960
agggatccca aaagtttgaa gaaggtatac gaagaagtca gggaagtctg caaggaaaag     1020
aagaaagtca ctggacatga cgttgagaaa ttggaattca tgcgcctttg tctcaaggaa     1080
tctacaagaa tacaccctgc tgcacctctc ttagtcccca gagaatgcag agaagatttc     1140
gaggtcgatg gatacacagt tccaaaagga gcatgggtgt tgacaaactg ctgggcagtc     1200
caaatggatc ctgaggtctg gccagagcct gagaagtttg atccagagag atacattcgt     1260
aatcccatgg atttctatgg aagcagcttt gagttgatac ctttcggaac aggaaggaga     1320
ggatgtccag gaatcttgta tggagtgacc aatgctgagc ttatgttagc tgcaatgttc     1380
taccatttcg attgggagat tgcagatggg aaaaaaccag aagaaataga catgactgag     1440
gactttggtg caggttgcat tatgaaatat cctttgaaat tggttcctca tcttgcaaaa     1500
aattga                                                              1506
```

<210> SEQ ID NO 21
<211> LENGTH: 1518
<212> TYPE: DNA
<213> ORGANISM: Tabernaemontana elegans
<220> FEATURE:
<221> NAME/KEY: misc_feature
<223> OTHER INFORMATION: GO (Geissoschizine Oxidase)

<400> SEQUENCE: 21

```
atgaggagaa gatggagatt gaaggatgat tttccagctc tctacatcct ctacttcttg       60
cttttccttc ttgtaaagca actgttaaag cccaaaagcc agaagaaatt gccaccaggt      120
cctaggacgc tacccataat cggaaacttg caccagctta tgggaccact gcctcatcgc      180
accctcaagg atttgtccga taacatggac ccactcatgc acttgaagat gggtgaacgt      240
tcagcaatta tcgtatcgga tgcaagaatg gcaaaaatcg tcctgcacaa tcatgggctt      300
gcagtggcgg accggtcggt gaatactgtt gctagcatca tgacctacaa cagtttgggg      360
gttacatttg ctcaatatgg tcgattacttg acaaagctgc gtcagattta cactttggaa      420
ctccttagtc ctaaaaaagt tcgatcattt tacagttgtt ttgaagacga gcttgatggg      480
tttgtgaaat caatcaagtc tcaagtcgga caacccatgg ttttgtacga aaagcttct      540 acttacttgt atgccacaat ttgcagaact atttttggaa gcatatgcaa ggagagggag      600
aagatgatca agatagtgaa agaaacatca ttactctctg gaaccccctct caggttggag      660 gatctgttcc cttcaatgag agtgttttgt aggttcagca aacactgaa ccaattgagg      720
```

```
ggtctgttac aggaaatgga cgatattctt gaggatatta tcattgagcg tgaaaagacc    780
actgaaatct cgacagaggc caaggatgac gaagatatgc tcagcgttct cctgcggcat    840
aaatggcaca atcccagcgg cgcaaaattc agaatcacaa acgcagacat caaagccatc    900
atttttgagt tgatcttagc agcaactctt agtgtagcag atgttacaga atgggctatg    960
gttgaaatac tgagggatcc caaaagtttg aagaaggtat acgacgaagt cagagaagtc   1020
tgcaaggaaa agaaaagagt caccggatat gatgttgaga aattagaata tatgcacctt   1080
tgtgtaaagg aatctacaag aatacaccct gctgctcctc tcttagtccc gagagaatgc   1140
agagaagact tcgaggtgga cggatacact gttccaaaag gagcatgggt gttgacaaac   1200
tgctgggctg tccagatgga tcccaaaatc tggccggagc ctgagaagtt tgatccagag   1260
cgatacatcc gtaatcccat ggatttctac ggaagcaact ttgagctgat acccttggt    1320
acaggaagga gaggatgtcc aggaatcttg tttggagtga ccaatgctga gcttctctta   1380
gctgcaatgt tctatcattt tgattgggaa attgcagatg gaaaaaacc agaagaaata    1440
gatctcaccg aggactttgg tgctggttgc attatgaaat atccctttgaa actggttcca   1500
catcttgtaa atgaataa                                                 1518
```

<210> SEQ ID NO 22
<211> LENGTH: 1289
<212> TYPE: DNA
<213> ORGANISM: Vinca minor
<220> FEATURE:
<221> NAME/KEY: misc_feature
<223> OTHER INFORMATION: GO (Geissoschizine Oxidase)

<400> SEQUENCE: 22

```
atggagttct cttttcctc actacctctc tacatagcct ctttcttgct tttctttcta     60
gtaaagcaga tcttgaaacc caagagcgga aagaaattgc cccccggtcc aaggactctt    120
cccataattg gaaacttaca ccagcttatg ggacccttac ctcatcgaac cctcaaaaac    180
ttgtccgata acatggacc actcatgcat ttgaaattgg gtgaaaggtc cgccattatc     240
gtatcagatg caagattggc caaaatcgta ttgcataata atgggttagc agtggctgat    300
cgatcagtga acacagtcgc tagtattatg acttacaaca gtttaggcgt tacattcgca    360
caatatggcg attatttgac caaacttcgt cagatttaca ctttggaact tcttagtcaa    420
aagaaagttc gatctttta caattgtttc gaagatgaac ttgacacatt tgttaagtca    480
atcaagtctt cgaacggaca acctatggta ttgtacgagg tagcttctac ttacttgtac    540
gctacgattt gcagaactat ttttggaagt gtttgcaaag aaagagagaa gatgattaag    600
atagtgaaga gaacttcttt actgtctgga actcctctta gattggaaga tcttttttcct   660
tcaatgagcg tgttttgtag attcagcaaa acccttaacc aacttagggg tcttcttgat    720
gaaatggatc acattcttga ggatattatt gttgatcgtg aaaagaacac tgaaatctta    780
aaagaaggaa aagatgacga ggatatgctc agcgttctct tgaggcataa atggcacaat    840
cccagtggtg caaaattcag aatcgctaac gcagacatca aggctatcat ttttgagctg    900
attttagcgg cgactctaag tgtagcagat gttacagaat gggcaatggt tgaaataata    960
agagatccaa agagtttaa gaaggtacac gaggaagtaa gacaagtctg caaggacaag   1020
ggaaaagtaa cagggtacga tgttgagaaa ttggattatt tgcgtctttg tctcaaggaa   1080
tctacaagaa tccacccagc agcacctcta ttagtcccta gagaatgcag agaagatttc   1140
caggttgatg gattcacagt tccaaaagga gcatgggttt tgacaaactg ttgggcggtc   1200
```

| | |
|---|---|
| caaatggatc ctgaagtttg gcccgaaccc gagaagtttg atccggaaag atatataaga | 1260 |
| aagcccatgg atttctatgg aaatagctt | 1289 |

<210> SEQ ID NO 23
<211> LENGTH: 1242
<212> TYPE: DNA
<213> ORGANISM: Amsonia hubrichtii
<220> FEATURE:
<221> NAME/KEY: misc_feature
<223> OTHER INFORMATION: REDOX 1 (reductase 1)

<400> SEQUENCE: 23

| | |
|---|---|
| atgaaaaatc tactaccaaa tagattaaat agaaataaga aaaactggat caacaagcac | 60 |
| aaatcgacta ccttgagaga gatgagagaa ctaaaggctt ctgagataat ttgggagcag | 120 |
| aatctagcaa gaaaatacag ttctagatat agcggcaccg gcacacttct agaaaaaatg | 180 |
| gccgatcgta tgaaaaccat cggatgggca gctcacgata gctccggat cctctctcct | 240 |
| tttgaattca cccgaagggc aactggtgaa gaagatgtaa ggttgaaggt gctgtattgt | 300 |
| ggtatctgtc actccgacct tcataacatc aagaacgaaa tgggtttcac ttcatacct | 360 |
| tgtgtaccag gcatgaagt tgtaggtgaa gtaaccgagg ttgggagcaa agtaaagaaa | 420 |
| ttcaaagctg gtgacaaagt tggggtggga ttattcgtgg attcgtgtcg cgagtgcgag | 480 |
| caatgtgcaa atgatctaga gccctactgc cccaagttaa aactggcata tctgtccctt | 540 |
| gatgatgatg aaccgttat tcagggagga tactccaatg atggttgt caaggaacac | 600 |
| tatgtaaatc gctggccgga aactcttcct ctagacgctg gtgctccgct aataggtgcc | 660 |
| ggtagcactg tgtatagtcc aatgaaatat tatggacttg ataagccagg acaacatttg | 720 |
| ggagttgttg gccttggtgg acttggccat ttagctgtga aatttgccaa ggcttttgga | 780 |
| ctcaaagtta ctgtgattag tacctcccca aggaaaaagg aagaagccct caatcatcta | 840 |
| ggagctgact cattttggt cagcactgat caagagcaaa tgcagaaagc aatgagcaca | 900 |
| ttggatggca ttattgacac agtatcagct cctcatgcag tgatgccact gttttctta | 960 |
| ttgaaacctc atgggaagct aattgtagtt ggggcaccaa ataagccact tgaagtagat | 1020 |
| gttccatttc ttctcatggg aagaaaaatg ttaggagcat ctgctgttgg gggaatgaag | 1080 |
| gagactcaag aaatgcttga ttttgcagcc aaacatgata ttactgcaga tgttgaagtt | 1140 |
| gtgcctatgg actatgtgaa caaagctatg gaacgcttg agaagggtga tgtcaaatat | 1200 |
| cgatttgttc ttgacattgg gaatacattg ctagctgcct aa | 1242 |

<210> SEQ ID NO 24
<211> LENGTH: 1065
<212> TYPE: DNA
<213> ORGANISM: Tabernaemontana elegans
<220> FEATURE:
<221> NAME/KEY: misc_feature
<223> OTHER INFORMATION: REDOX 1 (reductase 1)

<400> SEQUENCE: 24

| | |
|---|---|
| atggctgatc gagtcaagac catcggatgg gcagctcatg acagctccgg gatcctctct | 60 |
| cctttttgaat tcacccgaag ggcaactggc aatgaagatg taaggtttaa ggtgctatat | 120 |
| tgtggtatct gtcactccga ccttcacaac gtcaagaacg aaatgggctt cacttcatac | 180 |
| ccttgtgtac cggggcatga agttgtaggt gaagtgacgg aggttggaag caaagtcaag | 240 |
| aaattcaaag caggagacaa agttggagta ggattattcg tcgattcgtg tcgcgaatgc | 300 |
| gaacagtgta aaaatgatct agagccctac tgccccaagt tgaaaatggc ctatctgtcc | 360 |

```
cctgatgatg atggaaccat tattcaggga ggatactcta acgagatggt agtcaaggaa      420
cactatgtac ttcggtggcc tgaaactctt cctctcgatg ctggtgcacc gctagttggt      480
gccggtagca ctgtctatag tccaatgaag tattatggac ttgataagcc aggacaacat      540
ttgggagttg ttggccttgg tggacttggc cacttagctg tgaaattcgc caaggcattt      600
ggactcaaag ttaccgtgat cagtacctcc cctaggaaaa aggaagaagc catcactcac      660
ctaggagctg actcattttt ggtcagcaca gatcaagagc aaatgcagaa agcaacgagc      720
accttagatg gtatcattga cacggtatca gctcctcatg cagtgatgcc attgtttttc      780
ttattgaaac ctcacgggaa gcttattgtg gttgggcac caaataagcc acttgaagtt      840
gatgttccat tcttcttat gggaagaaaa atgctgggag catctgcggt cggaggaatg      900
aaggagactc aagaaatgct tgattttgca gcagaacaca atatcactgc agatattgaa      960
gttgtgccaa tggactatgt gaacaaagct ctcgagcgcc ttgagaaagg cgatgttagg     1020
tatcgctttg ttcttgatat tgggaataca atggcagccg cctag                     1065
```

<210> SEQ ID NO 25
<211> LENGTH: 1059
<212> TYPE: DNA
<213> ORGANISM: Vinca minor
<220> FEATURE:
<221> NAME/KEY: misc_feature
<223> OTHER INFORMATION: REDOX 1 (reductase 1)

<400> SEQUENCE: 25

```
atgactggtc gtgtaaaaac catcggatgg gcggctcacg acaaatccgg cgtactctcc       60
cctttcgaat tcactagaag agcaactggg gatgaagatg taaggttgaa ggtgttgtac      120
tgtggtgtct gtcactcgga ccttcatatc atcaagaacg aaatggaatt cacttcatac      180
ccttgcgtac cagggcatga agtagtaggt gaagtgacag agactgggag aaaagtagag      240
aaattcaaag ttggagacaa agtaggagtt ggattattcg tggaatcatg tagggaatgc      300
gagcaatgta ctaatgattt agagccctat tgccccaaga tgaaaatgac atatttatcc      360
cttgatgatg atggaattgt taatcaagga ggatattcca aggagatggt tgtcaaagaa      420
ccctttgtat ttcggtggcc ggaaactcta cccctcgccg ccggtgctcc gcttctcgga      480
gccggaagca ctgtttatag tccaatgaag tattatgaac ttgataagcc aggacaacat      540
ttgggagttg ttggtctagg tggacttggt catttagctg tcaaatttgc caaggcttta      600
ggactcaaag ttaccgtcat tagtacctct cccagtaaga agaagaagc cataaaaaac      660 cttggagctg atgcattttt ggtcagcact gatcaagagc aaatgcagaa agcaatgagc      720
acaatggatg gcatcattga cacagtatca gcttctcatg cagcgatgcc attgattttt      780
ctattgaaac ctcacggaaa actaattgta gttggtgcac caaataagcc acttcaacta      840
gatattccat tcttcgttat gggaagaaaa atgctaggaa catctgcggt cggaggaatg      900
aaggagactc aagaaatgct tgattttgca gcagaacaca atattgttgc agatgttgaa      960
gttgtgtcaa ttgaccatgt gaacgaagct ttagagcgtc ttgagaaggg tgatgttaga     1020
tacagatttg ttcttgatat tgggaatgca attgcctag                             1059
```

<210> SEQ ID NO 26
<211> LENGTH: 972
<212> TYPE: DNA
<213> ORGANISM: Amsonia hubrichtii
<220> FEATURE:
<221> NAME/KEY: misc_feature
<223> OTHER INFORMATION: REDOX 2 (reductase 2)

<400> SEQUENCE: 26

```
atggaaaagc aagtgaagat cccggagata gagttgaatt caggccacaa gatgccactg      60
gtgggcttcg ggacatgtgt gccggatccc attccaccat tagaggaact tgctgcaatc     120
tttttggaag ctattaaggt gggttatcgc cactttgaca cagcatcaag ctatggcaca     180
gaggaagccc tcggtaaagc tgttgctcaa gcaatagaga gtggcttggt caagggcaga     240
gaagagttat ttatcagttc taagttgtgg tgtgaagatg ctgatcatga tcttatcttg     300
cccgccctca agaaaacact tgggaatctg gagcttgatt atttggatct ttatatgatt     360
cacatgccag tgacagtgag gaagggtgct ccaatgttta attattcaaa agatgactta     420
ctccctttg atatacaagg acatggaaa gccatggaag agtgcagcaa attgggcttg     480
tctaagtcta ttggtgtaag caactacact tgtgaaaaac tctcaaaact gttcgaaaat     540
gccaccatcc cccagcagt caatcaggtg gaaatgaatg tttcatggca acagaggaaa     600
ttactgccat tttgcaaaga gaaaaacatc catgttacag catggtctcc tcttttgtct     660
tatggttccg cttggggcag taatgcagtg atggagaacc cagtccttgt aaatatcgca     720
gcttccaaaa gcaaaacggt ggcacaggtt gcactaagat ggatatacgg acaaggagca     780
agtttcatta tgaggacatt caacaaggaa aggatgttcc aaaatgttca gattttcgat     840
tgggaactct ctaagaaga attggatcaa attcaacaaa tccctcaacg tagaggcact     900
ctaggagaag attttatcaa tccagaggga ccaatcaagt cggtagagga actttgggat     960
ggagacttgt aa                                                        972
```

<210> SEQ ID NO 27
<211> LENGTH: 972
<212> TYPE: DNA
<213> ORGANISM: Tabernaemontana elegans
<220> FEATURE:
<221> NAME/KEY: misc_feature
<223> OTHER INFORMATION: REDOX 2 (reductase 2)

<400> SEQUENCE: 27

```
atggcaaagc aagttcgaat cccagaaata gagttgaact ctgggcacaa gatgccactg      60
gtgggcttcg ggacatgtgt gccagatccc ataccaccat tagaggaact tgtagcaatc     120
tttctcgagg ctatcaaggt tgggtatcgc cactttgaca cagcatcaag ttatggcaca     180
gaggaggccc ttggtaaagc tatggctcaa gcaatagagg gtggcttggt taagggcaga     240
gaggaattct tcatcagtga taaattgtgg tgtgaagatg ctgatcatga ccttatcttg     300
ccagccctca agaaaacact agggaatacg gggcttgatt atttggatct ttatatcata     360
catatgccag taagagtgag gcagggtgct ccaaggtaca attattcaaa agaagattta     420
ctccctttg atatacaagg acatggaag gccatggaag aatgcagcaa attgggcttg     480
gtcaggtcta ttggtgtaag caactacact tgtgaaaaac tcacagaact cttaggaaaa     540
gccaccattc ctcctgcagt taatcaggtg gagatgaacg ttgtttggca acagagaaaa     600
ttgctgccat tttgcaaaga gaaaaacatt catgtcacag catggtctcc tctattatct     660
tatggtgcca tctgggcag taatgcagtg atggagaatc cagtcctcgt agaaattgca     720
gcttccaaaa acaagaccgt agcacaggtt gcactaagat ggatatatga gcaaggagca     780
agtttcatca tgaggacctt taaaaaggag agaatgttcg aaaatgtaca gattttcgac     840
tgggaactca gtaaagaaga attggacaag attcaacaaa tccatcaacg tagggcact     900
```

```
ttgggagagg atttcatcca tccagagggg ccaattaaat ctgtggagga actctgggat    960
ggagatctgt aa                                                        972
```

<210> SEQ ID NO 28
<211> LENGTH: 972
<212> TYPE: DNA
<213> ORGANISM: Vinca minor
<220> FEATURE:
<221> NAME/KEY: misc_feature
<223> OTHER INFORMATION: REDOX 2 (reductase 2)

<400> SEQUENCE: 28

```
atgggaaaga aagtagaaat cccagaaata gagttgaatt caggggagaa gatgccgata     60
gtggggtatg gaacgtgcgt tccagatcca atcccaccat tagaagaact ttcaggaaca    120
tttttagagg caatgaaagc tgggtataga cactttgata ctgcttcaag ctatggcact    180
gaggaagctc ttggaaaagc tgtggctcaa gcaattgaca gcggtttggt taatgggaga    240
gatgaattct ttattagttg taagttgtgg tgtgaagatg ctgatgaaga acttatcttg    300
cctgctctca gaaatcact tggggatatg gggcttgatt atttggatct atatatgata    360
cacatgccag taagagtgag gaaaggtgct cccatgttca gctactcaaa agaggattta    420
ctcccatttg atatacaagg gacttggaag gccatggaag aatgctccaa acttgggttg    480
gctaaatcta ttggtgttag caactatact gttgaaaaac tcactaaact tctacaacat    540
tccaccatcc ccccagcagt taatcaggtg gagatgaatg ttgtttggca acagagaaaa    600
ttgatgccat tttgcaaaga gaaaaacatt catgtaacag catggtctcc tcttctatct    660
tatggtgttg cttggggcag taatgcagtt atggagaatc cagtccttct tgatattgca    720
gcttctaaag caagaccgt ggcacaggtt gcactaagat gggtatacga gcaaggagta    780
agtttcatat cgaggacctc caataaggag agaatgtacg aaaatgccca gatttttcgat    840 tgggaactca gtaaagaaga attggatcaa attcaaaaaa ttgcacaaca taagggcact    900
ttaggagaag aatttgttca tccagaggga ccaatcaaat cagtcgagga gctttgggac    960
ggagacttgt ga                                                        972
```

<210> SEQ ID NO 29
<211> LENGTH: 1266
<212> TYPE: DNA
<213> ORGANISM: Amsonia hubrichtii
<220> FEATURE:
<221> NAME/KEY: misc_feature
<223> OTHER INFORMATION: stemmadenine acetyltransferase (SAT)

<400> SEQUENCE: 29

```
atggcatcaa tccagatgga gatagtatca gaagagctga tcaaccatc atctcccaca     60 cccgaaagct aaaataccaa taaactgtcc ctcctagatc aagttttgtt gacatgtcat    120
attcctatta tcttcttcta cccaaatcag ttccactcaa acgtagatcc tgcccagaga    180
agtgaacacc tgaagcaatc tttgtcgaaa gtgttaacca agttctaccc tttagctgga    240
agaatcaatt tgaattcttc tgtagattgt aatgattctg gagttctgtt catcgaagct    300
cgagttcgag ctgaactctc gcaggcaatt cagaatgttg ctatagcgga actcaatcaa    360
tatcttccgt tcgaacctta tccccctgcg gaaagtgccg tgagaaagga tattcctcta    420
gctgtgaaag tcagtttctt tgaatgtgga ggcacagccg ttggtctctg catgtcacac    480
aagatagctg atatattgtc cgtggtcacc ttcttcaagg catggactgc acatgccaa     540 ggggaaactg atatcgttct gcctaatttt gacttggcat cccatcattt tccgcccatg    600
```

```
gacaatatcc cagcacctga atgggcacca gaagaaaaga ttttgatgaa aagattcgtg    660
ttcgataaag aaaaattagt agccctcaaa gcagaagctt cctcggcctc agaggtgaag    720
aatcccagtc gggtacaact cgtcacggct tttatatgga agcacatcat tgacgtaacc    780
cgatcgaaat ctgatcctaa aaataagttt tcagcaggtc aggcagtgaa cttgaggtca    840
agaatgagta ccccctttcc tccttctgct atggggaaca tcgccacact tgcattcgcc    900
gtcgcggagg aggacaagct agatttctgc gaccttgtag gtccgctaag aaccgcccta    960
gggaaaattg acgacgaaca tgttaaggaa ttacagaagg gagtgactta cttggatttt   1020
gaagctgaac cacaagaact gtcttctttc agcagttggt gtaggcttgg cttgtatgaa   1080
atggacttcg gctgggggaa gcctctctca gtgtgcactg caactctgcc catgaagaac   1140
atggtcttca tgatggatac aagatccggc gatggattag aagcctggat cagcatggca   1200
gaagatgaaa tggagatgct tccaagtcaa tttctttcac ttgtagatag tgattttagc   1260
aaatga                                                              1266

<210> SEQ ID NO 30
<211> LENGTH: 1263
<212> TYPE: DNA
<213> ORGANISM: Tabernaemontana elegans
<220> FEATURE:
<221> NAME/KEY: misc_feature
<223> OTHER INFORMATION: stemmadenine acetyltransferase (SAT)

<400> SEQUENCE: 30
atgacttccc agatggaggt agtatcagag gagctgattc aaccttcatc tccaacaccc     60
gaaagcttga acaccataa actttcactc ctagaccaag tgtcgttgac atgtcacatt    120
cctattattt tcttctaccc aaatcagtcg agcgactcaa atgtcgatcg tgcccaaaga    180
tctgagcacc tgaaacaatc tttgtccaaa gtgttaacta aattctatgt tttagcagga    240
agaatcaata taaattcttc cgtagattgt aatgattctg gagttctgtt catcgaagct    300
cgagttcaag ctgaactctc acaggcaatt cagaacgtcg ctatagagga attcaatcaa    360
tttcttccga tcgaacctta tcccggcggg cgaagcgagg tgaaaaagga tattcccta    420 gctgtgaaaa tcagtttctt tgactgtgga ggcacagccg ttggtgtctg cttatcacat    480
aagatagctg atatattgtc catggccacc ttcctcaatg cttggactgc acatgccga    540 ggggaaacac atattgtgct gcctaatttt gacttgggat ccatcatttt ccaccaatg    600 gacaacatcc cggcacctga atgggtaccg gatgaaaaga ttgtgatgaa aagatttgtt    660
tttgataaag aaaaattagc agccctcaaa gcacaagctt cctcagcctc agaggtgaag    720
aatcccagtc ggatagaagt tgttactgct tttatatgga agcacttcat tgacgtgacc    780
cgagcaaaat tttatactga aaacaagttt gccgccgctc aggcagtgaa cttgaggaca    840
agaatgagta caccccttcc tcagtctgct atggggaaca tcgccacgct tgcatttgca    900
gttgcagagg aggacaagga ttttcacgat cttgtaggtc cattaaggac tggcctgggg    960
aaaattgaca acgaacatgt taaggactta caaaagggac tgacttattt ggatgttgaa   1020
gcggaaccac aagaattgtc ttctttcagc agctggtgta ggcttggctt ttatgaaatg   1080
gactttggct ggggggaagcc tctttctgtg tgcactgcaa atttgcccat gaagaatacc   1140
gtatatatga tggatacaag atctggagag ggaatagaag catggattag catggcagaa   1200
gatgaaatgg cgatgcttcc tggcgaattt ctttcacttg ttgacagtga ttttagcaag   1260
tga                                                                 1263
```

<210> SEQ ID NO 31
<211> LENGTH: 1272
<212> TYPE: DNA
<213> ORGANISM: Vinca minor
<220> FEATURE:
<221> NAME/KEY: misc_feature
<223> OTHER INFORMATION: stemmadenine acetyltransferase (SAT)

<400> SEQUENCE: 31

```
atggcactcc aaatggagat agtatcagaa gagctaatta agccatcatc tccaacacct      60
caaaacttaa acaccacaa actttcccac ttagatcaag ttctattaac atgtcacatc     120
ccaattatcc tcttttatcc aaatcaatca acaaactcaa aatttcttga taatacccaa     180
aaatcccacc accttaaaca atctttatca caagttttaa cccaattcta cccttttagca    240
ggaagaatca ataaaaattc ctccatagat tgtaatgatt atggggtccc ttttcttgaa     300
tctaaagtcc aatcccaact ctcagatgca attcagaaca tcccagttaa agaactcagt     360
caatttcttc ctttccaacc ttatcccagt ggagataatg atgatcagga ggggtaaaa     420
aaggaaattc ctttagctgt gaaaatcaat ttctttgatt gtggaggaat agccattggt     480
gtctgcttat cacataagat agccgatgca ttatcgttgt ctactttttt gaaagcatgg     540
gctggaaaat ccagtgggga aattgatatt gtggtgccta attttgactt gggagcccat     600
cattttccgg ccatggataa cattccggcg ccggaattcg taccgaataa aaatattgtg    660
atggaaagat tgtgtttgg taaagaaaaa atacaagccc ttaaagaaca agcttcctct    720
gcatcagaga atccaagccg ggcccaagtt gttattgctt taatatggaa gcatttcatt    780
gatgtgacca agcaaaaac cggttccaca aacaaatttg tggcggccca agcagtgaat    840
ttgagatcaa gaatgagtcc acccttttcct gaatctgcca tgggcaacat tgccacgttg    900
gcatttgccg tggccgacga gggcagggat atttccgacc tcgtcggccc attgaaagac    960
agcataggaa aaattgatga gaacatgtt aaggaattac aaaagggagt gacttatttg   1020
gattatgaag ctgaaccaca agagttgttt tcttttagta gttggtgtag cttggttttt   1080
tatgagttgg attttgggtg gggtaagccc atttcagctt gtactacaac tgtgcccatg   1140
aagaatttgg tgtatttgat ggatacaaga aatggagatg gaattgaagc ttggattagt   1200
atggaagttg atgaaatggc tatgcttcca agtgattttc tttcacttgt ggatagtgat   1260
tttagcaagt ga                                                        1272
```

<210> SEQ ID NO 32
<211> LENGTH: 972
<212> TYPE: DNA
<213> ORGANISM: Amsonia hubrichtii
<220> FEATURE:
<221> NAME/KEY: misc_feature
<223> OTHER INFORMATION: HL2 (hydrolase 2)

<400> SEQUENCE: 32

```
atgggttctt taactgcaag ctcagatgag attattttcg atcttcctcc atacattaga     60
gtctataagg atgaaaggt agagagactt cattcctcac cgtatgttcc accatcactt    120
gatgatccag ccaccggtgt atcctggaaa gacgtcccaa tttcatcaga agtttcagct    180
agaatctacc taccaaagat cagcgaaaat gaaaaggaaa agctccccat cttggtctat    240
ttccatggtg caggcttctg tcttgaatcc gcctacaagt cattttttcca tacttatgtc    300
aaacactttg tggccgaagc caaagctatt gctgtttcgg ttgagttcag actcgcccct    360
```

```
gagcaccttt tacctgcagc ttatgaagat tgctggacgg cccttcagtg ggtggcttca    420
catgttggcc ttgacaactc cagcctcaag aatgctgttg ataaagagcc ttggataatc    480
aaccatggcg acttcgataa gctctactta tggggtgaca gtactggtgc aaatattgtg    540
cacaacgtac tcattagagc tggtaatgag aacttgcatg gcggggtgaa atcttgggt     600 gcaattcttt attacccata tttcctgatc cggaccagct ctaggcagag tgattatatg    660
gagaatgatt atagggagta ctggaagctg gcttatccat ctgccctgg tgggaatgat     720 aatccaatga taaaccctgt agctgagaat gctccagatt tagccggata tggatgttcg    780
aggctgctgg tatccatggt tgcggacgag gcaagagata taactctcct ctacattgag    840
gcattgaaga agagtgggtg gaaaggtgaa ctggacgtgg ctgatttcga aggagattac    900
tttgaaagcc cagaaacaga gatagccaag aacaggatca acgtttaac ctctttcatc     960 aacaaggagt aa                                                        972

<210> SEQ ID NO 33
<211> LENGTH: 972
<212> TYPE: DNA
<213> ORGANISM: Vinca minor
<220> FEATURE:
<221> NAME/KEY: misc_feature
<223> OTHER INFORMATION: HL2 (hydrolase 2)

<400> SEQUENCE: 33
atggctactt caactgaaac ctcagatgaa gtcctctttg aacttccacc atacatcaaa     60
atcttcaagg atggaagagt agaaagactc cattctaccc caaatgttcc accatcccct    120
aacgatccag aaaccggagt tcttggaaaa gacgtcccaa tttcatccca agtttcagca    180
agaatttacc ttccgaaaat ccccgaatcc gaaaataaaa agctcccgat tttagtctat    240
ttccacggag caggattctg tttagaatca gctttcaaag aattttacca cacttatgtc    300
aaacattttg tagccgaagc caaagcaatt gcaatttccg tcgagtttcg tctcgcaccg    360
gaacacaaat taccaacagc ttatgaagat tgctggactg gccttcaatg ggtttcttca    420
cattttggtc ttgacaattc tgccctcaag aattctattg ataaagaggc ttggattgtt    480
aaccacggag atttcagtag attgtatgtc tcgggtgata gtaccggggc taatattgtc    540
cataatgcac ttctaagagc tggtaaagag gaattgaatg gaggagtgaa atcttgggt     600 gggattctta attatccata tttccttgatt agtacaagtg agaaacagag tgattatatg    660
gagaatgagt acagagcata ctggaaattg gcttatcccg aggctcctgg cggggatgat    720
aatcccatga taaatccgac ggttgacaat gcacctgatt tagcaggata tggatgttcg    780
aggttgctgg tttcgatggt tgctgacgag gctagagaaa ttactctgct ttatattgag    840
gcattgaaga agagtggttg gaaaggtgaa ttggatgttg ctgattttga aggagattac    900
tttgaactct tcaatcttga aactgaggtt tctaagaaca aactcaggcg tttgacctct    960
tttgtcaagt ag                                                        972

<210> SEQ ID NO 34
<211> LENGTH: 978
<212> TYPE: DNA
<213> ORGANISM: Tabernaemontana elegans
<220> FEATURE:
<221> NAME/KEY: misc_feature
<223> OTHER INFORMATION: HL2 (hydrolase 2) homolog 1

<400> SEQUENCE: 34
atggcttctt caaccgaagg ctctgatgag attatttttg atcttcctcc atacattaga     60
```

```
gtctttaagg atggaagagt agagagactc cactcctcac catatgttcc accatcacaa    120
gatgatccct ccactggtgt atcctggaaa gacgtcccaa tttcatcaga ggtttcggct    180
aggatctacc tcccaaagat cagccaaaaa gaaaaggaaa agcttcccat tgtggtctat    240
ttccatggtg caggcttctg tctggaatca gccttcaaat cctttttcca cacttatgtc    300
aagcactttg cagccgaggc caaagcaatt gcggtttcgg ttgagttcag gctcgcccca    360
gagcaccact tgcctgcagc ttatgaagat tgctggactg cccttcagtg ggtggcttca    420
catgtagatg ttgacaactc cagcctcaaa aatgctattg ataaagagcc ttggataatc    480
aaccatggag atttggacaa gctctactta tggggtgaca gtacgggtgc caatattgtg    540
cacaacgtac tcatcagagc tggtaatgag agcttacatg gcggagtgaa atcctgggc    600 gcaattcttt attacccata tttcttgatc aggacaagct ccagacagag cgattacatg    660
gagaacgagt atagagcata ctggaagctg gcgtatccgt ctgctccagg tgggaacgac    720
aacccgatga taaaccccgt agctgagaac gctcctgatt tggccggata tggctgttcg    780
aggctgcttg tatccatggt cgcagacgag gccagagaca taacccttct ctacattgag    840
gcagtgaaga gagtgggtg gaagggtgaa ttggatgtgg ctgatttcga aggagattac    900
tttgaaatct tcagcccaga aactgagata ggcaagaaca aggtcacacg tttaacctct    960
ttcatcaaca aggagtaa                                                  978
```

<210> SEQ ID NO 35
<211> LENGTH: 978
<212> TYPE: DNA
<213> ORGANISM: Tabernaemontana elegans
<220> FEATURE:
<221> NAME/KEY: misc_feature
<223> OTHER INFORMATION: HL2 (Hydrolase 2) homolog 2

<400> SEQUENCE: 35

```
atgggttctt caactgaaag ctctgacgag attattttg atcttcctcc atacattaga    60
gtctttacgg atggaagagt agagagactc cactcctcac catatgttcc accgtcacta    120
gatgatcccg ccaccggtgt atcctggaaa gacgtcccaa tttcatcaga ggtttcggct    180
agaatctacc tcccaaagat cagccaaaag gataaggaaa agcttcccat tgtggtctat    240
ttccatggtg caggattctg tctggaatct gccttcaaat cctttttcca cacttatgtc    300
aagcactttg cagcggaggc caaagcaatt gcagtttcgg ttgagttcag gctcgcccca    360
gagcaccact tgcctgcagc ttatgaagat tgctggactg cccttcagtg ggtggcttca    420
catgcagatg ttgacaactc cagcctcaag aatgccattg ataaagagcc ttggataatc    480
aaccgtggag actttgacaa gctctattta tggggtgaca gtacgggtgc caatattgtg    540
cacaacgtac tcatcagagc tggtaatgag agcttacatg gcggagtgaa atcctgggc    600 gcaattcttt attacccata tttcttgatc aggacaagct ccagacagag cgattatatg    660
gagaacgagt atagagcata ctggaagctg gcttatccat ctgctcccgg gggcaacgac    720
aacccgatga taaaccccgt agctgagaac gctcctgatt tggccggata tggatgttcg    780
aggctgcttg tatccatggt cgcagacgag gccagagaca taacccttct ctacattgag    840
gcagtgaaga gagtgggtg gaagggtgaa ttggatgtgg ctgatttcga aggagattac    900
tttgaaatct tcagcccaga aactgagata ggcaagaaca aggtcacacg tttaacctct    960
ttcatcaaca aggagtaa                                                  978
```

<210> SEQ ID NO 36
<211> LENGTH: 1101
<212> TYPE: DNA
<213> ORGANISM: Tabernaemontana elegans
<220> FEATURE:
<221> NAME/KEY: misc_feature
<223> OTHER INFORMATION: HL2 (Hydrolase 2) homolog 3

<400> SEQUENCE: 36

```
atgtacacaa taaaaattta caaagtgagg ctacagtact cttatccaca tctacatcca      60
catctacata aacttgtaac accacaaaga gagacagaca atatcagaca gctgatagct     120
cttagattca tactggctat ggcttcagat gagattgcga ttgatatttc tccagacatc     180
atattgtata aagatggaaa ggtggtccga aattttgtcc aaccatatgt tccaccctca     240
cttgaagatc cgaccaccgg cgtatccact aaagacgtcc caatctcacc ggaagtttct     300
gctagagtct accttccaaa ggtcatcata gatggacaaa agctccctat cttggtctac     360
ttccatggtg gaggcttctg tcttgtatct gccttcgatt ctttgtataa cacttaccta     420
aagctcctgg tctccgaagc aacgcgatt gtagttacag tcgagttcag gctcactcct     480
gaataccctt tacctacagg ttatgaagat tgctggactg cccttcaatg ggtggcttca     540
cacgctgttt actactcaac caccggtgtt gacagagagc cttggctaat caactacggt     600
aactttgaca aactttacat aggtggtgac agtactggtg caacatggt gcataacata     660
gccatgagag ctggtcaaga aacttgcag ggtggtttga aaatcttagg tggaattctt     720
tcttatccat acttcttggt gagctcatgg gctaagaaaa atgaggaaac attgtctgac     780
atggtaaaaa tgtataagaa atattggttg ttgtcttatc catctgctcc aggtggctat     840
gagaatccct tggtaaatcc tgtagtggat gatgctccta gcttagccgg aatcggctgt     900
tcaagtttgc ttgtgattat ggctatcgac gatgtaagag aagctcatct tctttatgtt     960
gaggcattga ggaaaagcgg gtggaaaggt gaattggagt tggctgattt cgaaggatac    1020
gatcacttct ttgaagtctt taaccctact actcagagag ccaagaatat gatcaaacgc    1080
attgcctctt tcatcaagta g                                             1101
```

<210> SEQ ID NO 37
<211> LENGTH: 365
<212> TYPE: PRT
<213> ORGANISM: Amsonia hubrichtii
<220> FEATURE:
<221> NAME/KEY: MISC_FEATURE
<223> OTHER INFORMATION: GS Geissoschizine synthase

<400> SEQUENCE: 37

```
Met Ala Gly Glu Ser Thr Gln Leu Asp Leu Ser Val Lys Ala Ile Gly
1               5                   10                  15
Trp Gly Ala Lys Asp Ala Ser Gly Glu Leu His Ala Ile Lys Phe Ser
            20                  25                  30
Arg Arg Ala Pro Gly Glu Arg Asp Val Lys Ile Arg Val Leu Tyr Cys
        35                  40                  45
Gly Ile Cys Asn Phe Asp Met Glu Met Val Arg Asn Lys Trp Gly Phe
    50                  55                  60
Thr Arg Tyr Pro Tyr Val Phe Gly His Glu Thr Ala Gly Glu Val Val
65                  70                  75                  80
Glu Val Gly Ser Lys Val Gln Lys Phe Lys Val Gly Asp Lys Val Ala
                85                  90                  95
Val Gly Cys Met Val Gly Ser Cys Gly Lys Cys Tyr Asn Cys Glu Asn
            100                 105                 110
```

```
Gly Met Glu Asn Tyr Cys Pro Glu Pro Asn Met Ala Asp Gly Ser Val
            115                 120                 125

Tyr Arg Glu Gln Gly Glu Arg Ser Tyr Gly Gly Cys Ser Asn Val Met
130                 135                 140

Val Val Asp Glu Lys Phe Val Leu Arg Trp Pro Glu Asn Phe Pro Gln
145                 150                 155                 160

Asp Thr Gly Val Pro Leu Leu Cys Ala Gly Val Val Tyr Ser Pro
                165                 170                 175

Leu Lys His Val Gly Leu Asp Lys Pro Gly Met His Ile Gly Val Phe
                180                 185                 190

Gly Leu Gly Gly Leu Gly Ser Ile Ala Val Lys Tyr Ile Lys Ala Phe
            195                 200                 205

Gly Gly Lys Ala Thr Val Ile Ser Thr Ser Lys Arg Lys Glu Lys Glu
            210                 215                 220

Ala Ile Glu Glu His Gly Ala Asp Ala Phe Val Val Asn Ser Asp Thr
225                 230                 235                 240

Glu Gln Leu Gln Ala Leu Thr Gly Thr Met Asp Gly Val Ile Asp Thr
                245                 250                 255

Thr Pro Gly Gly Arg Thr Pro Met Ala Leu Met Leu Asn Leu Leu Lys
            260                 265                 270

Phe Asp Gly Thr Val Ile Leu Val Gly Ala Pro Glu Thr Leu Phe Glu
            275                 280                 285

Leu Pro Val Gln Pro Leu Ile Leu Gly Arg Arg Lys Val Ile Gly Ser
            290                 295                 300

Ser Thr Gly Gly Leu Arg Glu Tyr Gln Glu Met Leu Asp Phe Ser Ala
305                 310                 315                 320

Lys His Asn Ile Leu Cys Asp Thr Glu Val Ile Pro Ile Asp Tyr Leu
                325                 330                 335

Ser Thr Ala Met Glu Arg Ile Lys Asn Leu Asp Val Lys Tyr Arg Phe
                340                 345                 350

Val Ile Asp Ile Gly Asn Thr Leu Lys Tyr Asp Glu Glu
                355                 360                 365

<210> SEQ ID NO 38
<211> LENGTH: 354
<212> TYPE: PRT
<213> ORGANISM: Tabernaemontana elegans
<220> FEATURE:
<221> NAME/KEY: MISC_FEATURE
<223> OTHER INFORMATION: GS Geissoschizine synthase

<400> SEQUENCE: 38

Ser Val Lys Ala Val Gly Trp Gly Ala Ala Asp Ala Ser Gly Thr Leu
1               5                   10                  15

Gln Pro Ile Lys Phe Phe Arg Arg Val Pro Gly Glu Arg Asp Val Lys
                20                  25                  30

Ile Arg Val Leu Tyr Cys Gly Val Cys Asn Phe Asp Met Glu Met Val
            35                  40                  45

Arg Asn Lys Trp Gly Phe Thr Arg Tyr Pro Tyr Val Phe Gly His Glu
50                  55                  60

Thr Ala Gly Glu Val Val Glu Val Gly Ser Lys Val Gly Lys Phe Lys
65                  70                  75                  80

Val Gly Asp Lys Val Ala Val Gly Cys Met Val Gly Ser Cys Gly Lys
                85                  90                  95

Cys Leu Asn Cys Glu Thr Gly Phe Glu Asn Tyr Cys Pro Glu Pro Asn
```

```
                100                 105                 110
Met Ala Asp Gly Ser Val Tyr Arg Glu Gln Gly Glu Arg Ser Tyr Gly
                115                 120                 125

Gly Cys Ser Asn Val Met Val Asp Glu Lys Phe Val Leu Arg Trp
            130                 135                 140

Pro Glu Asn Tyr Pro Gln Asp Thr Gly Val Pro Ile Leu Cys Ala Gly
145                 150                 155                 160

Ile Val Val Tyr Ser Pro Leu Lys His Met Gly Leu Asp Lys Pro Gly
                165                 170                 175

Lys His Ile Gly Val Phe Gly Phe Gly Gly Ile Gly Ala Met Ala Val
                180                 185                 190

Lys Phe Ile Lys Ala Phe Gly Gly Lys Ala Thr Val Ile Ser Thr Ser
            195                 200                 205

Lys Arg Lys Glu Lys Glu Ala Ile Glu Glu His Gly Ala Asp Asp Phe
        210                 215                 220

Val Val Asn Thr Asp Thr Glu Lys Leu Gln Ala Leu Ala Gly Thr Met
225                 230                 235                 240

Asp Gly Val Val Asp Thr Thr Pro Gly Gly Arg Thr Pro Met Ser Leu
                245                 250                 255

Met Leu Asn Leu Leu Lys Phe Asp Gly Ala Val Leu Leu Val Gly Ala
                260                 265                 270

Pro Glu Thr Leu Phe Glu Leu Pro Val Gln Pro Leu Ile Leu Gly Arg
            275                 280                 285

Arg Lys Ile Ile Gly Ser Ser Thr Gly Gly Leu Lys Glu Tyr Gln Ala
        290                 295                 300

Met Leu Asp Phe Ala Ala Gln His Asn Ile Ile Cys Asp Thr Glu Val
305                 310                 315                 320

Ile Gly Ile Asp Tyr Leu Glu Thr Ala Met Glu His Ile Arg Asn Leu
                325                 330                 335

Asp Val Lys Tyr Arg Phe Ser Ile Asp Ile Gly Asn Thr Leu Lys Phe
                340                 345                 350

Glu Glu

<210> SEQ ID NO 39
<211> LENGTH: 364
<212> TYPE: PRT
<213> ORGANISM: Vinca minor
<220> FEATURE:
<221> NAME/KEY: MISC_FEATURE
<223> OTHER INFORMATION: GS Geissoschizine synthase

<400> SEQUENCE: 39

Met Ala Ala Glu Thr Thr Gln Leu Asp Leu Ser Val Lys Ala Val Gly
1               5                   10                  15

Trp Gly Ala Ala Asp Ala Ser Gly Thr Leu Gln Pro Ile Lys Phe Phe
                20                  25                  30

Arg Arg Val Pro Gly Glu Arg Asp Val Lys Ile Arg Val Leu Tyr Cys
            35                  40                  45

Gly Val Cys Asn Phe Asp Met Glu Met Val Arg Asn Lys Trp Gly Phe
        50                  55                  60

Thr Arg Tyr Pro Tyr Val Phe Gly His Glu Thr Ala Gly Glu Val Val
65                  70                  75                  80

Glu Val Gly Ser Lys Val Gly Lys Phe Lys Val Gly Asp Lys Val Ala
                85                  90                  95

Val Gly Cys Met Val Gly Ser Cys Gly Lys Cys Leu Asn Cys Glu Thr
```

100                 105                 110
Gly Phe Glu Asn Tyr Cys Pro Glu Pro Asn Met Ala Asp Gly Ser Val
            115                 120                 125

Tyr Arg Glu Gln Gly Glu Arg Ser Tyr Gly Gly Cys Ser Asn Val Met
130                 135                 140

Val Val Asp Glu Lys Phe Val Leu Arg Trp Pro Glu Asn Tyr Pro Gln
145                 150                 155                 160

Asp Thr Gly Val Pro Ile Leu Cys Ala Gly Ile Val Val Tyr Ser Pro
                165                 170                 175

Leu Lys His Met Gly Leu Asp Lys Pro Gly Lys His Ile Gly Val Phe
            180                 185                 190

Gly Phe Gly Gly Ile Gly Ala Met Ala Val Lys Phe Ile Lys Ala Phe
        195                 200                 205

Gly Gly Lys Ala Thr Val Ile Ser Thr Ser Lys Arg Lys Glu Lys Glu
    210                 215                 220

Ala Ile Glu Glu His Gly Ala Asp Asp Phe Val Val Asn Thr Asp Thr
225                 230                 235                 240

Glu Lys Leu Gln Ala Leu Ala Gly Thr Met Asp Gly Val Val Asp Thr
                245                 250                 255

Thr Pro Gly Gly Arg Thr Pro Met Ala Leu Met Leu Ser Leu Leu Lys
            260                 265                 270

Phe Asp Gly Ser Val Ile Leu Val Gly Ala Pro Glu Cys Leu Phe Glu
        275                 280                 285

Leu Pro Val Gln Pro Leu Ile Val Gly Arg Arg Lys Ile Ile Gly Ser
    290                 295                 300

Ser Thr Gly Gly Leu Lys Glu Tyr Gln Asp Met Leu Asp Phe Ala Ala
305                 310                 315                 320

Gln His Lys Ile Met Cys Asp Thr Glu Val Ile Gly Ile Asp Tyr Leu
                325                 330                 335

Asp Thr Ala Met Glu Arg Ile Arg Asn Leu Asp Val Lys Tyr Arg Phe
            340                 345                 350

Ser Ile Asp Ile Gly Asn Thr Leu Lys Phe Glu Glu
        355                 360

<210> SEQ ID NO 40
<211> LENGTH: 501
<212> TYPE: PRT
<213> ORGANISM: Amsonia hubrichtii
<220> FEATURE:
<221> NAME/KEY: MISC_FEATURE
<223> OTHER INFORMATION: GO (Geissoschizine Oxidase)

<400> SEQUENCE: 40

Met Glu Phe Ser Phe Ser Ser Pro Leu Leu Tyr Ile Val Tyr Phe Leu
1               5                   10                  15

Leu Phe Phe Leu Val Arg Tyr Leu Leu Lys Pro Lys Ser Asn Lys Lys
            20                  25                  30

Leu Pro Pro Gly Pro Arg Thr Leu Pro Ile Ile Gly Asn Leu His Gln
        35                  40                  45

Leu Met Gly Pro Leu Pro His Arg Thr Leu Lys Glu Leu Ser Asp Arg
    50                  55                  60

His Gly Pro Leu Met His Val Lys Met Gly Glu Arg Ser Ala Ile Ile
65                  70                  75                  80

Val Ser Asn Ala Arg Met Ala Lys Ile Val Leu His Asn His Gly Leu
                85                  90                  95

```
Ala Val Ala Asp Arg Ser Val Asn Thr Val Ala Ser Ile Met Thr Tyr
            100                 105                 110

Asn Ser Leu Gly Val Thr Phe Ala Gln Tyr Gly Asp Tyr Leu Thr Lys
        115                 120                 125

Leu Arg Gln Ile Tyr Thr Leu Glu Leu Leu Ser Pro Lys Lys Val Arg
    130                 135                 140

Ser Phe Tyr Gly Cys Phe Glu Glu Leu Asp Val Phe Val Glu Ser
145                 150                 155                 160

Ile Lys Ser Ser Val Gly Gln Pro Met Val Met Tyr Glu Lys Cys Ser
                165                 170                 175

Lys Tyr Leu Tyr Ala Thr Ile Cys Arg Thr Ile Phe Gly Ser Val Cys
            180                 185                 190

Lys Glu Arg Glu Lys Met Ile Lys Ile Val Lys Lys Thr Ser Leu Leu
        195                 200                 205

Ser Gly Thr Pro Leu Arg Leu Glu Asp Leu Phe Pro Ser Met Ser Val
    210                 215                 220

Phe Ala Arg Phe Ser Lys Thr Leu Lys Gln Leu Arg Gly Leu Leu Gln
225                 230                 235                 240

Glu Met Asp Asp Ile Leu Glu Asp Ile Ile Thr Glu Arg Glu Lys Thr
                245                 250                 255

Thr Glu Ile Ser Thr Glu Ser Lys Asp Asp Glu Asp Met Leu Ser Val
            260                 265                 270

Leu Leu Arg His Lys Trp His Asn Pro Ser Gly Ala Lys Phe Arg Ile
        275                 280                 285

Thr Asn Ala Asp Ile Lys Ala Ile Ile Phe Glu Leu Ile Leu Ala Ala
    290                 295                 300

Thr Leu Ser Val Ala Asp Val Ala Glu Trp Ala Met Val Glu Ile Leu
305                 310                 315                 320

Arg Asp Pro Lys Ser Leu Lys Lys Val Tyr Glu Val Arg Glu Val
                325                 330                 335

Cys Lys Glu Lys Lys Val Thr Gly His Asp Val Glu Lys Leu Glu
            340                 345                 350

Phe Met Arg Leu Cys Leu Lys Glu Ser Thr Arg Ile His Pro Ala Ala
        355                 360                 365

Pro Leu Leu Val Pro Arg Glu Cys Arg Glu Asp Phe Glu Val Asp Gly
    370                 375                 380

Tyr Thr Val Pro Lys Gly Ala Trp Val Leu Thr Asn Cys Trp Ala Val
385                 390                 395                 400

Gln Met Asp Pro Glu Val Trp Pro Glu Pro Glu Lys Phe Asp Pro Glu
                405                 410                 415

Arg Tyr Ile Arg Asn Pro Met Asp Phe Tyr Gly Ser Ser Phe Glu Leu
            420                 425                 430

Ile Pro Phe Gly Thr Gly Arg Arg Gly Cys Pro Gly Ile Leu Tyr Gly
        435                 440                 445

Val Thr Asn Ala Glu Leu Met Leu Ala Ala Met Phe Tyr His Phe Asp
    450                 455                 460

Trp Glu Ile Ala Asp Gly Lys Lys Pro Glu Glu Ile Asp Met Thr Glu
465                 470                 475                 480

Asp Phe Gly Ala Gly Cys Ile Met Lys Tyr Pro Leu Lys Leu Val Pro
                485                 490                 495

His Leu Ala Lys Asn
            500
```

<210> SEQ ID NO 41
<211> LENGTH: 505
<212> TYPE: PRT
<213> ORGANISM: Tabernaemontana elegans
<220> FEATURE:
<221> NAME/KEY: MISC_FEATURE
<223> OTHER INFORMATION: GO (Geissoschizine Oxidase)

<400> SEQUENCE: 41

```
Met Arg Arg Arg Trp Arg Leu Lys Asp Asp Phe Pro Ala Leu Tyr Ile
1               5                   10                  15

Leu Tyr Phe Leu Leu Phe Leu Leu Val Lys Gln Leu Leu Lys Pro Lys
            20                  25                  30

Ser Gln Lys Lys Leu Pro Pro Gly Pro Arg Thr Leu Pro Ile Ile Gly
        35                  40                  45

Asn Leu His Gln Leu Met Gly Pro Leu Pro His Arg Thr Leu Lys Asp
    50                  55                  60

Leu Ser Asp Lys His Gly Pro Leu Met His Leu Lys Met Gly Glu Arg
65                  70                  75                  80

Ser Ala Ile Ile Val Ser Asp Ala Arg Met Ala Lys Ile Val Leu His
                85                  90                  95

Asn His Gly Leu Ala Val Ala Asp Arg Ser Val Asn Thr Val Ala Ser
            100                 105                 110

Ile Met Thr Tyr Asn Ser Leu Gly Val Thr Phe Ala Gln Tyr Gly Asp
        115                 120                 125

Tyr Leu Thr Lys Leu Arg Gln Ile Tyr Thr Leu Glu Leu Leu Ser Pro
    130                 135                 140

Lys Lys Val Arg Ser Phe Tyr Ser Cys Phe Glu Asp Glu Leu Asp Gly
145                 150                 155                 160

Phe Val Lys Ser Ile Lys Ser Gln Val Gly Gln Pro Met Val Leu Tyr
                165                 170                 175

Glu Lys Ala Ser Thr Tyr Leu Tyr Ala Thr Ile Cys Arg Thr Ile Phe
            180                 185                 190

Gly Ser Ile Cys Lys Glu Arg Glu Lys Met Ile Lys Ile Val Lys Arg
        195                 200                 205

Thr Ser Leu Leu Ser Gly Thr Pro Leu Arg Leu Glu Asp Leu Phe Pro
    210                 215                 220

Ser Met Arg Val Phe Cys Arg Phe Ser Lys Thr Leu Asn Gln Leu Arg
225                 230                 235                 240

Gly Leu Leu Gln Glu Met Asp Asp Ile Leu Glu Asp Ile Ile Glu
                245                 250                 255

Arg Glu Lys Thr Thr Glu Ile Ser Thr Glu Ala Lys Asp Asp Glu Asp
            260                 265                 270

Met Leu Ser Val Leu Leu Arg His Lys Trp His Asn Pro Ser Gly Ala
        275                 280                 285

Lys Phe Arg Ile Thr Asn Ala Asp Ile Lys Ala Ile Phe Glu Leu
    290                 295                 300

Ile Leu Ala Ala Thr Leu Ser Val Ala Asp Val Thr Glu Trp Ala Met
305                 310                 315                 320

Val Glu Ile Leu Arg Asp Pro Lys Ser Leu Lys Lys Val Tyr Asp Glu
                325                 330                 335

Val Arg Glu Val Cys Lys Glu Lys Arg Val Thr Gly Tyr Asp Val
            340                 345                 350

Glu Lys Leu Glu Tyr Met His Leu Cys Val Lys Glu Ser Thr Arg Ile
        355                 360                 365
```

```
His Pro Ala Ala Pro Leu Leu Val Pro Arg Glu Cys Arg Glu Asp Phe
    370                 375                 380

Glu Val Asp Gly Tyr Thr Val Pro Lys Gly Ala Trp Val Leu Thr Asn
385                 390                 395                 400

Cys Trp Ala Val Gln Met Asp Pro Lys Ile Trp Pro Glu Pro Glu Lys
                405                 410                 415

Phe Asp Pro Glu Arg Tyr Ile Arg Asn Pro Met Asp Phe Tyr Gly Ser
            420                 425                 430

Asn Phe Glu Leu Ile Pro Phe Gly Thr Gly Arg Arg Gly Cys Pro Gly
        435                 440                 445

Ile Leu Phe Gly Val Thr Asn Ala Glu Leu Leu Ala Ala Met Phe
450                 455                 460

Tyr His Phe Asp Trp Glu Ile Ala Asp Gly Lys Lys Pro Glu Glu Ile
465                 470                 475                 480

Asp Leu Thr Glu Asp Phe Gly Ala Gly Cys Ile Met Lys Tyr Pro Leu
                485                 490                 495

Lys Leu Val Pro His Leu Val Asn Glu
            500                 505

<210> SEQ ID NO 42
<211> LENGTH: 429
<212> TYPE: PRT
<213> ORGANISM: Vinca minor
<220> FEATURE:
<221> NAME/KEY: MISC_FEATURE
<223> OTHER INFORMATION: GO (Geissoschizine Oxidase)

<400> SEQUENCE: 42

Met Glu Phe Ser Phe Ser Ser Leu Pro Leu Tyr Ile Ala Ser Phe Leu
1               5                   10                  15

Leu Phe Phe Leu Val Lys Gln Ile Leu Lys Pro Lys Ser Gly Lys Lys
            20                  25                  30

Leu Pro Pro Gly Pro Arg Thr Leu Pro Ile Ile Gly Asn Leu His Gln
        35                  40                  45

Leu Met Gly Pro Leu Pro His Arg Thr Leu Lys Asn Leu Ser Asp Lys
    50                  55                  60

His Gly Pro Leu Met His Leu Lys Leu Gly Glu Arg Ser Ala Ile Ile
65                  70                  75                  80

Val Ser Asp Ala Arg Leu Ala Lys Ile Val Leu His Asn Asn Gly Leu
                85                  90                  95

Ala Val Ala Asp Arg Ser Val Asn Thr Val Ala Ser Ile Met Thr Tyr
            100                 105                 110

Asn Ser Leu Gly Val Thr Phe Ala Gln Tyr Gly Asp Tyr Leu Thr Lys
        115                 120                 125

Leu Arg Gln Ile Tyr Thr Leu Glu Leu Leu Ser Gln Lys Lys Val Arg
    130                 135                 140

Ser Phe Tyr Asn Cys Phe Glu Asp Glu Leu Asp Thr Phe Val Lys Ser
145                 150                 155                 160

Ile Lys Ser Ser Asn Gly Gln Pro Met Val Leu Tyr Glu Val Ala Ser
                165                 170                 175

Thr Tyr Leu Tyr Ala Thr Ile Cys Arg Thr Ile Phe Gly Ser Val Cys
            180                 185                 190

Lys Glu Arg Glu Lys Met Ile Lys Ile Val Lys Arg Thr Ser Leu Leu
        195                 200                 205

Ser Gly Thr Pro Leu Arg Leu Glu Asp Leu Phe Pro Ser Met Ser Val
    210                 215                 220
```

```
Phe Cys Arg Phe Ser Lys Thr Leu Asn Gln Leu Arg Gly Leu Leu Asp
225                 230                 235                 240

Glu Met Asp His Ile Leu Glu Asp Ile Ile Val Asp Arg Glu Lys Asn
                245                 250                 255

Thr Glu Ile Leu Lys Glu Gly Lys Asp Asp Glu Asp Met Leu Ser Val
                260                 265                 270

Leu Leu Arg His Lys Trp His Asn Pro Ser Gly Ala Lys Phe Arg Ile
                275                 280                 285

Ala Asn Ala Asp Ile Lys Ala Ile Ile Phe Glu Leu Ile Leu Ala Ala
                290                 295                 300

Thr Leu Ser Val Ala Asp Val Thr Glu Trp Ala Met Val Glu Ile Ile
305                 310                 315                 320

Arg Asp Pro Lys Ser Leu Lys Lys Val His Glu Glu Val Arg Gln Val
                325                 330                 335

Cys Lys Asp Lys Gly Lys Val Thr Gly Tyr Asp Val Glu Lys Leu Asp
                340                 345                 350

Tyr Leu Arg Leu Cys Leu Lys Glu Ser Thr Arg Ile His Pro Ala Ala
                355                 360                 365

Pro Leu Leu Val Pro Arg Glu Cys Arg Glu Asp Phe Gln Val Asp Gly
                370                 375                 380

Phe Thr Val Pro Lys Gly Ala Trp Val Leu Thr Asn Cys Trp Ala Val
385                 390                 395                 400

Gln Met Asp Pro Glu Val Trp Pro Glu Pro Glu Lys Phe Asp Pro Glu
                405                 410                 415

Arg Tyr Ile Arg Lys Pro Met Asp Phe Tyr Gly Asn Ser
                420                 425

<210> SEQ ID NO 43
<211> LENGTH: 413
<212> TYPE: PRT
<213> ORGANISM: Amsonia hubrichtii
<220> FEATURE:
<221> NAME/KEY: MISC_FEATURE
<223> OTHER INFORMATION: REDOX 1 (reductase 1)

<400> SEQUENCE: 43

Met Lys Asn Leu Leu Pro Asn Arg Leu Asn Arg Asn Lys Lys Asn Trp
1               5                   10                  15

Ile Asn Lys His Lys Ser Thr Thr Leu Arg Glu Met Arg Glu Leu Lys
                20                  25                  30

Ala Ser Glu Ile Ile Trp Glu Gln Asn Leu Ala Arg Lys Tyr Ser Ser
            35                  40                  45

Arg Tyr Ser Gly Thr Gly Thr Leu Leu Glu Lys Met Ala Asp Arg Met
        50                  55                  60

Lys Thr Ile Gly Trp Ala Ala His Asp Ser Ser Gly Ile Leu Ser Pro
65              70                  75                  80

Phe Glu Phe Thr Arg Arg Ala Thr Gly Glu Glu Asp Val Arg Leu Lys
                85                  90                  95

Val Leu Tyr Cys Gly Ile Cys His Ser Asp Leu His Asn Ile Lys Asn
                100                 105                 110

Glu Met Gly Phe Thr Ser Tyr Pro Cys Val Pro Gly His Glu Val Val
                115                 120                 125

Gly Glu Val Thr Glu Val Gly Ser Lys Val Lys Phe Lys Ala Gly
                130                 135                 140

Asp Lys Val Gly Val Gly Leu Phe Val Asp Ser Cys Arg Glu Cys Glu
```

```
                145                 150                 155                 160
Gln Cys Ala Asn Asp Leu Glu Pro Tyr Cys Pro Lys Leu Lys Leu Ala
                    165                 170                 175
Tyr Leu Ser Leu Asp Asp Gly Thr Val Ile Gln Gly Gly Tyr Ser
                180                 185                 190
Asn Glu Met Val Val Lys Glu His Tyr Val Asn Arg Trp Pro Glu Thr
                    195                 200                 205
Leu Pro Leu Asp Ala Gly Ala Pro Leu Ile Gly Ala Gly Ser Thr Val
210                 215                 220
Tyr Ser Pro Met Lys Tyr Tyr Gly Leu Asp Lys Pro Gly Gln His Leu
225                 230                 235                 240
Gly Val Val Gly Leu Gly Gly Leu Gly His Leu Ala Val Lys Phe Ala
                    245                 250                 255
Lys Ala Phe Gly Leu Lys Val Thr Val Ile Ser Thr Ser Pro Arg Lys
                260                 265                 270
Lys Glu Glu Ala Leu Asn His Leu Gly Ala Asp Ser Phe Leu Val Ser
                275                 280                 285
Thr Asp Gln Glu Gln Met Gln Lys Ala Met Ser Thr Leu Asp Gly Ile
                290                 295                 300
Ile Asp Thr Val Ser Ala Pro His Ala Val Met Pro Leu Phe Phe Leu
305                 310                 315                 320
Leu Lys Pro His Gly Lys Leu Ile Val Val Gly Ala Pro Asn Lys Pro
                    325                 330                 335
Leu Glu Val Asp Val Pro Phe Leu Leu Met Gly Arg Lys Met Leu Gly
                340                 345                 350
Ala Ser Ala Val Gly Gly Met Lys Glu Thr Gln Glu Met Leu Asp Phe
                355                 360                 365
Ala Ala Lys His Asp Ile Thr Ala Asp Val Glu Val Pro Met Asp
                370                 375                 380
Tyr Val Asn Lys Ala Met Glu Arg Leu Glu Lys Gly Asp Val Lys Tyr
385                 390                 395                 400
Arg Phe Val Leu Asp Ile Gly Asn Thr Leu Leu Ala Ala
                    405                 410

<210> SEQ ID NO 44
<211> LENGTH: 354
<212> TYPE: PRT
<213> ORGANISM: Tabernaemontana elegans
<220> FEATURE:
<221> NAME/KEY: MISC_FEATURE
<223> OTHER INFORMATION: REDOX 1 (reductase 1)

<400> SEQUENCE: 44

Met Ala Asp Arg Val Lys Thr Ile Gly Trp Ala Ala His Asp Ser Ser
1               5                   10                  15
Gly Ile Leu Ser Pro Phe Glu Phe Thr Arg Arg Ala Thr Gly Asn Glu
                20                  25                  30
Asp Val Arg Phe Lys Val Leu Tyr Cys Gly Ile Cys His Ser Asp Leu
                35                  40                  45
His Asn Val Lys Asn Glu Met Gly Phe Thr Ser Tyr Pro Cys Val Pro
            50                  55                  60
Gly His Glu Val Val Gly Glu Val Thr Glu Val Gly Ser Lys Val Lys
65                  70                  75                  80
Lys Phe Lys Ala Gly Asp Lys Val Gly Val Gly Leu Phe Val Asp Ser
                85                  90                  95
```

Cys Arg Glu Cys Glu Gln Cys Lys Asn Asp Leu Glu Pro Tyr Cys Pro
            100                 105                 110

Lys Leu Lys Met Ala Tyr Leu Ser Pro Asp Asp Gly Thr Ile Ile
        115                 120                 125

Gln Gly Gly Tyr Ser Asn Glu Met Val Val Lys Glu His Tyr Val Leu
            130                 135                 140

Arg Trp Pro Glu Thr Leu Pro Leu Asp Ala Gly Ala Pro Leu Val Gly
145                 150                 155                 160

Ala Gly Ser Thr Val Tyr Ser Pro Met Lys Tyr Tyr Gly Leu Asp Lys
                165                 170                 175

Pro Gly Gln His Leu Gly Val Val Gly Leu Gly Gly Leu Gly His Leu
            180                 185                 190

Ala Val Lys Phe Ala Lys Ala Phe Gly Leu Lys Val Thr Val Ile Ser
            195                 200                 205

Thr Ser Pro Arg Lys Lys Glu Glu Ala Ile Thr His Leu Gly Ala Asp
        210                 215                 220

Ser Phe Leu Val Ser Thr Asp Gln Glu Gln Met Gln Lys Ala Thr Ser
225                 230                 235                 240

Thr Leu Asp Gly Ile Ile Asp Thr Val Ser Ala Pro His Ala Val Met
                245                 250                 255

Pro Leu Phe Phe Leu Leu Lys Pro His Gly Lys Leu Ile Val Val Gly
            260                 265                 270

Ala Pro Asn Lys Pro Leu Glu Val Asp Val Pro Phe Leu Leu Met Gly
        275                 280                 285

Arg Lys Met Leu Gly Ala Ser Ala Val Gly Gly Met Lys Glu Thr Gln
290                 295                 300

Glu Met Leu Asp Phe Ala Ala Glu His Asn Ile Thr Ala Asp Ile Glu
305                 310                 315                 320

Val Val Pro Met Asp Tyr Val Asn Lys Ala Leu Glu Arg Leu Glu Lys
                325                 330                 335

Gly Asp Val Arg Tyr Arg Phe Val Leu Asp Ile Gly Asn Thr Met Ala
            340                 345                 350

Ala Ala

<210> SEQ ID NO 45
<211> LENGTH: 352
<212> TYPE: PRT
<213> ORGANISM: Vinca minor
<220> FEATURE:
<221> NAME/KEY: MISC_FEATURE
<223> OTHER INFORMATION: REDOX 1 (reductase 1)

<400> SEQUENCE: 45

Met Thr Gly Arg Val Lys Thr Ile Gly Trp Ala Ala His Asp Lys Ser
1               5                   10                  15

Gly Val Leu Ser Pro Phe Glu Phe Thr Arg Arg Ala Thr Gly Asp Glu
            20                  25                  30

Asp Val Arg Leu Lys Val Leu Tyr Cys Gly Val Cys His Ser Asp Leu
        35                  40                  45

His Ile Ile Lys Asn Glu Met Glu Phe Thr Ser Tyr Pro Cys Val Pro
    50                  55                  60

Gly His Glu Val Val Gly Glu Val Thr Glu Thr Gly Arg Lys Val Glu
65                  70                  75                  80

Lys Phe Lys Val Gly Asp Lys Val Gly Val Gly Leu Phe Val Glu Ser
                85                  90                  95

Cys Arg Glu Cys Glu Gln Cys Thr Asn Asp Leu Glu Pro Tyr Cys Pro
            100                 105                 110

Lys Met Lys Met Thr Tyr Leu Ser Leu Asp Asp Gly Ile Val Asn
    115                 120                 125

Gln Gly Gly Tyr Ser Lys Glu Met Val Val Lys Glu Pro Phe Val Phe
130                 135                 140

Arg Trp Pro Glu Thr Leu Pro Leu Ala Ala Gly Ala Pro Leu Leu Gly
145                 150                 155                 160

Ala Gly Ser Thr Val Tyr Ser Pro Met Lys Tyr Glu Leu Asp Lys
            165                 170                 175

Pro Gly Gln His Leu Gly Val Val Gly Leu Gly Gly Leu Gly His Leu
            180                 185                 190

Ala Val Lys Phe Ala Lys Ala Leu Gly Leu Lys Val Thr Val Ile Ser
            195                 200                 205

Thr Ser Pro Ser Lys Lys Glu Glu Ala Ile Lys Asn Leu Gly Ala Asp
            210                 215                 220

Ala Phe Leu Val Ser Thr Asp Gln Glu Gln Met Gln Lys Ala Met Ser
225                 230                 235                 240

Thr Met Asp Gly Ile Ile Asp Thr Val Ser Ala Ser His Ala Ala Met
            245                 250                 255

Pro Leu Ile Phe Leu Leu Lys Pro His Gly Lys Leu Ile Val Val Gly
            260                 265                 270

Ala Pro Asn Lys Pro Leu Gln Leu Asp Ile Pro Phe Leu Val Met Gly
            275                 280                 285

Arg Lys Met Leu Gly Thr Ser Ala Val Gly Gly Met Lys Glu Thr Gln
290                 295                 300

Glu Met Leu Asp Phe Ala Ala Glu His Asn Ile Val Ala Asp Val Glu
305                 310                 315                 320

Val Val Ser Ile Asp His Val Asn Glu Ala Leu Glu Arg Leu Glu Lys
            325                 330                 335

Gly Asp Val Arg Tyr Arg Phe Val Leu Asp Ile Gly Asn Ala Ile Ala
            340                 345                 350

<210> SEQ ID NO 46
<211> LENGTH: 323
<212> TYPE: PRT
<213> ORGANISM: Amsonia hubrichtii
<220> FEATURE:
<221> NAME/KEY: MISC_FEATURE
<223> OTHER INFORMATION: REDOX 2 (reductase 2)

<400> SEQUENCE: 46

Met Glu Lys Gln Val Lys Ile Pro Glu Ile Glu Leu Asn Ser Gly His
1               5                   10                  15

Lys Met Pro Leu Val Gly Phe Gly Thr Cys Val Pro Asp Pro Ile Pro
            20                  25                  30

Pro Leu Glu Glu Leu Ala Ala Ile Phe Leu Glu Ala Ile Lys Val Gly
            35                  40                  45

Tyr Arg His Phe Asp Thr Ala Ser Ser Tyr Gly Thr Glu Glu Ala Leu
    50                  55                  60

Gly Lys Ala Val Ala Gln Ala Ile Glu Ser Gly Leu Val Lys Gly Arg
65                  70                  75                  80

Glu Glu Leu Phe Ile Ser Ser Lys Leu Trp Cys Glu Asp Ala Asp His
                85                  90                  95

Asp Leu Ile Leu Pro Ala Leu Lys Lys Thr Leu Gly Asn Leu Glu Leu
            100                 105                 110

```
Asp Tyr Leu Asp Leu Tyr Met Ile His Met Pro Val Thr Val Arg Lys
        115                 120                 125

Gly Ala Pro Met Phe Asn Tyr Ser Lys Asp Asp Leu Leu Pro Phe Asp
    130                 135                 140

Ile Gln Gly Thr Trp Lys Ala Met Glu Glu Cys Ser Lys Leu Gly Leu
145                 150                 155                 160

Ser Lys Ser Ile Gly Val Ser Asn Tyr Thr Cys Glu Lys Leu Ser Lys
                165                 170                 175

Leu Phe Glu Asn Ala Thr Ile Pro Pro Ala Val Asn Gln Val Glu Met
            180                 185                 190

Asn Val Ser Trp Gln Gln Arg Lys Leu Leu Pro Phe Cys Lys Glu Lys
        195                 200                 205

Asn Ile His Val Thr Ala Trp Ser Pro Leu Leu Ser Tyr Gly Ser Ala
    210                 215                 220

Trp Gly Ser Asn Ala Val Met Glu Asn Pro Val Leu Val Asn Ile Ala
225                 230                 235                 240

Ala Ser Lys Ser Lys Thr Val Ala Gln Val Ala Leu Arg Trp Ile Tyr
                245                 250                 255

Gly Gln Gly Ala Ser Phe Ile Met Arg Thr Phe Asn Lys Glu Arg Met
            260                 265                 270

Phe Gln Asn Val Gln Ile Phe Asp Trp Glu Leu Ser Lys Glu Glu Leu
        275                 280                 285

Asp Gln Ile Gln Gln Ile Pro Gln Arg Arg Gly Thr Leu Gly Glu Asp
    290                 295                 300

Phe Ile Asn Pro Glu Gly Pro Ile Lys Ser Val Glu Glu Leu Trp Asp
305                 310                 315                 320

Gly Asp Leu

<210> SEQ ID NO 47
<211> LENGTH: 323
<212> TYPE: PRT
<213> ORGANISM: Tabernaemontana elegans
<220> FEATURE:
<221> NAME/KEY: MISC_FEATURE
<223> OTHER INFORMATION: REDOX 2 (reductase 2)

<400> SEQUENCE: 47

Met Ala Lys Gln Val Arg Ile Pro Glu Ile Glu Leu Asn Ser Gly His
1               5                   10                  15

Lys Met Pro Leu Val Gly Phe Gly Thr Cys Val Pro Asp Pro Ile Pro
            20                  25                  30

Pro Leu Glu Glu Leu Val Ala Ile Phe Leu Glu Ala Ile Lys Val Gly
        35                  40                  45

Tyr Arg His Phe Asp Thr Ala Ser Ser Tyr Gly Thr Glu Glu Ala Leu
    50                  55                  60

Gly Lys Ala Met Ala Gln Ala Ile Glu Gly Gly Leu Val Lys Gly Arg
65                  70                  75                  80

Glu Glu Phe Phe Ile Ser Asp Lys Leu Trp Cys Glu Asp Ala Asp His
                85                  90                  95

Asp Leu Ile Leu Pro Ala Leu Lys Thr Leu Gly Asn Thr Gly Leu
            100                 105                 110

Asp Tyr Leu Asp Leu Tyr Ile Ile His Met Pro Val Arg Val Arg Gln
        115                 120                 125

Gly Ala Pro Arg Tyr Asn Tyr Ser Lys Glu Asp Leu Leu Pro Phe Asp
    130                 135                 140
```

-continued

```
Ile Gln Gly Thr Trp Lys Ala Met Glu Glu Cys Ser Lys Leu Gly Leu
145                 150                 155                 160

Val Arg Ser Ile Gly Val Ser Asn Tyr Thr Cys Glu Lys Leu Thr Glu
            165                 170                 175

Leu Leu Gly Lys Ala Thr Ile Pro Pro Ala Val Asn Gln Val Glu Met
            180                 185                 190

Asn Val Val Trp Gln Gln Arg Lys Leu Leu Pro Phe Cys Lys Glu Lys
            195                 200                 205

Asn Ile His Val Thr Ala Trp Ser Pro Leu Leu Ser Tyr Gly Ala Ile
            210                 215                 220

Trp Gly Ser Asn Ala Val Met Glu Asn Pro Val Leu Val Glu Ile Ala
225                 230                 235                 240

Ala Ser Lys Asn Lys Thr Val Ala Gln Val Ala Leu Arg Trp Ile Tyr
            245                 250                 255

Glu Gln Gly Ala Ser Phe Ile Met Arg Thr Phe Lys Lys Glu Arg Met
            260                 265                 270

Phe Glu Asn Val Gln Ile Phe Asp Trp Glu Leu Ser Lys Glu Glu Leu
            275                 280                 285

Asp Lys Ile Gln Gln Ile His Gln Arg Arg Gly Thr Leu Gly Glu Asp
            290                 295                 300

Phe Ile His Pro Glu Gly Pro Ile Lys Ser Val Glu Glu Leu Trp Asp
305                 310                 315                 320

Gly Asp Leu
```

<210> SEQ ID NO 48
<211> LENGTH: 323
<212> TYPE: PRT
<213> ORGANISM: Vinca minor
<220> FEATURE:
<221> NAME/KEY: MISC_FEATURE
<223> OTHER INFORMATION: REDOX 2 (reductase 2)

<400> SEQUENCE: 48

```
Met Gly Lys Lys Val Glu Ile Pro Glu Ile Glu Leu Asn Ser Gly Glu
1               5                   10                  15

Lys Met Pro Ile Val Gly Tyr Gly Thr Cys Val Pro Asp Pro Ile Pro
            20                  25                  30

Pro Leu Glu Glu Leu Ser Gly Thr Phe Leu Glu Ala Met Lys Ala Gly
            35                  40                  45

Tyr Arg His Phe Asp Thr Ala Ser Ser Tyr Gly Thr Glu Glu Ala Leu
        50                  55                  60

Gly Lys Ala Val Ala Gln Ala Ile Asp Ser Gly Leu Val Asn Gly Arg
65                  70                  75                  80

Asp Glu Phe Phe Ile Ser Cys Lys Leu Trp Cys Glu Asp Ala Asp Glu
            85                  90                  95

Glu Leu Ile Leu Pro Ala Leu Lys Lys Ser Leu Gly Asp Met Gly Leu
            100                 105                 110

Asp Tyr Leu Asp Leu Tyr Met Ile His Met Pro Val Arg Val Arg Lys
            115                 120                 125

Gly Ala Pro Met Phe Ser Tyr Ser Lys Glu Asp Leu Leu Pro Phe Asp
            130                 135                 140

Ile Gln Gly Thr Trp Lys Ala Met Glu Glu Cys Ser Lys Leu Gly Leu
145                 150                 155                 160

Ala Lys Ser Ile Gly Val Ser Asn Tyr Thr Val Glu Lys Leu Thr Lys
            165                 170                 175
```

```
Leu Leu Gln His Ser Thr Ile Pro Pro Ala Val Asn Gln Val Glu Met
            180                 185                 190

Asn Val Val Trp Gln Gln Arg Lys Leu Met Pro Phe Cys Lys Glu Lys
        195                 200                 205

Asn Ile His Val Thr Ala Trp Ser Pro Leu Leu Ser Tyr Gly Val Ala
    210                 215                 220

Trp Gly Ser Asn Ala Val Met Glu Asn Pro Val Leu Leu Asp Ile Ala
225                 230                 235                 240

Ala Ser Lys Gly Lys Thr Val Ala Gln Val Ala Leu Arg Trp Val Tyr
                245                 250                 255

Glu Gln Gly Val Ser Phe Ile Ser Arg Thr Ser Asn Lys Glu Arg Met
                260                 265                 270

Tyr Glu Asn Ala Gln Ile Phe Asp Trp Glu Leu Ser Lys Glu Glu Leu
            275                 280                 285

Asp Gln Ile Gln Lys Ile Ala Gln His Lys Gly Thr Leu Gly Glu Glu
        290                 295                 300

Phe Val His Pro Glu Gly Pro Ile Lys Ser Val Glu Glu Leu Trp Asp
305                 310                 315                 320

Gly Asp Leu

<210> SEQ ID NO 49
<211> LENGTH: 421
<212> TYPE: PRT
<213> ORGANISM: Amsonia hubrichtii
<220> FEATURE:
<221> NAME/KEY: MISC_FEATURE
<223> OTHER INFORMATION: SAT (stemmadenine acetyltransferase)

<400> SEQUENCE: 49

Met Ala Ser Ile Gln Met Glu Ile Val Ser Glu Leu Ile Gln Pro
1               5                   10                  15

Ser Ser Pro Thr Pro Glu Ser Leu Lys Tyr His Lys Leu Ser Leu Leu
            20                  25                  30

Asp Gln Val Leu Leu Thr Cys His Ile Pro Ile Ile Phe Phe Tyr Pro
        35                  40                  45

Asn Gln Phe His Ser Asn Val Asp Pro Ala Gln Arg Ser Glu His Leu
    50                  55                  60

Lys Gln Ser Leu Ser Lys Val Leu Thr Lys Phe Tyr Pro Leu Ala Gly
65                  70                  75                  80

Arg Ile Asn Leu Asn Ser Ser Val Asp Cys Asn Asp Ser Gly Val Leu
                85                  90                  95

Phe Ile Glu Ala Arg Val Arg Ala Glu Leu Ser Gln Ala Ile Gln Asn
            100                 105                 110

Val Ala Ile Ala Glu Leu Asn Gln Tyr Leu Pro Phe Glu Pro Tyr Pro
        115                 120                 125

Pro Ala Glu Ser Ala Val Arg Lys Asp Ile Pro Leu Ala Val Lys Val
    130                 135                 140

Ser Phe Phe Glu Cys Gly Gly Thr Ala Val Gly Leu Cys Met Ser His
145                 150                 155                 160

Lys Ile Ala Asp Ile Leu Ser Val Thr Phe Phe Lys Ala Trp Thr
                165                 170                 175

Ala Thr Cys Gln Gly Glu Thr Asp Ile Val Leu Pro Asn Phe Asp Leu
            180                 185                 190

Ala Ser His His Phe Pro Pro Met Asp Asn Ile Pro Ala Pro Glu Trp
        195                 200                 205
```

```
Ala Pro Glu Glu Lys Ile Leu Met Lys Arg Phe Val Phe Asp Lys Glu
    210                 215                 220

Lys Leu Val Ala Leu Lys Ala Glu Ala Ser Ser Ala Ser Glu Val Lys
225                 230                 235                 240

Asn Pro Ser Arg Val Gln Leu Val Thr Ala Phe Ile Trp Lys His Ile
                245                 250                 255

Ile Asp Val Thr Arg Ser Lys Ser Asp Pro Lys Asn Lys Phe Ser Ala
            260                 265                 270

Gly Gln Ala Val Asn Leu Arg Ser Arg Met Ser Thr Pro Phe Pro Pro
        275                 280                 285

Ser Ala Met Gly Asn Ile Ala Thr Leu Ala Phe Ala Val Ala Glu Glu
    290                 295                 300

Asp Lys Leu Asp Phe Cys Asp Leu Val Gly Pro Leu Arg Thr Ala Leu
305                 310                 315                 320

Gly Lys Ile Asp Asp Glu His Val Lys Glu Leu Gln Lys Gly Val Thr
                325                 330                 335

Tyr Leu Asp Phe Glu Ala Glu Pro Gln Glu Leu Ser Ser Phe Ser Ser
            340                 345                 350

Trp Cys Arg Leu Gly Leu Tyr Glu Met Asp Phe Gly Trp Gly Lys Pro
        355                 360                 365

Leu Ser Val Cys Thr Ala Thr Leu Pro Met Lys Asn Met Val Phe Met
    370                 375                 380

Met Asp Thr Arg Ser Gly Asp Gly Leu Glu Ala Trp Ile Ser Met Ala
385                 390                 395                 400

Glu Asp Glu Met Glu Met Leu Pro Ser Gln Phe Leu Ser Leu Val Asp
                405                 410                 415

Ser Asp Phe Ser Lys
            420

<210> SEQ ID NO 50
<211> LENGTH: 420
<212> TYPE: PRT
<213> ORGANISM: Tabernaemontana elegans
<220> FEATURE:
<221> NAME/KEY: MISC_FEATURE
<223> OTHER INFORMATION: SAT (stemmadenine acetyltransferase)

<400> SEQUENCE: 50

Met Thr Ser Gln Met Glu Val Val Ser Glu Glu Leu Ile Gln Pro Ser
1               5                   10                  15

Ser Pro Thr Pro Glu Ser Leu Lys His His Lys Leu Ser Leu Leu Asp
                20                  25                  30

Gln Val Ser Leu Thr Cys His Ile Pro Ile Ile Phe Phe Tyr Pro Asn
            35                  40                  45

Gln Ser Ser Asp Ser Asn Val Asp Arg Ala Gln Arg Ser Glu His Leu
    50                  55                  60

Lys Gln Ser Leu Ser Lys Val Leu Thr Lys Phe Tyr Val Leu Ala Gly
65                  70                  75                  80

Arg Ile Asn Ile Asn Ser Ser Val Asp Cys Asn Asp Ser Gly Val Leu
                85                  90                  95

Phe Ile Glu Ala Arg Val Gln Ala Glu Leu Ser Gln Ala Ile Gln Asn
            100                 105                 110

Val Ala Ile Glu Glu Phe Asn Gln Phe Leu Pro Ile Glu Pro Tyr Pro
    115                 120                 125

Gly Gly Arg Ser Glu Val Lys Lys Asp Ile Pro Leu Ala Val Lys Ile
```

```
                130                 135                 140
Ser Phe Phe Asp Cys Gly Gly Thr Ala Val Gly Val Cys Leu Ser His
145                 150                 155                 160

Lys Ile Ala Asp Ile Leu Ser Met Ala Thr Phe Leu Asn Ala Trp Thr
                165                 170                 175

Ala Thr Cys Arg Gly Glu Thr His Ile Val Leu Pro Asn Phe Asp Leu
            180                 185                 190

Gly Ser His His Phe Pro Pro Met Asp Asn Ile Pro Ala Pro Glu Trp
                195                 200                 205

Val Pro Asp Glu Lys Ile Val Met Lys Arg Phe Val Phe Asp Lys Glu
        210                 215                 220

Lys Leu Ala Ala Leu Lys Ala Gln Ala Ser Ser Ala Ser Glu Val Lys
225                 230                 235                 240

Asn Pro Ser Arg Ile Glu Val Val Thr Ala Phe Ile Trp Lys His Phe
                245                 250                 255

Ile Asp Val Thr Arg Ala Lys Phe Tyr Thr Glu Asn Lys Phe Ala Ala
            260                 265                 270

Ala Gln Ala Val Asn Leu Arg Thr Arg Met Ser Thr Pro Leu Pro Gln
        275                 280                 285

Ser Ala Met Gly Asn Ile Ala Thr Leu Ala Phe Ala Val Ala Glu Glu
290                 295                 300

Asp Lys Asp Phe His Asp Leu Val Gly Pro Leu Arg Thr Gly Leu Gly
305                 310                 315                 320

Lys Ile Asp Asn Glu His Val Lys Asp Leu Gln Lys Gly Leu Thr Tyr
                325                 330                 335

Leu Asp Val Glu Ala Glu Pro Gln Glu Leu Ser Ser Phe Ser Ser Trp
            340                 345                 350

Cys Arg Leu Gly Phe Tyr Glu Met Asp Phe Gly Trp Gly Lys Pro Leu
        355                 360                 365

Ser Val Cys Thr Ala Asn Leu Pro Met Lys Asn Thr Val Tyr Met Met
370                 375                 380

Asp Thr Arg Ser Gly Glu Gly Ile Glu Ala Trp Ile Ser Met Ala Glu
385                 390                 395                 400

Asp Glu Met Ala Met Leu Pro Gly Glu Phe Leu Ser Leu Val Asp Ser
                405                 410                 415

Asp Phe Ser Lys
            420

<210> SEQ ID NO 51
<211> LENGTH: 423
<212> TYPE: PRT
<213> ORGANISM: Vinca minor
<220> FEATURE:
<221> NAME/KEY: MISC_FEATURE
<223> OTHER INFORMATION: SAT (stemmadenine acetyltransferase)

<400> SEQUENCE: 51

Met Ala Leu Gln Met Glu Ile Val Ser Glu Glu Leu Ile Lys Pro Ser
1               5                   10                  15

Ser Pro Thr Pro Gln Asn Leu Lys His His Lys Leu Ser His Leu Asp
            20                  25                  30

Gln Val Leu Leu Thr Cys His Ile Pro Ile Ile Leu Phe Tyr Pro Asn
        35                  40                  45

Gln Ser Thr Asn Ser Lys Phe Leu Asp Asn Thr Gln Lys Ser His His
    50                  55                  60
```

```
Leu Lys Gln Ser Leu Ser Gln Val Leu Thr Gln Phe Tyr Pro Leu Ala
 65                  70                  75                  80

Gly Arg Ile Asn Lys Asn Ser Ser Ile Asp Cys Asn Asp Tyr Gly Val
                 85                  90                  95

Pro Phe Leu Glu Ser Lys Val Gln Ser Gln Leu Ser Asp Ala Ile Gln
            100                 105                 110

Asn Ile Pro Val Lys Glu Leu Ser Gln Phe Leu Pro Phe Gln Pro Tyr
        115                 120                 125

Pro Ser Gly Asp Asn Asp Gln Glu Gly Val Lys Lys Glu Ile Pro
130                 135                 140

Leu Ala Val Lys Ile Asn Phe Phe Asp Cys Gly Ile Ala Ile Gly
145                 150                 155                 160

Val Cys Leu Ser His Lys Ile Ala Asp Ala Leu Ser Leu Ser Thr Phe
                165                 170                 175

Leu Lys Ala Trp Ala Gly Lys Ser Ser Gly Glu Ile Asp Ile Val Val
            180                 185                 190

Pro Asn Phe Asp Leu Gly Ala His His Phe Pro Ala Met Asp Asn Ile
        195                 200                 205

Pro Ala Pro Glu Phe Val Pro Asp Lys Asn Ile Val Met Glu Arg Phe
210                 215                 220

Val Phe Gly Lys Glu Lys Ile Gln Ala Leu Lys Glu Gln Ala Ser Ser
225                 230                 235                 240

Ala Ser Glu Asn Pro Ser Arg Ala Gln Val Ile Ala Leu Ile Trp
                245                 250                 255

Lys His Phe Ile Asp Val Thr Lys Ala Lys Thr Gly Ser Thr Asn Lys
            260                 265                 270

Phe Val Ala Ala Gln Ala Val Asn Leu Arg Ser Arg Met Ser Pro Pro
        275                 280                 285

Phe Pro Glu Ser Ala Met Gly Asn Ile Ala Thr Leu Ala Phe Ala Val
290                 295                 300

Ala Asp Glu Gly Arg Asp Ile Ser Asp Leu Val Gly Pro Leu Lys Asp
305                 310                 315                 320

Ser Ile Gly Lys Ile Asp Glu Glu His Val Lys Glu Leu Gln Lys Gly
                325                 330                 335

Val Thr Tyr Leu Asp Tyr Glu Ala Glu Pro Gln Glu Leu Phe Ser Phe
            340                 345                 350

Ser Ser Trp Cys Arg Leu Gly Phe Tyr Glu Leu Asp Phe Gly Trp Gly
        355                 360                 365

Lys Pro Ile Ser Ala Cys Thr Thr Thr Val Pro Met Lys Asn Leu Val
370                 375                 380

Tyr Leu Met Asp Thr Arg Asn Gly Asp Gly Ile Glu Ala Trp Ile Ser
385                 390                 395                 400

Met Glu Val Asp Glu Met Ala Met Leu Pro Ser Asp Phe Leu Ser Leu
                405                 410                 415

Val Asp Ser Asp Phe Ser Lys
            420
```

<210> SEQ ID NO 52
<211> LENGTH: 323
<212> TYPE: PRT
<213> ORGANISM: Amsonia hubrichtii
<220> FEATURE:
<221> NAME/KEY: MISC_FEATURE
<223> OTHER INFORMATION: HL2 (Hydrolase 2)

<400> SEQUENCE: 52

Met Gly Ser Leu Thr Ala Ser Ser Asp Glu Ile Ile Phe Asp Leu Pro
1               5                   10                  15

Pro Tyr Ile Arg Val Tyr Lys Asp Gly Lys Val Glu Arg Leu His Ser
            20                  25                  30

Ser Pro Tyr Val Pro Pro Ser Leu Asp Asp Pro Ala Thr Gly Val Ser
        35                  40                  45

Trp Lys Asp Val Pro Ile Ser Ser Glu Val Ser Ala Arg Ile Tyr Leu
50                  55                  60

Pro Lys Ile Ser Glu Asn Glu Lys Glu Lys Leu Pro Ile Leu Val Tyr
65                  70                  75                  80

Phe His Gly Ala Gly Phe Cys Leu Glu Ser Ala Tyr Lys Ser Phe Phe
                85                  90                  95

His Thr Tyr Val Lys His Phe Val Ala Glu Ala Lys Ala Ile Ala Val
                100                 105                 110

Ser Val Glu Phe Arg Leu Ala Pro Glu His Leu Leu Pro Ala Ala Tyr
            115                 120                 125

Glu Asp Cys Trp Thr Ala Leu Gln Trp Val Ala Ser His Val Gly Leu
    130                 135                 140

Asp Asn Ser Ser Leu Lys Asn Ala Val Asp Lys Glu Pro Trp Ile Ile
145                 150                 155                 160

Asn His Gly Asp Phe Asp Lys Leu Tyr Leu Trp Gly Asp Ser Thr Gly
                165                 170                 175

Ala Asn Ile Val His Asn Val Leu Ile Arg Ala Gly Asn Glu Asn Leu
            180                 185                 190

His Gly Gly Val Lys Ile Leu Gly Ala Ile Leu Tyr Tyr Pro Tyr Phe
        195                 200                 205

Leu Ile Arg Thr Ser Ser Arg Gln Ser Asp Tyr Met Glu Asn Asp Tyr
210                 215                 220

Arg Glu Tyr Trp Lys Leu Ala Tyr Pro Ser Ala Pro Gly Gly Asn Asp
225                 230                 235                 240

Asn Pro Met Ile Asn Pro Val Ala Glu Asn Ala Pro Asp Leu Ala Gly
                245                 250                 255

Tyr Gly Cys Ser Arg Leu Leu Val Ser Met Val Ala Asp Glu Ala Arg
            260                 265                 270

Asp Ile Thr Leu Leu Tyr Ile Glu Ala Leu Lys Lys Ser Gly Trp Lys
        275                 280                 285

Gly Glu Leu Asp Val Ala Asp Phe Glu Gly Asp Tyr Phe Glu Ser Pro
    290                 295                 300

Glu Thr Glu Ile Ala Lys Asn Arg Ile Lys Arg Leu Thr Ser Phe Ile
305                 310                 315                 320

Asn Lys Glu

<210> SEQ ID NO 53
<211> LENGTH: 323
<212> TYPE: PRT
<213> ORGANISM: Vinca minor HL
<220> FEATURE:
<221> NAME/KEY: MISC_FEATURE
<223> OTHER INFORMATION: HL2 (Hydrolase 2)

<400> SEQUENCE: 53

Met Ala Thr Ser Thr Glu Thr Ser Asp Glu Val Leu Phe Glu Leu Pro
1               5                   10                  15

Pro Tyr Ile Lys Ile Phe Lys Asp Gly Arg Val Glu Arg Leu His Ser
            20                  25                  30

-continued

Thr Pro Asn Val Pro Pro Ser Leu Asn Asp Pro Glu Thr Gly Val Ser
        35                  40                  45

Trp Lys Asp Val Pro Ile Ser Ser Gln Val Ser Ala Arg Ile Tyr Leu
 50                  55                  60

Pro Lys Ile Pro Glu Ser Glu Asn Lys Lys Leu Pro Ile Leu Val Tyr
 65                  70                  75                  80

Phe His Gly Ala Gly Phe Cys Leu Glu Ser Ala Phe Lys Glu Phe Tyr
                 85                  90                  95

His Thr Tyr Val Lys His Phe Val Ala Glu Ala Lys Ala Ile Ala Ile
                100                 105                 110

Ser Val Glu Phe Arg Leu Ala Pro Glu His Lys Leu Pro Thr Ala Tyr
            115                 120                 125

Glu Asp Cys Trp Thr Gly Leu Gln Trp Val Ser Ser His Phe Gly Leu
130                 135                 140

Asp Asn Ser Ala Leu Lys Asn Ser Ile Asp Lys Glu Ala Trp Ile Val
145                 150                 155                 160

Asn His Gly Asp Phe Ser Arg Leu Tyr Val Ser Gly Asp Ser Thr Gly
                165                 170                 175

Ala Asn Ile Val His Asn Ala Leu Leu Arg Ala Gly Lys Glu Glu Leu
            180                 185                 190

Asn Gly Gly Val Lys Ile Leu Gly Gly Ile Leu Asn Tyr Pro Tyr Phe
        195                 200                 205

Leu Ile Ser Thr Ser Glu Lys Gln Ser Asp Tyr Met Glu Asn Glu Tyr
210                 215                 220

Arg Ala Tyr Trp Lys Leu Ala Tyr Pro Glu Ala Pro Gly Gly Asp Asp
225                 230                 235                 240

Asn Pro Met Ile Asn Pro Thr Val Asp Asn Ala Pro Asp Leu Ala Gly
                245                 250                 255

Tyr Gly Cys Ser Arg Leu Leu Val Ser Met Val Ala Asp Glu Ala Arg
            260                 265                 270

Glu Ile Thr Leu Leu Tyr Ile Glu Ala Leu Lys Lys Ser Gly Trp Lys
        275                 280                 285

Gly Glu Leu Asp Val Ala Asp Phe Glu Gly Asp Tyr Phe Glu Leu Phe
290                 295                 300

Asn Leu Glu Thr Glu Val Ser Lys Asn Lys Leu Arg Arg Leu Thr Ser
305                 310                 315                 320

Phe Val Lys

<210> SEQ ID NO 54
<211> LENGTH: 325
<212> TYPE: PRT
<213> ORGANISM: Tabernaemontana elegans
<220> FEATURE:
<221> NAME/KEY: MISC_FEATURE
<223> OTHER INFORMATION: HL2 (Hydrolase 2) homolog 1

<400> SEQUENCE: 54

Met Ala Ser Ser Thr Glu Gly Ser Asp Glu Ile Ile Phe Asp Leu Pro
 1               5                  10                  15

Pro Tyr Ile Arg Val Phe Lys Asp Gly Arg Val Glu Arg Leu His Ser
             20                  25                  30

Ser Pro Tyr Val Pro Pro Ser Gln Asp Pro Ser Thr Gly Val Ser
        35                  40                  45

Trp Lys Asp Val Pro Ile Ser Ser Glu Val Ser Ala Arg Ile Tyr Leu
 50                  55                  60

```
Pro Lys Ile Ser Gln Lys Glu Lys Glu Lys Leu Pro Ile Val Val Tyr
 65                  70                  75                  80

Phe His Gly Ala Gly Phe Cys Leu Glu Ser Ala Phe Lys Ser Phe Phe
                 85                  90                  95

His Thr Tyr Val Lys His Phe Ala Ala Glu Ala Lys Ala Ile Ala Val
            100                 105                 110

Ser Val Glu Phe Arg Leu Ala Pro Glu His His Leu Pro Ala Ala Tyr
            115                 120                 125

Glu Asp Cys Trp Thr Ala Leu Gln Trp Val Ala Ser His Val Asp Val
130                 135                 140

Asp Asn Ser Ser Leu Lys Asn Ala Ile Asp Lys Glu Pro Trp Ile Ile
145                 150                 155                 160

Asn His Gly Asp Leu Asp Lys Leu Tyr Leu Trp Gly Asp Ser Thr Gly
                165                 170                 175

Ala Asn Ile Val His Asn Val Leu Ile Arg Ala Gly Asn Glu Ser Leu
            180                 185                 190

His Gly Gly Val Lys Ile Leu Gly Ala Ile Leu Tyr Tyr Pro Tyr Phe
            195                 200                 205

Leu Ile Arg Thr Ser Ser Arg Gln Ser Asp Tyr Met Glu Asn Glu Tyr
210                 215                 220

Arg Ala Tyr Trp Lys Leu Ala Tyr Pro Ser Ala Pro Gly Gly Asn Asp
225                 230                 235                 240

Asn Pro Met Ile Asn Pro Val Ala Glu Asn Ala Pro Asp Leu Ala Gly
                245                 250                 255

Tyr Gly Cys Ser Arg Leu Leu Val Ser Met Val Ala Asp Glu Ala Arg
            260                 265                 270

Asp Ile Thr Leu Leu Tyr Ile Glu Ala Val Lys Lys Ser Gly Trp Lys
            275                 280                 285

Gly Glu Leu Asp Val Ala Asp Phe Glu Gly Asp Tyr Phe Glu Ile Phe
            290                 295                 300

Ser Pro Glu Thr Glu Ile Gly Lys Asn Lys Val Thr Arg Leu Thr Ser
305                 310                 315                 320

Phe Ile Asn Lys Glu
                325

<210> SEQ ID NO 55
<211> LENGTH: 325
<212> TYPE: PRT
<213> ORGANISM: Tabernaemontana elegans
<220> FEATURE:
<221> NAME/KEY: MISC_FEATURE
<223> OTHER INFORMATION: HL2 (Hydrolase 2) homolog 2

<400> SEQUENCE: 55

Met Gly Ser Ser Thr Glu Ser Ser Asp Glu Ile Ile Phe Asp Leu Pro
  1               5                  10                  15

Pro Tyr Ile Arg Val Phe Thr Asp Gly Arg Val Glu Arg Leu His Ser
                 20                  25                  30

Ser Pro Tyr Val Pro Pro Ser Leu Asp Asp Pro Ala Thr Gly Val Ser
             35                  40                  45

Trp Lys Asp Val Pro Ile Ser Ser Glu Val Ser Ala Arg Ile Tyr Leu
         50                  55                  60

Pro Lys Ile Ser Gln Lys Asp Lys Glu Lys Leu Pro Ile Val Val Tyr
 65                  70                  75                  80

Phe His Gly Ala Gly Phe Cys Leu Glu Ser Ala Phe Lys Ser Phe Phe
```

```
                85                  90                  95
His Thr Tyr Val Lys His Phe Ala Ala Glu Ala Lys Ala Ile Ala Val
                100                 105                 110

Ser Val Glu Phe Arg Leu Ala Pro Glu His His Leu Pro Ala Ala Tyr
                115                 120                 125

Glu Asp Cys Trp Thr Ala Leu Gln Trp Val Ala Ser His Ala Asp Val
                130                 135                 140

Asp Asn Ser Ser Leu Lys Asn Ala Ile Asp Lys Glu Pro Trp Ile Ile
145                 150                 155                 160

Asn Arg Gly Asp Phe Asp Lys Leu Tyr Leu Trp Gly Asp Ser Thr Gly
                165                 170                 175

Ala Asn Ile Val His Asn Val Leu Ile Arg Ala Gly Asn Glu Ser Leu
                180                 185                 190

His Gly Gly Val Lys Ile Leu Gly Ala Ile Leu Tyr Tyr Pro Tyr Phe
                195                 200                 205

Leu Ile Arg Thr Ser Ser Arg Gln Ser Asp Tyr Met Glu Asn Glu Tyr
                210                 215                 220

Arg Ala Tyr Trp Lys Leu Ala Tyr Pro Ser Ala Pro Gly Gly Asn Asp
225                 230                 235                 240

Asn Pro Met Ile Asn Pro Val Ala Glu Asn Ala Pro Asp Leu Ala Gly
                245                 250                 255

Tyr Gly Cys Ser Arg Leu Leu Val Ser Met Val Ala Asp Glu Ala Arg
                260                 265                 270

Asp Ile Thr Leu Leu Tyr Ile Glu Ala Val Lys Lys Ser Gly Trp Lys
                275                 280                 285

Gly Glu Leu Asp Val Ala Asp Phe Glu Gly Asp Tyr Phe Glu Ile Phe
                290                 295                 300

Ser Pro Glu Thr Glu Ile Gly Lys Asn Lys Val Thr Arg Leu Thr Ser
305                 310                 315                 320

Phe Ile Asn Lys Glu
                325

<210> SEQ ID NO 56
<211> LENGTH: 366
<212> TYPE: PRT
<213> ORGANISM: Tabernaemontana elegans
<220> FEATURE:
<221> NAME/KEY: MISC_FEATURE
<223> OTHER INFORMATION: HL2 (Hydrolase 2) homolog 3

<400> SEQUENCE: 56

Met Tyr Thr Ile Lys Ile Tyr Lys Val Arg Leu Gln Tyr Ser Tyr Pro
1               5                   10                  15

His Leu His Pro His Leu His Lys Leu Val Thr Pro Gln Arg Glu Thr
                20                  25                  30

Asp Asn Ile Arg Gln Leu Ile Ala Leu Arg Phe Ile Leu Ala Met Ala
                35                  40                  45

Ser Asp Glu Ile Ala Ile Asp Ile Ser Pro Asp Ile Leu Tyr Lys
                50                  55                  60

Asp Gly Lys Val Val Arg Asn Phe Val Gln Pro Tyr Val Pro Pro Ser
65                  70                  75                  80

Leu Glu Asp Pro Thr Thr Gly Val Ser Thr Lys Asp Val Pro Ile Ser
                85                  90                  95

Pro Glu Val Ser Ala Arg Val Tyr Leu Pro Lys Val Ile Ile Asp Gly
                100                 105                 110
```

-continued

```
Gln Lys Leu Pro Ile Leu Val Tyr Phe His Gly Gly Gly Phe Cys Leu
        115                 120                 125

Val Ser Ala Phe Asp Ser Leu Tyr Asn Thr Tyr Leu Lys Leu Leu Val
    130                 135                 140

Ser Glu Ala Asn Ala Ile Val Val Thr Val Glu Phe Arg Leu Thr Pro
145                 150                 155                 160

Glu Tyr Pro Leu Pro Thr Gly Tyr Glu Asp Cys Trp Thr Ala Leu Gln
                165                 170                 175

Trp Val Ala Ser His Ala Val Asp Tyr Ser Thr Thr Gly Val Asp Arg
                180                 185                 190

Glu Pro Trp Leu Ile Asn Tyr Gly Asn Phe Asp Lys Leu Tyr Ile Gly
            195                 200                 205

Gly Asp Ser Thr Gly Gly Asn Met Val His Asn Ile Ala Met Arg Ala
        210                 215                 220

Gly Gln Glu Asn Leu Gln Gly Gly Leu Lys Ile Leu Gly Gly Ile Leu
225                 230                 235                 240

Ser Tyr Pro Tyr Phe Leu Val Ser Ser Trp Ala Lys Lys Asn Glu Glu
                245                 250                 255

Thr Leu Ser Asp Met Val Lys Met Tyr Lys Lys Tyr Trp Leu Leu Ser
                260                 265                 270

Tyr Pro Ser Ala Pro Gly Gly Tyr Glu Asn Pro Leu Val Asn Pro Val
        275                 280                 285

Val Asp Asp Ala Pro Ser Leu Ala Gly Ile Gly Cys Ser Ser Leu Leu
    290                 295                 300

Val Ile Met Ala Ile Asp Asp Val Arg Glu Ala His Leu Leu Tyr Val
305                 310                 315                 320

Glu Ala Leu Arg Lys Ser Gly Trp Lys Gly Glu Leu Glu Leu Ala Asp
                325                 330                 335

Phe Glu Gly Tyr Asp His Phe Phe Glu Val Phe Asn Pro Thr Thr Gln
                340                 345                 350

Arg Ala Lys Asn Met Ile Lys Arg Ile Ala Ser Phe Ile Lys
                355                 360                 365
```